(12) United States Patent
van Wezel et al.

(10) Patent No.: US 8,313,929 B2
(45) Date of Patent: Nov. 20, 2012

(54) GROWTH CHARACTERISTICS OF FILAMENTOUS MICROORGANISMS

(75) Inventors: Gilles Philippus van Wezel, Oegstgeest (NL); Erik Vijgenboom, Berkel en Rodenrijs (NL)

(73) Assignee: Universiteit Leiden, Leiden (NL)

( * ) Notice: Subject to any disclaimer, the term of this patent is extended or adjusted under 35 U.S.C. 154(b) by 445 days.

(21) Appl. No.: 11/122,967

(22) Filed: May 5, 2005

(65) Prior Publication Data

US 2006/0024830 A1    Feb. 2, 2006

Related U.S. Application Data

(63) Continuation of application No. PCT/NL03/00779, filed on Nov. 6, 2003.

(30) Foreign Application Priority Data

Nov. 6, 2002  (EP) .................................... 02079637

(51) Int. Cl.
C12P 21/00    (2006.01)
C07K 14/00    (2006.01)

(52) U.S. Cl. ...................................... 435/71.1; 530/350
(58) Field of Classification Search ........................ None
See application file for complete search history.

(56) References Cited

U.S. PATENT DOCUMENTS 7,022,526 B2 *   4/2006   van Wezel et al. ............ 435/484

FOREIGN PATENT DOCUMENTS

| WO | WO 00/00613 | 1/2000 |
| WO | WO 2004/041858 A2 | 5/2004 |
| WO | WO 2004/041858 A3 | 5/2004 |

OTHER PUBLICATIONS

GenBank accession No. NP_628111.*
Buecher et al. Liquid culture of the entomogenous nematode *Steinernema feltiae* with its bacterial symbiont. Journal of Nematology. 21(4): 500-504, 1989.*
Oh et al. Isolation and Properties of an Extracellular β-Glucosidase from a Filamentous Fungus, *Cladosporium resinae*, Isolated from Kerosene. Bioscience, Biotechnology, and Biochemistry vol. 63 (1999), No. 2 pp. 281-287.*
Genbank accession No. NP_631345.1.*
Xu et al. Structural and Functional Characterizations of SsgB, a Conserved Activator of Developmental Cell Division in Morphologically Complex Actinomycetes. The Journal of Biological Chemistry, 284, 25268-25279, 2009.*
Jonsbu et al. The influence of carbon sources and morphology on nystatin production by *Streptomyces noursei*. J Biotechnol. May 9, 2002;95(2):133-44.*
Webster Dictionary online, www.merriam-webster.com/dictionary/provide, 2011.*
Genbank accession No. Q9X7R1, 2012.*
GenBank accession No. NP_628111, 2008.*
GenBank accession No. NP_631345.1, 2010.*
Kormanec J. et al., "The stress-response sigma factor sigma(H) controls the expression of ssgB, a homologue of the sporulation-specific cell division gene ssgA, in *Streptomyces coelicolor* A3(2)", Mol. Genet. Genomics, 267(4), 536-543 (2002).
Van Wezel G.P. et al., "Effects of increased and deregulated expression of cell division genes on the morphology and on antibiotic production of streptomycetes", Antonie Van Leeuwenhoek, 78(3-4), 269-276 (2000).
Van Wezel G.P. et al., "ssgA is essential for sporulation of *Streptomyces coelicolor* A3(2) and affects hyphal development by stimulating septum formation", J. Bacteriol. 182(20), 5653-5662 (2000).
Kawamoto S, et al., "Expression analysis of the ssgA gene product, associated with sporulation and cell division in *Streptomyces griseus*", Microbiology, 143 ( Pt 4):1077-1086 (1997).
Kwak et al., Differential Regulation of ftsZ transcription during Septation of *Streptomyces griseus*, Journal of Bacteriology, Sep. 2001, pp. 5092-5101, vol. 183, No. 17.
Kawamoto et al., Cloning and Characterization of a Gene Involved in Regulation of Sporulation and Cell Division of *Streptomyces griseus*, Actinomycetol., 1995, pp. 136-151, vol. 9, No. 2.

* cited by examiner

*Primary Examiner* — Michele K Joike
(74) *Attorney, Agent, or Firm* — TraskBritt

(57) ABSTRACT

The invention relates to industrial microbiology, in particular to fermentation technology and especially to fermentation methods for filamentous microorganisms, in particular, filamentous microorganisms such as actinomycetes. The present invention discloses a method for improving the production of a product of interest in a liquid culture of filamentous microorganisms comprising providing the filamentous microorganisms with an agent for altering the morphology of microstructures of the filamentous microorganisms. The invention also relates to a method for improving the production of a product of interest in a liquid culture of filamentous microorganisms comprising altering in the filamentous microorganisms the expression level or copy number of an endogenous agent for altering the morphology of microstructures of the filamentous microorganisms. The invention further provides multiple methods for obtaining a filamentous microorganism with altered, preferably enhanced, fragmentation characteristics. However, a filamentous microorganism with reduced fragmentation characteristics is also included.

4 Claims, 26 Drawing Sheets

```
-254  GGCCGGCCACGATGGCCATCTCACTGCCCCTCCACCAGGCGGACCGTTTGCTCCCCGCGGC
      CCGGCCGGTGCTACCGGTAGAGTGACGGGGAGGTGGTCCGCTGCAAACGAGGGCGCCG
       A  A  T  M  A  I  S  L  P  L  H  Q  A  D  R  L  L  P  A  A
                            T7-AR
-194  TCAGCGGGTTGCAGAAACGAGGTGGGGGCGCTGTCGGGGTCGCGCTCTCTATCAGTAT
      AGTCGCCAACGTCTTTGCTCCACCCCCGCGACAGACCCCAGCAGCGCGAGAGATAGTCATA
       Q  R  L  Q  N  E  V  G  R  R  L  G  S  L  A  L  S  I  S  I
                                                                    ◆
-134  CTGAAAACTCACTCCTTGTGATCTGGTGTGTACGTTGAGCAAGATGCCATCAGTGTTAGA
      GACTTTTGAGTGAGGAACACTAGACCACACATGCAACTCGTTCTACGGTAGTCACAATCT
       *  (SEQ ID NO:5)
                  -10                                         ◆
-74   GGTTTGATTCCCGGACAGTCGACGGCGAATGACGGGTAGGCGAATGGGCGAGTCCGTAC
      CCAAACTAAGGGCCCTGTCAGCTGCCGCTTACTGCCCATCCGCTTACCCGCTCAGGCATG
                                                               T7-AF
-14   AGGCAGAGGTCATGATGAGCTTTCTCGTGTCCGAGGAGCTCTCTTTCCGAATCCCGGTGG
      TCCGTCTCCAGTACTACTCGAAAGAGCACAGGCTCCTCGAGAGAAAGGCCTAGGGCCACC
       M  S  F  L  V  S  E  E  L  S  F  R  I  P  V  E
         Start ssgA
              BamHI
+47   AGCTGCGCTACGAGACCCGGGATCCCTATGCCGTACGCCTGACCTTTCATCTGCCCGGAG (SEQ ID NO:4)
      TCGACGCGATGCTCTGGGCCCTAGGGATACGGCATGCGGACTGGAAAGTAGACGGGCCTC
       L  R  Y  E  T  R  D  P  Y  A  V  R  L  T  F  H  L  P  G  D (SEQ ID NO:6)
```

Fig. 4B

-134 CTGAAAACTCACTCCTTGTGATCTGGTGTGTACGTTGAGCAAGATGCCATCA-GTGTTAG
         A                       C A CG-   GC C  C   G G   ATA GGCC

-10         *
-74  A-GGTT--TGATTCCCGGACAGTCGACGGGCGAATGACGGGGTAGGCGAATGGGCGAGTCCGTAC
     T  GGGA C      T  C   A  CATCT- C  -    T AA G   C        G   T

-14  AGGCAGAGGTCATGATGAGCTTTCTCGTGTCCGAGGAGCTCT (SEQ ID NO:7)
                                              (SEQ ID NO:8)

Map of ssgB, flanking genes and constructs

Map of ssgC, flanking genes and constructs

Map of ssgD, flanking genes and constructs

Map of ssgE, flanking genes and constructs

Map of *ssgF*, flanking genes and constructs

Map of *ssgG*, flanking genes and constructs

E19A.23 encodes a hypothetical protein (224 aa)
E19A.25 encodes a GlcD homologue (488 aa)
Repeat region contains many degenerate AAGGCC sequences Phenotype of the ssgB mutant of S. coelicolor (Scanning EM)

M145 (wt)

ssgB mutant (GSB1)

MM + Mannitol          MM + glucose

SEQUENCE LISTING

```
<160> NUMBER OF SEQ ID NOS: 21

<210> SEQ ID NO 1
<211> LENGTH: 11
<212> TYPE: PRT
<213> ORGANISM: Artificial Sequence
<220> FEATURE:
<223> OTHER INFORMATION: Signature A
<220> FEATURE:
<221> NAME/KEY: MISC_FEATURE
<222> LOCATION: (1)..(1)
<223> OTHER INFORMATION: "X" on pos. 1 stands for I or V in that
      position
<220> FEATURE:
<221> NAME/KEY: MISC_FEATURE
<222> LOCATION: (2)..(2)
<223> OTHER INFORMATION: "X" on pos. 2 stands for P or L in that
      position
<220> FEATURE:
<221> NAME/KEY: MISC_FEATURE
<222> LOCATION: (3)..(3)
<223> OTHER INFORMATION: "X" on pos. 3 stands for A or V in that
      position
<220> FEATURE:
<221> NAME/KEY: MISC_FEATURE
<222> LOCATION: (4)..(4)
<223> OTHER INFORMATION: "X" on pos. 4 stands for any amino acid
<220> FEATURE:
<221> NAME/KEY: MISC_FEATURE
<222> LOCATION: (5)..(5)
<223> OTHER INFORMATION: "X" on pos. 5 stands for F or L in that
      position
<220> FEATURE:
<221> NAME/KEY: MISC_FEATURE
<222> LOCATION: (6)..(6)
<223> OTHER INFORMATION: "X" on pos. 6 stands for any amino acid
<220> FEATURE:
<221> NAME/KEY: MISC_FEATURE
<222> LOCATION: (8)..(8)
<223> OTHER INFORMATION: "X" on pos. 8 stands for D, E or H in that
      position
<220> FEATURE:
<221> NAME/KEY: MISC_FEATURE
<222> LOCATION: (9)..(9)
<223> OTHER INFORMATION: "X" on pos. 9 stands for 2 or 3 of any amino
      acid
```

-continued

```
<220> FEATURE:
<221> NAME/KEY: MISC_FEATURE
<222> LOCATION: (10)..(10)
<223> OTHER INFORMATION: "X" on pos. 10 stands for D or H in that
      position

<400> SEQUENCE: 1

Xaa Xaa Xaa Xaa Xaa Xaa Tyr Xaa Xaa Xaa Pro
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Signature B
<220> FEATURE:
<221> NAME/KEY: MISC_FEATURE
<222> LOCATION: (2)..(2)
<223> OTHER INFORMATION: "X" on pos. 2 stands for any amino acid
<220> FEATURE:
<221> NAME/KEY: MISC_FEATURE
<222> LOCATION: (3)..(3)
<223> OTHER INFORMATION: "X" on pos. 3 stands for F, V or L in that
      position
<220> FEATURE:
<221> NAME/KEY: MISC_FEATURE
<222> LOCATION: (4)..(4)
<223> OTHER INFORMATION: "X" on pos. 4 stands for any amino acid
<220> FEATURE:
<221> NAME/KEY: MISC_FEATURE
<222> LOCATION: (6)..(6)
<223> OTHER INFORMATION: "X" on pos. 6 stands for E or D in that
      position
<220> FEATURE:
<221> NAME/KEY: MISC_FEATURE
<222> LOCATION: (7)..(7)
<223> OTHER INFORMATION: "X" on pos. 7 stands for L or M in that
      position
<220> FEATURE:
<221> NAME/KEY: MISC_FEATURE
<222> LOCATION: (8)..(8)
<223> OTHER INFORMATION: "X" on pos. 8 stands for L or V in that
      position
<220> FEATURE:
<221> NAME/KEY: MISC_FEATURE
<222> LOCATION: (9)..(10)
<223> OTHER INFORMATION: "X" on pos. 9 and 10 stands for any amino
      acid

<400> SEQUENCE: 2

Trp Xaa Xaa Xaa Arg Xaa Xaa Xaa Xaa Xaa Gly
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Signature C
<220> FEATURE:
<221> NAME/KEY: MISC_FEATURE
<222> LOCATION: (2)..(2)
<223> OTHER INFORMATION: "X" on pos. 2 stands for any amino acid
<220> FEATURE:
<221> NAME/KEY: MISC_FEATURE
<222> LOCATION: (3)..(3)
<223> OTHER INFORMATION: "X" on pos. 3 stands for F, V or L in that
      position
<220> FEATURE:
<221> NAME/KEY: MISC_FEATURE
<222> LOCATION: (4)..(4)
<223> OTHER INFORMATION: "X" on pos. 4 stands for any amino acid
<220> FEATURE:
<221> NAME/KEY: MISC_FEATURE
<222> LOCATION: (6)..(6)
```

```
<223> OTHER INFORMATION: "X" on pos. 3 stands for E or D in that
      position
<220> FEATURE:
<221> NAME/KEY: MISC_FEATURE
<222> LOCATION: (7)..(7)
<223> OTHER INFORMATION: "X" on pos. 7 stands for L or M in that
      position
<220> FEATURE:
<221> NAME/KEY: MISC_FEATURE
<222> LOCATION: (8)..(8)
<223> OTHER INFORMATION: "X" on pos. 8 stands for L or V in that
      position
<220> FEATURE:
<221> NAME/KEY: MISC_FEATURE
<222> LOCATION: (9)..(10)
<223> OTHER INFORMATION: "X" on pos. 9 and 10 stands for any amino
      acid
<220> FEATURE:
<221> NAME/KEY: MISC_FEATURE
<222> LOCATION: (12)..(12)
<223> OTHER INFORMATION: "X" on pos. 12 stands for 5 of any amino
      acid
<220> FEATURE:
<221> NAME/KEY: MISC_FEATURE
<222> LOCATION: (14)..(14)
<223> OTHER INFORMATION: "X" on pos. 14 stands for any amino acid
<220> FEATURE:
<221> NAME/KEY: MISC_FEATURE
<222> LOCATION: (16)..(16)
<223> OTHER INFORMATION: "X" on pos. 16 stands for D or E in that
      position

<400> SEQUENCE: 3

Trp Xaa Xaa Xaa Arg Xaa Xaa Xaa Xaa Gly Xaa Gly Xaa Gly Xaa
1               5                   10                  15

Val

<210> SEQ ID NO 4
<211> LENGTH: 360
<212> TYPE: DNA
<213> ORGANISM: Streptomyces coelicolor

<400> SEQUENCE: 4
ggccgccacg atggccatct cactgcccct ccaccaggcg gaccgtttgc tccccgcggc     60
tcagcggttg cagaacgagg tggggcggcg tctggggtcg ctcgcgctct ctatcagtat    120
ctgaaaactc actccttgtg atctggtgtg tacgttgagc aagatgccat cagtgttaga    180
ggtttgattc ccggacagtc gacggcgaat gacggggtag gcgaatgggc gagtccgtac    240
aggcagaggt catgatgagc tttctcgtgt ccgaggagct ctctttccgc atcccggtgg    300
agctgcgcta cgagacccgg gatccctatg ccgtacgcct gacctttcat ctgcccggag    360

<210> SEQ ID NO 5
<211> LENGTH: 40
<212> TYPE: PRT
<213> ORGANISM: Streptomyces coelicolor

<400> SEQUENCE: 5

Ala Ala Thr Met Ala Ile Ser Leu Pro Leu His Gln Ala Asp Arg Leu
1               5                   10                  15

Leu Pro Ala Ala Gln Arg Leu Gln Asn Glu Val Gly Arg Arg Leu Gly
            20                  25                  30

Ser Leu Ala Leu Ser Ile Ser Ile
        35                  40

<210> SEQ ID NO 6
<211> LENGTH: 36
<212> TYPE: PRT
```

-continued

<213> ORGANISM: Streptomyces coelicolor

<400> SEQUENCE: 6

Met Ser Phe Leu Val Ser Glu Glu Leu Ser Phe Arg Ile Pro Val Glu
1               5                   10                  15

Leu Arg Tyr Glu Thr Arg Asp Pro Tyr Ala Val Arg Leu Thr Phe His
            20                  25                  30

Leu Pro Gly Asp
        35

<210> SEQ ID NO 7
<211> LENGTH: 162
<212> TYPE: DNA
<213> ORGANISM: Streptomyces coelicolor

<400> SEQUENCE: 7
ctgaaaactc actccttgtg atctggtgtg tacgttgagc aagatgccat cagtgttaga      60
ggtttgattc ccggacagtc gacggcgaat gacggggtag gcgaatgggc gagtccgtac     120
aggcagaggt catgatgagc tttctcgtgt ccgaggagct ct                        162

<210> SEQ ID NO 8
<211> LENGTH: 163
<212> TYPE: DNA
<213> ORGANISM: Streptomyces griseus

<400> SEQUENCE: 8
ctgaaaaatc actccttgtg atctgctatc gcgtgcacca cgatggcgtc aatagggcca      60
tgggggatca ttcctggcca gacgcatcta ctgcggggtt gaaggatgcg cgagtcggtt     120
caggcagagg tcatgatgag ctttctcgtg tccgaggagc tct                       163

<210> SEQ ID NO 9
<211> LENGTH: 137
<212> TYPE: PRT
<213> ORGANISM: Streptomyces coelicolor

<400> SEQUENCE: 9

Met Asn Thr Thr Val Ser Cys Glu Leu His Leu Arg Leu Val Val Ser
1               5                   10                  15

Ser Glu Ser Ser Leu Pro Val Pro Ala Gly Leu Arg Tyr Asp Thr Ala
            20                  25                  30

Asp Pro Tyr Ala Val His Ala Thr Phe His Thr Gly Ala Glu Glu Thr
        35                  40                  45

Val Glu Trp Val Phe Ala Arg Asp Leu Leu Ala Glu Gly Leu His Arg
    50                  55                  60

Pro Thr Gly Thr Gly Asp Val Arg Val Trp Pro Ser Arg Ser His Gly
65                  70                  75                  80

Gln Gly Val Val Cys Ile Ala Leu Ser Ser Pro Glu Gly Glu Ala Leu
                85                  90                  95

Leu Glu Ala Pro Ala Arg Ala Leu Glu Ser Phe Leu Lys Arg Thr Asp
            100                 105                 110

Ala Ala Val Pro Pro Gly Thr Glu His Arg His Phe Asp Leu Asp Gln
        115                 120                 125

Glu Leu Ser His Ile Leu Ala Glu Ser
    130                 135

<210> SEQ ID NO 10
<211> LENGTH: 142
<212> TYPE: PRT

-continued

<213> ORGANISM: Streptomyces coelicolor

<400> SEQUENCE: 10

Met His Thr Asn Pro Thr Gly Pro Thr Val Val Glu Arg Glu Leu Glu
1               5                   10                  15

Leu Arg Leu Val Leu Ser Pro Glu Ser Gly Ile Pro Val Pro Ala Arg
            20                  25                  30

Leu Gly Tyr His Thr Asp Asp Pro Tyr Ala Val His Ile Thr Phe His
        35                  40                  45

Ile Asp Ser Gly His Pro Val His Trp Thr Phe Ala Arg Asp Leu Leu
50                  55                  60

Val Glu Gly Val Phe Arg Pro Ser Gly His Gly Asp Val Arg Val Trp
65                  70                  75                  80

Pro Ser Lys Thr Glu Gly Arg Ser Val Val Leu Val Ala Leu Ser Ser
                85                  90                  95

Pro Asp Gly Asp Ala Leu Leu Glu Ala Pro Thr Pro Gln Val Ser Ala
            100                 105                 110

Trp Leu Glu Arg Thr Leu Arg Ala Val Pro Pro Gly Thr Glu Gly Ala
        115                 120                 125

Gln Leu Gly Ile Asp Asp Gly Leu Ala Glu Leu Leu Ala Arg
    130                 135                 140

<210> SEQ ID NO 11
<211> LENGTH: 135
<212> TYPE: PRT
<213> ORGANISM: Streptomyces coelicolor

<400> SEQUENCE: 11

Met Ser Phe Leu Val Ser Glu Glu Leu Ser Phe Arg Ile Pro Val Glu
1               5                   10                  15

Leu Arg Tyr Glu Thr Arg Asp Pro Tyr Ala Val Arg Leu Thr Phe His
            20                  25                  30

Leu Pro Gly Asp Ala Pro Val Thr Trp Ala Phe Gly Arg Glu Leu Leu
        35                  40                  45

Val Asp Gly Val Gly Arg Pro Cys Gly Asp Gly Asp Val Arg Ile Ala
50                  55                  60

Pro Val Glu Pro Glu Pro Leu Ala Glu Val Leu Ile Arg Leu Gln Val
65                  70                  75                  80

Gly Ser Asp Gln Ala Leu Phe Arg Ser Ala Ala Pro Leu Val Ala
                85                  90                  95

Phe Leu Asp Arg Thr Asp Lys Leu Val Pro Leu Gly Gln Glu Gly Ala
            100                 105                 110

Leu Ala Asp Phe Asp Ser His Leu Asp Glu Ala Leu Asp Arg Ile Leu
        115                 120                 125

Ala Glu Glu Gln Ser Ala Gly
    130                 135

<210> SEQ ID NO 12
<211> LENGTH: 156
<212> TYPE: PRT
<213> ORGANISM: Streptomyces coelicolor

<400> SEQUENCE: 12

Met Ser Gly Asp His His Gly Val Gln Ala Gln His Ser Ala Ala Gln
1               5                   10                  15

Ala Leu Leu Pro Leu Ser Leu Cys Leu Ser Gln Met Thr Gly Ala Leu
            20                  25                  30

```
Glu Trp Glu Asp Val Pro Ala Glu Phe Arg Tyr Asp Pro Asp His Pro
             35                  40                  45

Leu Leu Val Thr Ile Arg Phe Ala Pro Glu Gly Ala Pro Pro Val Thr
 50                  55                  60

Trp His Val Gly Arg Asp Leu Leu His Glu Gly Leu Arg Thr Thr Ser
 65                  70                  75                  80

Gly Leu Gly Asp Val Gln Val Trp Ala Asp Thr Pro Thr Asp Arg Glu
                 85                  90                  95

Thr Ala Trp Leu Gln Val Asn Ala His Gly Asp Ile Ala Ile Phe Ser
            100                 105                 110

Leu Pro Val Pro Glu Leu Glu Glu Trp Ile Asp Arg Thr Tyr Leu His
            115                 120                 125

Val Pro Ala Gly Thr Glu Ser Ser Arg Leu Gly Thr Asp Ala Phe Leu
130                 135                 140

Ser Lys Leu Phe Asp Glu Pro Glu Ala Ser Ser Arg
145                 150                 155

<210> SEQ ID NO 13
<211> LENGTH: 138
<212> TYPE: PRT
<213> ORGANISM: Streptomyces coelicolor

<400> SEQUENCE: 13

Met Ser Thr Val Ile Glu Gln Ser Val Glu Ala Arg Leu Val Ala Ala
 1               5                  10                  15

Ala Pro Arg Met Pro Ser Ile Pro Ala Thr Leu His Tyr Asp Arg Ala
             20                  25                  30

Asp Pro Phe Ala Val Arg Met Thr Phe Pro Ala Pro Ala Thr Leu Glu
         35                  40                  45

Gly Val Glu Val Cys Trp Thr Phe Ser Arg Glu Leu Leu Ile Ala Gly
 50                  55                  60

Met Gln Glu Pro Asn Gly His Gly Asp Val Arg Val Arg Pro Tyr Ala
 65                  70                  75                  80

Tyr Asp Arg Thr Val Leu Glu Phe His Ala Pro Glu Gly Thr Ala Val
                 85                  90                  95

Ile His Val Arg Ser Gly Glu Leu Arg Arg Phe Leu Gln Ala Ala Gly
            100                 105                 110

Glu Leu Val Pro Val Gly Leu Glu His Leu Gln Leu Asp Leu Asp His
            115                 120                 125

Asp Leu Ala Glu Leu Met Arg Gly Ser Cys
130                 135

<210> SEQ ID NO 14
<211> LENGTH: 126
<212> TYPE: PRT
<213> ORGANISM: Streptomyces coelicolor

<400> SEQUENCE: 14

Met Ser Val Val Glu Gln Tyr Ala Arg Ala His Ile Leu Thr Asp Gly
 1               5                  10                  15

Asp Leu Pro Asp Gln Asp Gly Gly Ala Ile Pro Val Val Leu Arg
             20                  25                  30

Tyr Asp Pro Gln Leu Asp Pro Ser Lys Val Cys Val Ala Leu Pro Gly
         35                  40                  45

Arg Gly Gly Arg Ala Ser Gly Ser Arg Glu Trp Thr Phe Ser Arg Glu
 50                  55                  60

Leu Leu Glu Gln Gly Leu Arg Ala Pro Ala Gly Ser Gly Glu Val Arg
```

-continued

```
                65                  70                  75                  80
Val Trp Pro Cys Gly Arg Val Gln Ala Val Val Glu Phe His Ser Pro
                    85                  90                  95
Gln Gly Cys Ser Val Val Gln Phe Glu Asn Lys Ala Leu Ile Arg Phe
                    100                 105                 110
Leu Arg Arg Thr Tyr Ala Ala Thr Ala Gln Pro Val Ala His
                    115                 120                 125

<210> SEQ ID NO 15
<211> LENGTH: 142
<212> TYPE: PRT
<213> ORGANISM: Streptomyces coelicolor

<400> SEQUENCE: 15

Met Asn Thr Val Val His Lys Thr Leu Val Val Gln Leu Gln Ala Gly
1               5                   10                  15
Gly Thr Ala Asp Arg Phe Pro Val Leu Ala His Leu Ala Tyr Asp Ala
                20                  25                  30
Ala Asp Pro Phe Ala Leu Thr Val Val Phe Ser His Asp Gly Arg Val
            35                  40                  45
Leu Ala Arg Trp Thr Leu Asp Arg Glu Met Val Ala Glu Gly Leu Thr
        50                  55                  60
Arg Pro Val Gly Val Gly Asp Val Arg Leu Arg Pro Glu Ser Arg Gly
65                  70                  75                  80
Met Trp Asp Glu Leu Arg Ile Glu Leu Leu Gly Asp Gly Arg Ala Asp
                85                  90                  95
Gly Glu Arg His Arg Ala Val Val Phe Val Trp Ala Ala Ala Val Glu
                100                 105                 110
Ala Phe Leu Arg Glu Thr His Ala Val Val Arg Pro Gly Arg Glu Glu
            115                 120                 125
Val Arg Val Asp Asp Phe Leu Ala Glu Leu Thr Ala Glu Gly
        130                 135                 140

<210> SEQ ID NO 16
<211> LENGTH: 4
<212> TYPE: PRT
<213> ORGANISM: Artificial Sequence
<220> FEATURE:
<223> OTHER INFORMATION: Consensus sequence of part of ssgA like
      proteins of Steptomyces Coelicolor

<400> SEQUENCE: 16

Asn Thr Val Val
1

<210> SEQ ID NO 17
<211> LENGTH: 4
<212> TYPE: PRT
<213> ORGANISM: Artificial Sequence
<220> FEATURE:
<223> OTHER INFORMATION: Consensus sequence of part of ssgA like
      proteins of Steptomyces Coelicolor

<400> SEQUENCE: 17

Leu Arg Tyr Asp
1

<210> SEQ ID NO 18
<211> LENGTH: 4
<212> TYPE: PRT
<213> ORGANISM: Artificial Sequence
<220> FEATURE:
```

```
<223> OTHER INFORMATION: Consensus sequence of part of ssgA like
      proteins of Steptomyces Coelicolor

<400> SEQUENCE: 18

Asp Pro Tyr Ala
1

<210> SEQ ID NO 19
<211> LENGTH: 5
<212> TYPE: PRT
<213> ORGANISM: Artificial Sequence
<220> FEATURE:
<223> OTHER INFORMATION: Consensus sequence of part of ssgA like
      proteins of Steptomyces Coelicolor

<400> SEQUENCE: 19

Val His Ile Thr Phe
1               5

<210> SEQ ID NO 20
<211> LENGTH: 8
<212> TYPE: PRT
<213> ORGANISM: Artificial Sequence
<220> FEATURE:
<223> OTHER INFORMATION: Consensus sequence of part of ssgA like
      proteins of Steptomyces Coelicolor

<400> SEQUENCE: 20

Trp Thr Phe Ala Arg Glu Leu Leu
1               5

<210> SEQ ID NO 21
<211> LENGTH: 7
<212> TYPE: PRT
<213> ORGANISM: Artificial Sequence
<220> FEATURE:
<223> OTHER INFORMATION: Consensus sequence of part of ssgA like
      proteins of Steptomyces Coelicolor

<400> SEQUENCE: 21

Gly Asp Val Arg Val Trp Pro
1               5
```

GROWTH CHARACTERISTICS OF FILAMENTOUS MICROORGANISMS

CROSS-REFERENCE TO RELATED APPLICATIONS

This application is a continuation of PCT International Patent Application No. PCT/NL2003/000779, filed on Nov. 6, 2003, designating the United States of America, and published, in English, as PCT International Publication No. WO 2004/041858 A2 on May 21, 2004, which application claims priority to European Patent Application No. 02079637.1, filed Nov. 6, 2002, the contents of the entirety of each of which are incorporated herein by this reference.

STATEMENT ACCORDING TO 37 C.F.R. §1.52(e)(5)—SEQUENCE LISTING SUBMITTED ON COMPACT DISC

Pursuant to 37 C.F.R. §1.52(e)(1)(iii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "Sequence Listing as submitted.txt" which is 114 KB and created on May 20, 2005.

TECHNICAL FIELD

The invention relates to industrial microbiology, in particular, to fermentation technology and especially to fermentation methods for filamentous microorganisms, in particular, filamentous microorganisms such as actinomycetes.

BACKGROUND

*Streptomycetes* are Gram-positive, aerobic, filamentous soil bacteria, which belong to the order of *actinomycetales*. In an early stage of *Streptomyces* growth on a solid medium, spores germinate and subsequently develop into a vegetative mycelium of multinucleoid and branching hyphae with occasional cross-walls (Chater, 1993). After environmental signals such as nutrient depletion, aseptate aerial hyphae are formed, growing on the vegetative hyphae, the latter being used as a substrate. Eventually, the aerial hyphae form uninucleoid cells that develop into hydrophobic spores, which are budded off from the tips of the hyphae. One of the striking features of *streptomycetes* and other members of the order of *actinomycetales* is their ability to produce a wide variety of secondary metabolites, including many antibiotics, which are produced in temporal relation to the onset of morphological differentiation in surface-grown cultures (reviewed in Chater, 1989). The molecular processes regulating the events that lead to differentiation of *Streptomyces* are still largely unclear.

Most *streptomycetes* only sporulate on solid media, while growth in a liquid culture is restricted to the formation of a vegetative mycelium. This typically develops into an intricate network of hyphae, among others resulting in pellet formation, with only the most outwardly oriented sections showing high physiological activity, resulting in reduced growth rate and low yield of the desired product per unit of biomass. Furthermore, because of their filamentous morphology, high density fermentations of biotechnologically interesting *streptomycetes* often are highly viscous, resulting in a low biomass accumulation due to, for instance, aeration and mixing problems.

From this perspective, it is desirable that fragmentation of the mycelium in submerged cultures is stimulated, that branching of the mycelium is reduced, and that in general, the viscosity of the culture is reduced. The role and function of SsgA (SEQ ID NO:11) in the control of the morphology of actinomycetes have been disclosed in van Wezel et al. 2000 bcd and Kawamoto et al. 1997. However, so far no correlation has been made between the morphology of submerged cultures and enzyme or antibiotic formation in fermentations.

The choice of carbon source also has a major impact on morphological and physiological differentiation, as well as on morphology in liquid-grown cultures. In bacteria, the preferential use of readily metabolizable carbon sources is controlled via carbon catabolite repression (CCR), a mechanism well studied in *Bacillus subtilis* and in *Escherichia coli*. In both bacteria the phosphoenolpyruvate-dependent phosphotransferase system (PTS) plays a dominant role, controlling carbon utilization operons by specific (LacI, GalR) and pleiotropic regulators (CytR, CcpA). While *Streptomyces coelicolor* also has a PTS, its role is unclear (Parche et al., 1999; Butler et al., 1999).

Glucose kinase (Glk) is the key control point of CCR in *S. coelicolor* (Angell et al., 1992, 1994); glkA mutants are unable to grow on glucose and are deregulated in glucose repression of catabolite-controlled genes (Angell et al., 1992). Interestingly, introduction of the corresponding gene from *Zymomonas mobilis* resulted in restoration of glucose utilization, but failed to restore CCR (Angell et al., 1994). This suggests that CCR is mediated by glucose kinase through a regulatory site that is different from the catalytic site. Interaction with the PTS seems unlikely, as the system failed to phosphorylate Glk in vitro (Mahr et al., 2000). Due to the lack of a DNA-binding motif, Glk has been proposed to interact with transcription factors, such as GylR and MalR, which are responsible for both specific and global catabolite control of the glycerol and maltose regulons, respectively (Hindle et al., 1994; van Wezel et al., 1997).

There is also a logical link between CCR and *Streptomyces* development; the main signal for the initiation of aerial hyphae formation is nutrient depletion, suggesting a strong link between carbon metabolism and *Streptomyces* development. Indeed, many *streptomycetes* show relatively poor sporulation when grown on glucose-containing solid media, as compared to when mannitol or maltose is used as sole carbon sources. Also, submerged sporulation by *Streptomyces griseus* is repressed by glucose, as are several genes involved in aerial mycelium formation (van Wezel, unpublished data).

Although it is clear that the morphology of filamentous microorganisms is important from a biotechnological perspective and although there are some indications and leads on how to influence the morphology of filamentous microorganism, there is in general a need for tools to influence the morphology in general and, more specifically, a clear need for alternative approaches for obtaining enhanced fragmentation of the mycelium, in preferably submerged cultures, that branching of the mycelium is reduced and that the viscosity of high-density fermentation broths is reduced.

SUMMARY OF THE INVENTION

The invention discloses important findings, which relate to the morphology of filamentous microorganisms, and the effects of carbon feeds on morphology, growth, and production of the desired product. More specifically, they relate to the effects of the presence and the activity of ssgA-like genes, and to the fact that these morphogenes are under the control of catabolite repression. Based on these findings the invention provides multiple applications that are outlined below.

The present invention discloses a method for improving the production of a product of interest in a liquid culture of filamentous microorganisms comprising providing filamentous microorganisms with an agent for altering the morphology of microstructures of filamentous microorganisms.

In a preferred embodiment, the invention provides a method for improving the production of a product of interest in a liquid culture of filamentous microorganisms comprising providing filamentous microorganisms with an agent for altering the morphology of microstructures of filamentous microorganisms, wherein the agent comprises a gene encoding SsgB (SEQ ID NO:9) and/or SsgC (SEQ ID NO:15) and/or SsgD (SEQ ID NO:13) and/or SsgE (SEQ ID NO:14) and/or SsgF (SEQ ID NO:12) and/or SsgG (SEQ ID NO:10) and/or a functional equivalent and/or a functional fragment of any of these. In an even more preferred embodiment, the agent comprises a gene encoding SsgB (SEQ ID NO:9) and/or SsgC (SEQ ID NO:15) and/or a functional equivalent and/or a functional fragment of any of these.

It is also disclosed in the experimental part that the morphology of microstructures of filamentous microorganisms is influenced by the presence or absence of endogenous ssg genes. In another preferred embodiment, the invention therefore provides a method for improving the production of a product of interest in a liquid culture of filamentous microorganisms comprising altering in filamentous microorganisms the expression level or copy number of an endogenous agent for altering the morphology of microstructures of filamentous microorganisms, wherein the endogenous agent comprises a gene encoding SsgB (SEQ ID NO:9) and/or SsgC (SEQ ID NO:15) and/or SsgD (SEQ ID NO:13) and/or SsgE (SEQ ID NO:14) and/or SsgF (SEQ ID NO:12) and/or SsgG (SEQ ID NO:10) and/or a functional equivalent and/or a functional fragment of any of these. In an even more preferred embodiment, the agent comprises a gene encoding SsgB (SEQ ID NO:9) and/or SsgC (SEQ ID NO:15) and/or a functional equivalent and/or a functional fragment of any of these.

The methods of the invention are not only used to improve the production of a product of interest but they are also used for influencing (for example, improving) growth of filamentous microorganisms, influencing (for example, enhancing) fragmentation, influencing (for example, reducing) branching or influencing (for example, decreasing) viscosity.

A product of interest is, for example, an endogenous product of filamentous microorganisms or a product which is obtained via introduction of genetic information (for example, DNA or RNA) encoding the product of interest. A typical example of an endogenous product of interest is a secondary metabolite, for example, an antibiotic or an antitumor agent. Other examples of useful products are hypocholesterolemic agents, enzyme inhibitors, antimigraine agents, herbicides, antiparasitic agents, ruminant growth promoters, bioinsecticides, receptor (ant)agonists, heterologous proteins or even simple biomass.

In the case of *streptomycetes* such a product of interest is typically an antibiotic or an enzyme.

A "filamentous microorganism" is typically defined as a microorganism whose life cycle includes at least one stage of mycelial growth. The mycelium may be entirely within the substratum; such a mycelium is termed substrate mycelium. However, there are also filamentous microorganisms which form in addition a structurally distinct aerial mycelium which typically extends away from the substratum. In such organisms, spores, if they occur, are formed at the tips of the aerial mycelium, resulting in single (monospora), double (bispora), or multiple spores, or are formed in a body designated sporangium. Examples of filamentous bacteria are *Actinomyces, Actinoplanes, Amycolatopsis, Frankia, Microbispora, Micromonospora, Nocardia, Planobispora, Streptomyces, Streptoverticillium, Thermobifido*, but also filamentous fungi, such as *Aspergillus, Penicillium*, and *Candida*.

The *Streptomyces coelicolor* genome has been completely sequenced and annotated on the basis of obvious homologies to known genes. In total five *S. coelicolor* genes were formally annotated as ssgA or ssgA-like. The present invention discloses that *Streptomyces coelicolor* M145 harbors in total seven genes that encode members of the family of SsgA-like proteins (designated SsgA-SsgG, SEQ ID NOS:11, 9, 15, 13, 14, 12, and 10, respectively), and it is likely that they all have (different) effects on *Streptomyces* morphology. Examples of genes which belong to the ssgA-like gene family are ssgB, ssgC, ssgD, ssgE, ssgF and ssgG. A pileup of all the SsgA-like proteins is shown in FIG. 7. The genes encode relatively small proteins (130-140 aa), which share between 30-50% amino acid identity. The corresponding proteins (that show relevant similarity to SsgA (SEQ ID NO:11)) are designated SALPs (SsgA-like proteins). Although the SALP show amino acid similarity, they surprisingly can provide different effects with respect to the morphology of filamentous microorganisms (as disclosed herein within the experimental part).

As disclosed herein within the experimental part, SsgC (SEQ ID NO:15) has a similar morphological effect as SsgA (SEQ ID NO:11), but somewhat less severe. The ssgC gene is functionally related to the ssgA gene as it can (partly) restore development to an ssgA mutant. Hence, by providing a gene encoding SsgC (SEQ ID NO:15) to a filamentous microorganism, reduced branching and/or enhanced fragmentation and/or reduced viscosity is obtained and the production of the product of interest is improved. It is clear for a person skilled in the art that the effect of SsgC (SEQ ID NO:15) can also be combined with the effect of SsgA (SEQ ID NO:11) or any of the other SALPs.

It is also disclosed herein that ssgB inhibits sporulation, but not aerial mycelium formation, on plates when expressed at high level. However, the ssgB gene is not functionally related to the ssgA gene, as it fails to restore a significant degree of sporulation to the ssgA mutant when the mutant is complemented by multiple copies of ssgB. Also, an ssgB mutant forms unusually large colonies. Therefore, ssgB is also a morphogene which has pleiotropic—but different—effects on mycelial morphology. However, when SsgB (SEQ ID NO:9) is (over) expressed in, for example, liquid *Streptomyces* cultures the following observations are made: more synchronous growth, smaller pellets and enhanced fragmentation. Hence, the invention also provides a method for improving the synchronization of a liquid culture of filamentous microorganisms comprising providing filamentous microorganisms with a gene encoding SsgB (SEQ ID NO:9) or by increasing the endogenous expression of SsgB (SEQ ID NO:9) (for example, by modifying the promoter in front of the gene encoding SsgB (SEQ ID NO:9)).

It is furthermore disclosed that overexpression of ssgD has an almost opposite effect as overexpression of the developmentally regulated genes ssgA, ssgB and ssgC, thereby restricting hyphal tip extension rate and, on solid media, reducing colony size.

Overexpression of ssgF completely blocked sporulation of *S. coelicolor*. It is therefore likely that SsgF (SEQ ID NO:12) plays a morphogenic role during development, and especially when nutrients become limited, such as in late-exponential liquid-grown cultures, and especially also in the later phase of batch fermentations.

A study on the presence of the genes encoding SALP, has revealed the following interesting observation: the genes encoding SsgA (SEQ ID NO:11), B (SEQ ID NO:9), D (SEQ ID NO:13) and E (SEQ ID NO:14) are present in many filamentous microorganisms and are often conserved. The ssgA gene is present in many if not all *streptomycetes*, and has been identified in *S. coelicolor, S. griseus, S. avermitilis, S. netropsis, S. albus*, and *S. goldeniensis*, while we have so far identified ssgB in *S. coelicolor, S. griseus*, and *Thermobifido fusca*. Southern hybridization data show that ssgD and ssgE are also present in many actinomycetes, such as *Streptoverticillium netropsis, S. fradiae, S. lividans, Saccharopolyspora erythraea, S. coelicolor, S. griseus*, and *S. cinnamoneus*.

Moreover, it is concluded that the copy number of these genes plays an important role in respect to the morphology of filamentous microorganisms and hence in the production of a "product of interest." For example, a deletion mutant of ssgB, where the copy number is by definition zero, results (on solid media) in enhanced growth and increased antibiotic production. Addition of ssgB to a wild-type filamentous microorganism resulted (in liquid media) in enhanced fragmentation, smaller pellets and more synchronized growth. Hence, the invention does not only provide a method for improving the production of a product of interest in a culture of filamentous microorganisms comprising providing the microorganisms with an agent for altering the morphology of microstructures of the microorganism, but also a method for improving the production of a product of interest in a culture of filamentous microorganisms comprising modifying an endogenous ssg gene in the microorganisms resulting in the presence of a non-functional ssg gene. A "non-functional ssg gene" is herein defined as an ssg gene that is not capable to perform its original function at all or an ssg gene that is impaired in such a way that its original function cannot be performed efficiently. An example of a non-functional ssg gene is a knock-out ssg gene. It is clear for a person skilled in the art that instead of modifying the endogenous gene, the same effect is also obtained by impairing the promoter in front of the gene such that no or hardly any transcript (and hence no or hardly any protein) is produced. Mutating or deleting essential elements from the promoter, for example, accomplishes this.

It is clear from the results as described herein that these ssgA-like genes are capable of improving the production of a product of interest by altering the morphology (preferably by enhancing fragmentation and/or reducing branching and/or enhancing tip extension rate) of microstructures of filamentous microorganisms.

A "functional equivalent" and/or a "functional fragment" thereof is herein defined as an equivalent and/or a fragment which is capable of performing the same activity, but possibly in different amounts (similar in kind, but not necessarily in amount). A functional equivalent is, for example, an SsgB-like protein encoded by a gene from another organism. Another example of a functional equivalent is, for example, obtained by domain swapping between different SsgA-like proteins. For example, the N-terminal part of SsgB (SEQ ID NO:9) is functionally combined with the C-terminal part of SsgA (SEQ ID NO:11). Examples of combined SsgA-like proteins can be found in the experimental part herein and in FIG. 9. However, a functional equivalent is also obtained by using techniques like gene shuffling and site-directed PCR-mediated mutagenesis. A functional fragment is, for example, an N-terminal, C-terminal or internal part of SsgB (SEQ ID NO:9) or SsgC (SEQ ID NO:15). As outlined hereunder, a functional equivalent and/or functional fragment is also defined by the presence of a certain domain or the presence of multiple domains. The terms "domain" and "signature" are used interchangeably herein.

The term "protein-like activity" (for example, SsgC-like activity) is functionally defined herein as the ability to enhance septation and/or enhance fragmentation and/or reduce branching and/or improve synchronization in (typically) submerged cultures of filamentous microorganisms.

The effect of the mentioned agent on the morphology of microstructures of the filamentous microorganism is easily determined by microscopic analysis, like phase-contrast microscopy or scanning electron microscopy. Morphological characteristics that are of particular interest (for large scale cultures or industrial scale fermentations) are the amount of fragmentation, the amount of branching and the viscosity induced by the microstructures.

In a preferred embodiment, the invention provides a method for improving the production of a product of interest in a liquid culture of filamentous microorganisms wherein the agent comprises a gene encoding SsgB (SEQ ID NO:9) and/or SsgC (SEQ ID NO:15) and/or SsgD (SEQ ID NO:13) and/or SsgE (SEQ ID NO:14) and/or SsgF (SEQ ID NO:12) and/or SsgG (SEQ ID NO:10) and/or a functional equivalent and/or a functional fragment of any of these, wherein the functional equivalent and/or a functional fragment comprises at least one of the signatures A (SEQ ID NO:1) or B (SEQ ID NO:2) or at least one and preferably both of the signatures A (SEQ ID NO:1) and C (SEQ ID NO:3), and wherein:

signature A = (SEQ ID NO: 1)
[IV][PL][[AV]X[FL]XY[DEH]X(2,3)[DH]P;

signature B = (SEQ ID NO: 2)
WX[FVL]XR[ED][LM][LV]XXG;

signature C = (SEQ ID NO: 3)
WX[FVL]XR[ED][LM][LV]XXG X(5)GXG[DE]V;

and wherein:
[IV]=I or V in that position
X=any amino acid
X(2,3)=2 or 3 of any amino acid Signatures A (SEQ ID NO:1) and C (SEQ ID NO:3) exclusively identified all SsgA-like sequences, while signature B (SEQ ID NO:2) also detected a few other protein sequences, including putative morpho-proteins. Proteins identified with help of the above-identified signatures are used in a method for improving the production of a product of interest in a liquid culture of filamentous microorganisms.

In another preferred embodiment, the invention provides a method for improving the production of a product of interest in a liquid culture of filamentous microorganisms comprising providing the filamentous microorganisms with an agent for altering the morphology of microstructures of filamentous microorganisms according to the invention, wherein the agent comprises a gene encoding SsgR or a functional equivalent and/or a functional fragment thereof and optionally providing the microorganisms with an ssgA promoter-like DNA sequence operatively linked to the coding sequence of SsgA (SEQ ID NO:11) and/or SsgB (SEQ ID NO:9) and/or SsgC (SEQ ID NO:15) and/or SsgD (SEQ ID NO:13) or a functional equivalent and/or a functional fragment of any of these.

An "ssgA-promoter-like DNA sequence" is herein defined as a DNA sequence that comprises the functional elements of an ssgA promoter. Besides the promoter sequences, an additional region of at least 150 bp and maximally 500 bp is required for binding and therefore activation by SsgR. Omission of these sequences on expression constructs reduces the activity of the ssgA promoter sequences to levels such that the resulting transcript levels drop below the detection limit. Comparison of the ssgA promoter regions of S. coelicolor and S. griseus revealed consensus sequences important for promoter activity and/or SsgR binding (FIG. 4C). Members of the family of IclR-type regulatory proteins are inactivated on binding of a substrate, often a metabolic compound. Altering the DNA binding specificity or substrate binding pocket alters the regulation of ssgA.

As disclosed herein within the experimental part, an ssgR mutant is restored to wild-type by addition of ssgA, but only if ssgA is transcribed from a constitutive promoter (for example, the ermE promoter). This shows that (i) ssgA can restore an ssgR mutant to wild type and (ii) that the endogenous ssgA promoter is dependent on SsgR. The latter is confirmed by S1 mapping experiments. Hence, ssgA expression is regulated by SsgR. The addition of ssgR to a filamentous microorganism that already contains an (endogenous) ssgA-promoter-like DNA sequence operatively linked to the coding region of SsgA (SEQ ID NO:11) and/or SsgB (SEQ ID NO:9) and/or SsgC (SEQ ID NO:15) and/or SsgD (SEQ ID NO:13) or a functional equivalent and/or a functional fragment of any of these, results in expression of one or more of the latter mentioned SsgA-like proteins, which expression results in reduced branching and/or enhanced fragmentation and/or reduced viscosity and/or improved synchronization is obtained and hence the production of the product of interest is improved.

Carbon catabolite repression (CCR) fully depends on the presence of an active glucose kinase. The metabolic function of glucose kinase is to perform the first step in glycolysis, i.e., converting glucose to glucose-6-phosphate. Analyzing glucose kinase activity, it is herein shown that while the protein is expressed constitutively, its activity corresponds to the emergence of a second and third protein band migrating with slightly faster rates than the major Glk protein band. These are considered to be modified versions of the protein, and these modifications are considered crucial for its activity. It is most likely that modification of Glk takes place in a glucose import-dependent manner. That means that glucose kinase is present, but becomes modified and thus activated when Glucose is imported. This finding finally explains one of the longest standing debates in *Streptomyces* molecular biology, namely how Glk can exert both glucose repression and its catalytic activity (converting glucose to glucose-6-phosphate). Both functions are united in the protein itself, and not through carbon fluxes, since replacing Glk by another glucose kinase, e.g. from *Zymomonas mobilis*, does restore glycolysis and hence glucose utilization, but not CCR (Angell et al., 1994).

As disclosed herein, the morphogenes ssgA, ssgB and ssgC play a crucial role in determining growth behavior and the degree of pellet formation, by influencing growth rate, branching, elongation and/or fragmentation. It is furthermore disclosed that these genes, as well as ssgE, ssgF and ssgG, but not ssgD, are under carbon catabolite repression.

This shows that the presence of glucose will repress these genes, resulting in unfavorable growth and morphology in submerged cultures, and morphological differentiation on solid media.

Therefore, in yet another preferred embodiment, the invention provides a method for improving the production of a product of interest in a liquid culture of filamentous microorganisms comprising providing filamentous microorganisms with an agent for altering the morphology of microstructures of filamentous microorganisms, wherein the agent comprises a non-repressive carbon source, meaning a source other than a source of glucose or other high-energy carbon sources (like citrate, fructose and glutamate) that leads to carbon catabolite control, for example, as analyzed in Kwakman et al. (1994). The non-repressive carbon source does not negatively influence the expression of ssgA and/or ssgB and/or ssgC and hence expression of these genes results in reduced branching and/or enhanced fragmentation and/or reduced viscosity is obtained and the production of the product of interest is improved.

In a further embodiment, the invention provides a method for improving the production of a product of interest in a liquid culture of filamentous microorganisms according to the invention, wherein the agent, other than a source of glucose or other high-energy carbon sources, is a C5 carbon source, preferably arabinose or rhamnose or wherein the agent is a combined carbon source of glucose and a C5 carbon source, preferably arabinose or rhamnose. Hence, individual C5 carbon sources as well as combinations do not repress expression of ssgA and/or ssgB and/or ssgC and hence expression of these genes results in reduced branching and/or enhanced fragmentation and/or reduced viscosity compared to when glucose is used as carbon source, resulting in improved production of the product of interest.

As outlined above, a method according to the invention can be applied for improving the production of a product of interest in a liquid culture of filamentous microorganisms. Preferably, the filamentous microorganisms are actinomycetes and even more preferably, the filamentous microorganisms are *streptomycetes*. Applying the method for improving the production of a product of interest to actinomycetes, or more preferably to *streptomycetes* is particularly advantageous because these microorganisms produce a wide variety of secondary metabolites, for example, antibiotics, as well as many industrially relevant enzymes, and hence the production of these antibiotics and/or enzymes are improved. Furthermore, these organisms are capable of providing expression of genes with a high GC-content which are difficult to express in other microorganisms.

Preferably, the genes have a GC-content of above 60% (for example, genes derived from actinomycetes) or the genes have a GC-content of above 70% (for example, genes derived from *streptomycetes*). Typical examples of such genes are glucose isomerase, amylases, glucosidases and cellulases.

Preferably, a method according to the invention is applied to improve expression of a product of interest in a liquid culture. Even more preferably, the liquid culture is a large-scale liquid culture. The use of large-scale liquid cultures enables large-scale production of the product of interest. Typical volumes of large-scale cultures or industrial fermentations are between 20-200 m$^3$.

In yet another embodiment, the invention provides a product of interest obtained according to a method of the invention by harvesting the product of interest from the culture. For ease of production it is preferred that the product of interest is secreted by the filamentous microorganisms. The product of interest which production is improved, may very well be a product (for example, a protein) involved in a pathway of making a useful product such as an antibiotic, so that this production can be further improved on top of the improvement by the enhanced fragmentation etc.

By applying a method according to the invention the amount of produced "product of interest" is dramatically increased (see, for example, FIGS. 1 and 2). Moreover, a method according to the invention also results in an increased (specific) growth rate and hence the fermentation time can be drastically reduced. Hence, the invention also provides a method for decreasing the fermentation time of large scale or industrial fermentation of filamentous microorganisms comprising providing the microorganisms with any one of the herein described agents that is capable of altering the morphology of microstructures of the filamentous microorganisms. It is furthermore disclosed that the *Streptomyces* strain *S. coelicolor*, which was, due to its growth problems, never considered suitable for large scale fermentations, may now be altered according to a method of the invention and is now suitable for large scale fermentations.

Besides a method for improving the production of a product of interest in a liquid culture of filamentous microorganisms, the invention also provides multiple methods for obtaining a filamentous microorganism with altered, preferably enhanced, fragmentation characteristics.

In one of these embodiments, the invention provides a method for obtaining a filamentous microorganism with altered fragmentation and/or branching characteristics during growth comprising altering the expression profile in the microorganism of SsgB (SEQ ID NO:9) and/or SsgC (SEQ ID NO:15) or a functional equivalent and/or a functional fragment thereof. It is herein disclosed that these proteins and/or expression of the corresponding genes leads to altered branching and/or altered fragmentation and/or altered viscosity. However, it is clear that also any combination can be made, for example, SsgA (SEQ ID NO:11) in combination with SsgB (SEQ ID NO:9) or SsgC (SEQ ID NO:15).

It is to be understood that all references to the term "expression profiles" or "expression" can include both expression of DNA, RNA as well as expression of a protein.

In a preferred embodiment, the invention provides a method for obtaining a filamentous microorganism with enhanced fragmentation and/or reduced branching characteristics during growth, comprising providing
  an altered timing of expression in the microorganism of SsgB (SEQ ID NO:9) and/or SsgC (SEQ ID NO:15) or a functional equivalent and/or a functional fragment thereof and/or
  enhancing and/or inducing expression in the microorganism of SsgB (SEQ ID NO:9) and/or SsgC (SEQ ID NO:15) or a functional equivalent and/or a functional fragment thereof.

In case a filamentous microorganism comprises endogenous genes encoding SsgB (SEQ ID NO:9) and/or SsgC (SEQ ID NO:15), an altered timing of expression is used for obtaining a microorganism with enhanced fragmentation and/or reduced branching characteristics during growth. This is, for example, accomplished by operatively linking the gene to an inducible promoter. Means and methods for providing these inducible promoters are well known in the art so that there is no need to go into detail. Upon induction of a promoter at the desired time point, the corresponding protein is expressed and hence a filamentous microorganism with enhanced fragmentation and/or reduced branching characteristics is obtained. Mutation of the (endogenous) promoter of the genes encoding SsgB (SEQ ID NO:9) and/or SsgC (SEQ ID NO:15) such that the promoter is not repressed anymore by glucose-kinase-dependent CCR, is another way to obtain a filamentous microorganism with enhanced fragmentation and/or reduced branching characteristics. However, it is also possible to enhance the activity of an (endogenous) SsgB (SEQ ID NO:9) and/or SsgC (SEQ ID NO:15) promoter, for example, by providing the promoter with enhancer fragments. In case the microorganism does not comprise such an ssgB and/or ssgC gene, the microorganism is provided with genetic information comprising these genes, according to means and methods known by a person skilled in the art. As already discussed above it is also possible to decrease the activity of an (endogenous) SsgB (SEQ ID NO:9) and/or SsgC (SEQ ID NO:15) promoter, for example, by deleting essential promoter elements from the promoter.

Preferably, the functional equivalent and/or a functional fragment comprises at least one of the signatures A (SEQ ID NO:1) or B (SEQ ID NO:2) or at least one and preferably both of the signatures A (SEQ ID NO:1) and C (SEQ ID NO:3), and wherein:

```
signature A =                       (SEQ ID NO: 1)
[IV][PL][AV]X[FL]XY[DEH]X(2,3)[DH]P signature B =                       (SEQ ID NO: 2)
WX[FVL]XR[ED][LM][LV]XXG signature C =                       (SEQ ID NO: 3)
WX[FVL]XR[ED][LM][LV]XXGX(5)GXG[DE]V
``` and wherein:
  [IV]=I or V in that position
  X=any amino acid
  X(2,3)=2 or 3 of any amino acid Even more preferably, the functional equivalent and/or a functional fragment can restore wild-type levels of sporulation to the ssgA mutant, and shares at least 65% overall amino acid identity with the SsgA (SEQ ID NO:11) of FIG. 7. This figure discloses a pileup of all SsgA-like proteins of *S. coelicolor* M145.

Yet, even more preferably, SsgB (SEQ ID NO:9) and/or SsgC (SEQ ID NO:15) or a functional equivalent and/or a functional fragment thereof is derived from an actinomycete preferably a *streptomycete*, and even more preferably from *Streptomyces coelicolor*.

Preferably, the expression is obtained by transfecting the microorganism with genetic information comprising ssgB and/or ssgC or a functional equivalent and/or a functional fragment thereof. Means and methods for expressing such genes are well known in the art so that there is no need to go into detail here regarding cloning vectors, expression vectors, (inducible) promoters, enhancers, restriction enzymes, selection markers, etc. For stability of the presence of the gene, in particular for application in large-scale fermentation, it is however preferred that the genetic information is integrated into the genome of the microorganism. However, if stability is not an issue or can be obtained in any other way the genetic information can also be part of an episomal compound.

In a preferred embodiment, the invention provides a method for obtaining a filamentous microorganism with enhanced fragmentation and/or reduced branching characteristics during growth comprising providing:
  an altered timing of expression in the microorganism of SsgB (SEQ ID NO:9) and/or SsgC (SEQ ID NO:15) or a functional equivalent and/or a functional fragment thereof and/or
  enhancing and/or inducing expression in the microorganism of SsgB (SEQ ID NO:9) and/or SsgC (SEQ ID NO:15) or a functional equivalent and/or a functional fragment thereof,
wherein the filamentous microorganism is an actinomycetes, preferably a *streptomycete*.

Even more preferably, the growth is growth in (preferably large-scale) liquid media and the expression is provided during vegetative growth phase of the filamentous microorganism.

In yet another embodiment, the invention provides a method for obtaining a filamentous microorganism with enhanced fragmentation and/or reduced branching during growth comprising providing:

an altered timing of expression in the microorganism of SsgR or a functional equivalent and/or a functional fragment thereof and/or enhancing and/or inducing expression in the microorganism of SsgR or a functional equivalent and/or a functional fragment thereof and optionally providing the microorganism with an ssgA-promoter-like DNA sequence operatively linked to the coding sequence of ssgA and/or ssgB and/or ssgC or a functional equivalent and/or a functional fragment of any of these. In case a filamentous microorganism comprises (sufficiently expressed) ssgR and an ssgA-promoter-like DNA sequence operatively linked to the DNA sequence encoding SsgA (SEQ ID NO:11) and/or SsgB (SEQ ID NO:9) and/or SsgC (SEQ ID NO:15) or a functional equivalent and/or a functional fragment of any of these, an altered timing of expression of SsgR is used for obtaining a microorganism with enhanced fragmentation characteristics during growth. The SsgR protein induces, via an ssgA-promoter-like DNA sequence, expression of SsgA (SEQ ID NO:11) and/or SsgB (SEQ ID NO:9) and/or SsgC (SEQ ID NO:15) or a functional equivalent and/or a functional fragment of any of these and hence a microorganism with enhanced fragmentation characteristics is obtained. Timing of expression of SsgR is, for example, obtained by providing the microorganism with an expression vector that encodes a protein which is capable of inducing/stimulating SsgR expression. Preferably, an inducible promoter is provided to control the expression. In the case where a microorganism does not comprise (sufficiently expressed) ssgR or a functional equivalent and/or a functional fragment thereof and also does not comprise an ssgA-promoter-like DNA sequence operatively linked to the DNA sequence encoding SsgA (SEQ ID NO:11) and/or SsgB (SEQ ID NO:9) and/or SsgC (SEQ ID NO:15) and/or SsgD (SEQ ID NO:13) or a functional equivalent and/or a functional fragment of any of these, all of these components are provided to the microorganism according to methods known by a person skilled in the art. It is also possible to mutate the SsgR protein itself such that it is capable of, for example, constitutively enhancing SsgA (SEQ ID NO:11) protein production.

Preferably, the DNA fragment encoding SsgR or a functional equivalent and/or a functional fragment thereof is derived from an actinomycete preferably of *streptomycete*, and even more preferably from *Streptomyces coelicolor*.

Preferably, the expression is obtained by transfecting the microorganism with genetic information (for example, DNA or RNA) comprising ssgR or a functional equivalent and/or a functional fragment thereof and optionally providing the microorganism with genetic information comprising an ssgA-promoter-like DNA sequence operatively linked to the DNA sequence encoding SsgA (SEQ ID NO:11) and/or SsgB (SEQ ID NO:9) and/or SsgC (SEQ ID NO:15) or a functional equivalent and/or a functional fragment of any of these. The genetic information is either part of an episomal compound or more preferably, integrated into the genome of the microorganism. An episomal compound is, for example, an episomal construct, plasmid or any other carrier which is not incorporated into the genome of the microorganism.

Expression of endogenous SsgR or a functional equivalent and/or a functional fragment thereof is, for example, obtained by enhancing the activity of an endogenous ssgR promoter. Methods and means for producing such mutated promoters are well known to a person skilled in the art, and such promoters are, for example, obtained by screening of a library containing mutated promoters operatively linked to a detectable product (for example, an enzyme).

Preferably, the invention provides a method for obtaining a filamentous microorganism with enhanced fragmentation and/or reduced branching characteristics during growth comprising providing:

an altered timing of expression in the microorganism of SsgR or a functional equivalent and/or a functional fragment thereof and/or enhancing and/or inducing expression in the microorganism of SsgR or a functional equivalent and/or a functional fragment thereof and optionally providing the microorganism with an ssgA-promoter-like DNA sequence operatively linked to the DNA sequence encoding SsgA (SEQ ID NO:11) and/or SsgB (SEQ ID NO:9) and/or SsgC (SEQ ID NO:15) or a functional equivalent and/or a functional fragment of any of these, wherein the filamentous microorganism is an actinomycetes, preferably a *streptomycete*. Even more preferably, the growth is growth in (preferably large-scale) liquid media and the expression is provided during vegetative growth phase of the filamentous microorganism.

In yet another embodiment, the invention provides a method for obtaining a filamentous microorganism with altered fragmentation and/or branching characteristics during growth comprising modulating the sensitivity of an ssgA-like gene in the microorganism to carbon catabolite repression. Preferably, the invention provides a method for obtaining a filamentous microorganism with enhanced fragmentation characteristics during growth comprising decreasing the sensitivity of an ssgA-like gene in the microorganism to carbon catabolite repression. Even more preferably, the carbon catabolite repression is induced by glucose and yet even more preferred, the ssgA-like gene is ssgA and/or ssgB and/or ssgC and/or ssgR or a functional equivalent and/or a functional fragment thereof.

As disclosed herein, the morphogenes ssgA, ssgB and ssgC and also ssgR play a crucial role in determining growth behavior and the degree of pellet formation, by influencing growth rate, branching, elongation and fragmentation. We furthermore disclose that these genes, as well as ssgE, ssgF, and ssgG, but not ssgD, are under carbon catabolite control. This implies that the presence of glucose will repress these genes, resulting in unfavorable growth and morphology in submerged cultures, and morphological differentiation on solid media.

Hence, the invention provides a method for obtaining a filamentous microorganism with enhanced fragmentation and/or reduced branching characteristics during growth comprising decreasing the sensitivity of an ssgA-like gene in the microorganism to carbon catabolite repression, wherein the sensitivity is decreased by mutations in the corresponding promoters of ssgA and/or ssgB and/or ssgC and/or ssgR or a functional equivalent and/or a functional fragment thereof. When the (endogenous) promoter of, for example, ssgA is no longer sensitive to the process of carbon catabolite repression, use of glucose as carbon source does not repress the expression of SsgA (SEQ ID NO:11) and hence a filamentous microorganism with enhanced fragmentation and/or reduced branching characteristics is obtained without the use of pure, and therefore expensive, carbon sources.

In the case where it is not desirable to use a genetically modified filamentous microorganism, the use of a non-repressive carbon source, and preferably a C5 carbon source like arabinose or rhamnose, is provided, to avoid catabolite repression of morphogenes such as those encoding SsgA-like proteins. Also the use of a combination of the non-repressive carbon sources, for example, arabinose and rhamnose, can be used, again avoiding catabolite repression of the morphogenes.

It is clear to a person skilled in the art that, based on the information disclosed in the present patent application, for obtaining a filamentous microorganism with enhanced fragmentation and/or reduced branching characteristics; it is also possible to make combinations of the different embodiments disclosed herein. For example, to provide a filamentous microorganism with genetic information encoding SsgB (SEQ ID NO:9) and at the same time use a non-repressive carbon source to prevent carbon catabolite repression of ssgA-like morphogenes.

One of the ultimate goals of the present invention is improving the production of a product of interest in a liquid culture of filamentous microorganisms comprising providing the filamentous microorganisms with an agent for altering the morphology of microstructures of the filamentous microorganisms or improving the production of a product of interest in a liquid culture of filamentous microorganisms comprising altering in the filamentous microorganisms the expression level or copy number of an endogenous agent for altering the morphology of microstructures of the filamentous microorganisms. It is clear that the filamentous microorganisms used in these methods are also part of the invention.

The invention, therefore, provides a filamentous microorganism obtainable by a method according to the invention. For example, by providing the filamentous microorganism with (extra) genetic information encoding SsgB (SEQ ID NO:9) and/or SsgR or by deleting an endogenous SALP. Preferably, the filamentous microorganism is an actinomycetes, preferably a *streptomycete*.

More in general, the invention provides a filamentous microorganism comprising a recombinant and/or mutated ssgB and/or ssgC and/or ssgD and/or ssgE and/or ssgF and/or ssgG and/or ssgR expression cassette. In a preferred embodiment, the invention provides a filamentous microorganism comprising a recombinant and/or mutated ssgB and/or ssgC and/or ssgD and/or ssgE and/or ssgF and/or ssgG and/or ssgR expression cassette that comprises a mutated promoter in operative linkage with the coding region of ssgB and/or ssgC and/or ssgD and/or ssgE and/or ssgF and/or ssgG and/or ssgR. The promoter is, for example, mutated such that the promoter is inducible at a temperature change or is insensitive to carbon catabolite repression or is provided with enhancer elements. In another preferred embodiment, the invention provides a filamentous microorganism comprising a recombinant and/or mutated ssgB and/or ssgC and/or ssgD and/or ssgE and/or ssgF and/or ssgG and/or ssgR expression cassette that comprises a mutated coding region for ssgB and/or ssgC and/or ssgD and/or ssgE and/or ssgF and/or ssgG and/or ssgR. In this way a more active protein (for example, a more active SsgB (SEQ ID NO:9)) is obtained.

Furthermore, the invention provides structures formed in liquid culture by a filamentous microorganism according to the invention. Theoretically the structures in a (large scale) fermentation process should fullfill the following criteria: during initial growth (precultures) the structures should be small (±10-50 µm) to enable the cultures to efficiently utilize nutrients and oxygen, and optimize growth rate. At the beginning of the large culture, fast growth and hence small structures are desired. When sufficient biomass has been obtained the structures preferentially have a size of ±50-150 µm to enable the production of the "product of interest." The structures according to the invention are typically 5- to 10-fold smaller than the pellets formed by microorganisms in which the expression of morphogene(s) has not been altered and/or added. For example, wild-type *S. coelicolor* forms structures of 0.2-1 mm and structures obtained by any one of the methods of the invention are typically 20-100 µm. It is clear for a person skilled in the art that the majority of the structures have the mentioned size but that some of the structures might also be of larger or smaller size. However, overall a reduced size of the structures is obtained.

The present invention also discloses that fragmentation and hence the size of the structures formed by filamentous microorganisms in (large-scale) liquid media, is also strongly affected by the pH. The pH effect is observed for both the wild type strains as well as with the strains that have been provided with an agent for altering the morphology of microstructures (for example, SsgA (SEQ ID NO:11)) of the filamentous microorganisms. In general, the following observations have been made: fragmentation is observed at a ±pH 5.5 or lower and somewhat larger structures (pellets) were formed in cultures buffered at ±pH 6.0 and higher. These observations are very useful for influencing the fragmentation and/or pellet formation of filamentous microorganisms and hence provide an easy way for influencing the growth of filamentous microorganisms. Hence, the invention comprises a method for influencing growth of filamentous microorganism, influencing fragmentation, influencing branching or influencing viscosity comprising influencing the pH. For example, for obtaining a fragmented (pre)culture the pH is adjusted at a ±pH 5.5 or lower (for example, ±pH 5.5) and during the fermentation the pH is buffered around at ±pH 6.0 and higher, preferably ±6.5 to ±7.0. It is clear for a person skilled in the art that the used filamentous microorganism determines the actual upper and lower limits of the pH. Hence, the invention also provides a method for obtaining fragmented growth in liquid cultures of filamentous microorganisms comprising buffering the medium at a ±pH 5.5 or lower. Furthermore, the invention also provides a method for obtaining somewhat larger mycelial structures (pelleted growth) in liquid cultures of filamentous microorganisms comprising buffering the medium at a ±pH 6.0 and higher (for example, pH around ±6.5 to ±7.0).

Hence, the method according to the invention is used in a method for growing filamentous microorganisms in which the pH of the medium is first kept at an acidic pH to obtain large amounts of small(er) structures and later on the pH is adjusted to approximately neutral values to obtain somewhat larger structures, suitable for the production of a product of interest.

The invention also provides a facility for large-scale growth of filamentous microorganisms (for example, a fermentor) comprising the filamentous microorganisms in a suitable buffered (pH) medium in which the pH is first kept at a pH 5.5 or lower and later on adjusted to a pH of 6.0 and higher.

The invention also provides a liquid culture comprising a collection of structures according to the invention or a filamentous microorganism according to the invention. Preferably, the liquid culture is a large-scale liquid culture.

In yet another embodiment, the invention provides a method for producing an antibiotic or a useful protein comprising culturing a filamentous microorganism according to the invention and capable of expressing the antibiotic or the protein and harvesting the antibiotic or protein from the culture.

The invention will be explained in more detail in the following description, which is not limiting the invention.

BRIEF DESCRIPTION OF THE SEVERAL VIEWS OF THE DRAWINGS

FIG. 2A. Growth curves. Strains used were *S. roseosporus* harboring control plasmid pSET152 and the same strain harboring pGWS4-SD (overexpressing ssgA). Fermentations were performed in TS medium (kept at a constant pH of 6.5). Dissolved oxygen tension was set at 80% and adjusted by changing stirrer speed. Points shown in the graph represent samples taken for biomass calculations (dry weight, in g/l) and antibiotic activity assay (FIG. 2BC).

FIGS. 2B and 2C. Antibiotic activity assays of samples shown in FIG. 2A. A lawn of *Streptomyces avermitilis* ATCC31267 was plated on minimal medium agar plates with mannitol as the sole carbon source (1% w/v), and containing 0.5 M $CaCl_2$. Sterile filters were placed onto the plates and 10 μl of filtered supernatant from FIG. 2A was spotted on these filters. Plates were allowed to grow for four days and photographed. Zones of clearing (dark halos) represent growth inhibition due to antibiotics present in the culture fluid of the *S. roseosporus* fermentations.

M145. Wild-type *S. coelicolor*
GSA3. ssgA mutant
GSA4. ssgA mutant complemented by ssgA
GSA5. ssgA mutant (not) complemented by ssgA with internal deletion
GSR1. ssgR in-frame deletion mutant
GSR2. GSR1 complemented by ssgR
GSR3. GSR1 (not) complemented by ssgA with its own promoter
GSR4. GSR1 complemented by ssgA expressed from the SsgR-independent ermE promoter.

Note that ssgA can only restore sporulation to the ssgR mutant if it is expressed from a promoter that is independent of intact SsgR.

Figure 4A:
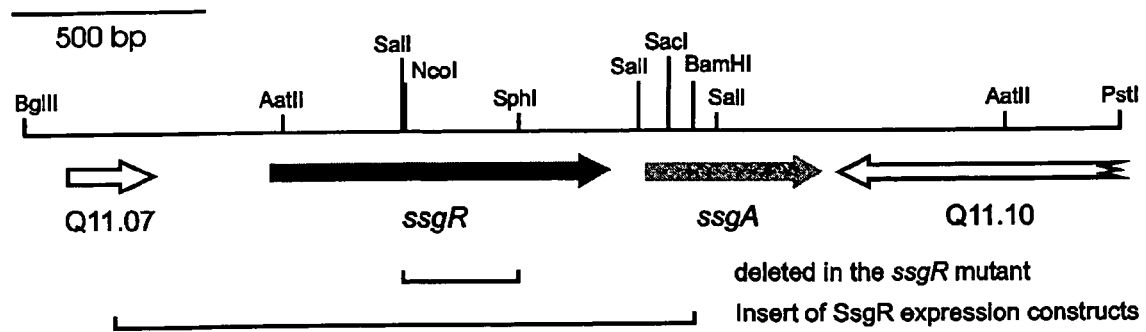

FIG. 4A. Restriction map of the ssgRA operon and flanking sequences.

FIG. 4B. Sequence of the start of ssgA and upstream region, and oligonucleotides and RNA 5' ends. Nucleotide numbering refers to the ssgA translational start site. The complementary sequence is below the coding sequence. The derived amino acid sequences corresponding to the end of ssgR (genbank accession CAB46963) and start of ssgA (genbank accession CAB46964) are shown below the sequence. ♦, RNA 5' end; −10, putative −10 promoter consensus sequence. RBS, Ribosome binding site. Oligonucleotides T7-AF and T7-AR used for generating a probe for S1 mapping are underlined in the sequence.

FIG. 4C. Comparison of the intergenic regions between ssgR and ssgA of *S. coelicolor* (top) and *S. griseus* (bottom). The DNA sequence shown is that of *S. coelicolor*, with nucleotide numbering relative to the ssgA translational start site (+1). Highly conserved sequences are shown in bold face, differences in the *S. griseus* DNA sequence are shown below the sequence. Underlined TGA and ATG sequences represent the translational stop codon of ssgR and the translational start codon of ssgA, respectively. Asterisks indicate approximate transcriptional start sites, as determined by nuclease S1 mapping, −10 indicates possible consensus −10 promoter sequence.

Figure 5:
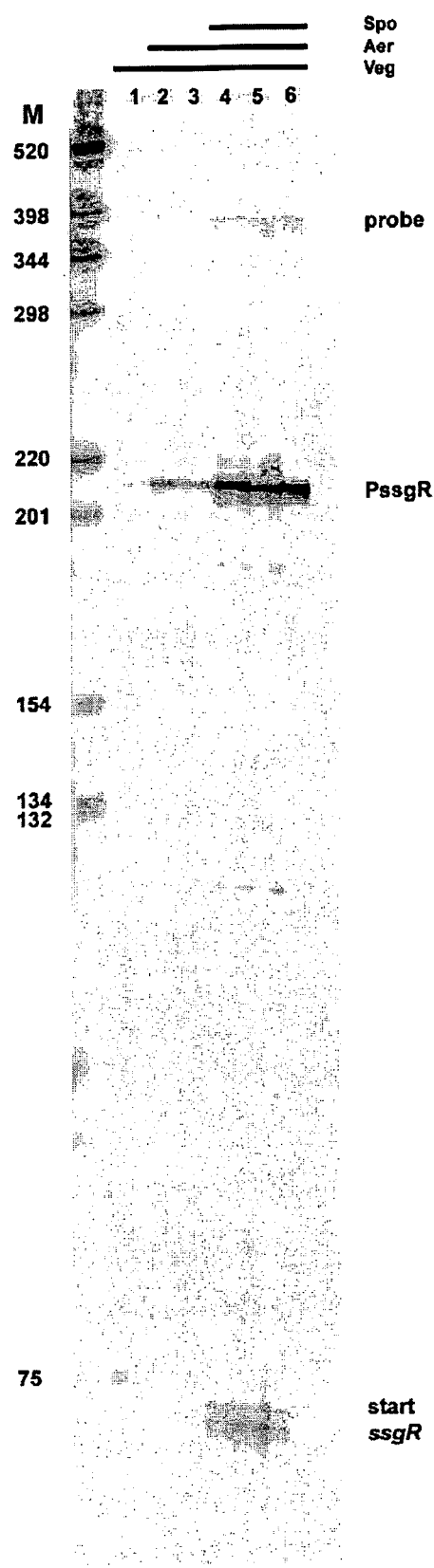

FIG. 5. Transcriptional analysis of *S. coelicolor* ssgR. RNA was isolated from minimal medium (SMMS+mannitol), and analyzed using high resolution transcription analysis. RNA time points: (1) 24 hours, (2) 36 hours, (3) 48 hours, (4) 64 hours, (5) 80 hours, and (6) 96 hours. Sample 2 corresponds to the onset of aerial mycelium formation, and sporulation started after approximately 64 hours (sample 4).

For probe and location of the transcript 5' ends, see text.

While ssgR transcripts were already visible in samples 2 and 3, transcription of ssgR was strongly enhanced as soon as sporulation started. This means that ssgR is transcribed specifically during differentiation.

A second band, with similar growth-phase dependence, corresponds to the start of ssgR. It is unclear if this represents de novo transcription, or processing of the larger transcript.

Figure 6:
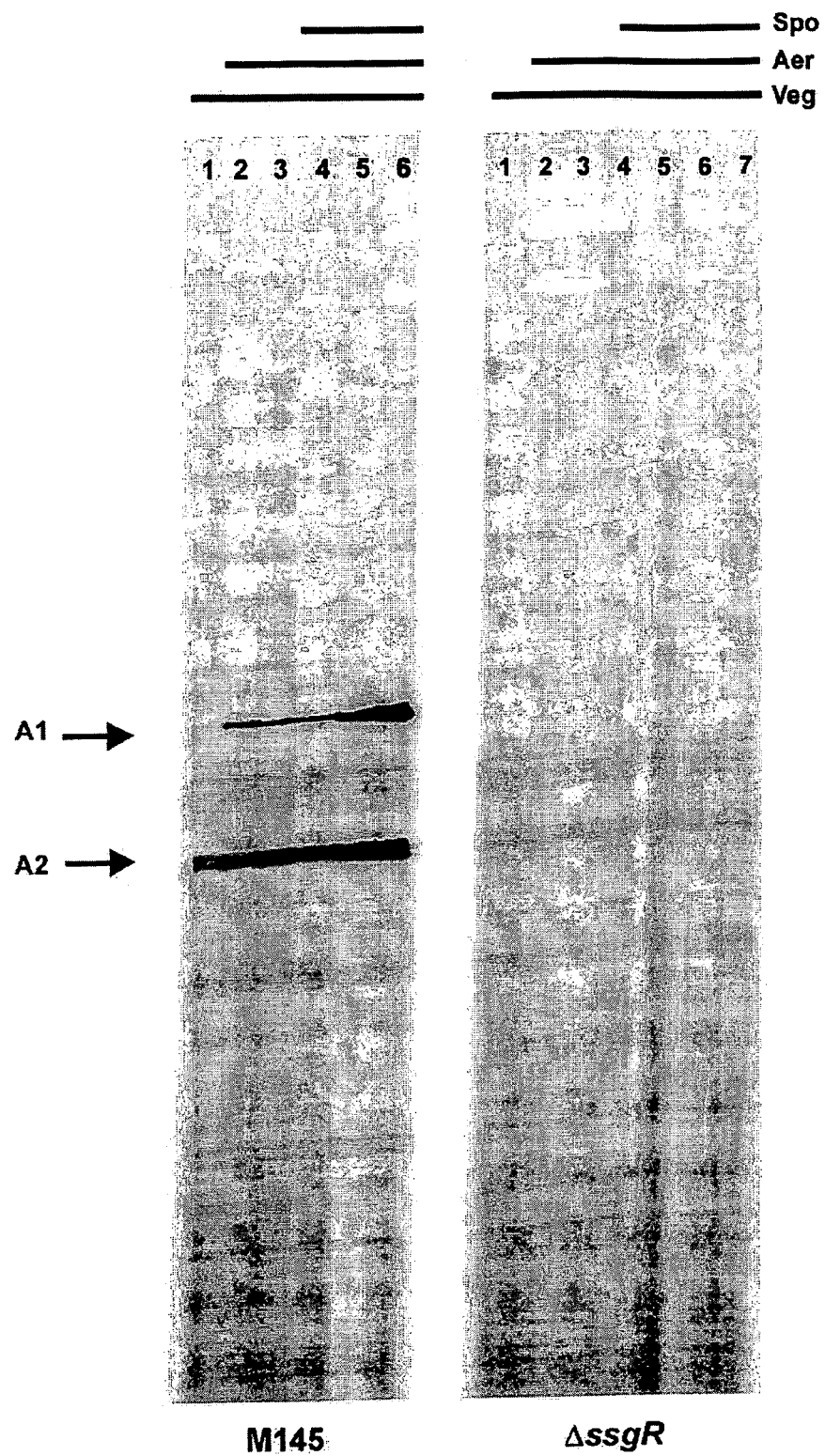

FIG. 6. Transcriptional analysis of *S. coelicolor* ssgA. RNA was isolated from *S. coelicolor* M145 and its ssgR mutant, both grown on minimal medium (SMMS+mannitol), and analyzed by high resolution transcription analysis. RNA time points: (1) 24 hours, (2) 36 hours, (3) 48 hours, (4) 64 hours, (5) 80 hours, (6) 96 hours, and (7) 112 hours. Sample 2 corresponds to the onset of aerial mycelium formation, and sporulation started after approximately 64 hours (sample 4). For probe and location of the transcript 5' ends, see text.

Two transcripts were observed, indicated as A1 and A2. Both bands show growth-phase dependence, and peak when *S. coelicolor* is sporulating. We failed to detect significant levels of ssgA transcripts in the ssgR mutant. Therefore, ssgA transcription is considered completely dependent on intact SsgR.

Figure 7:
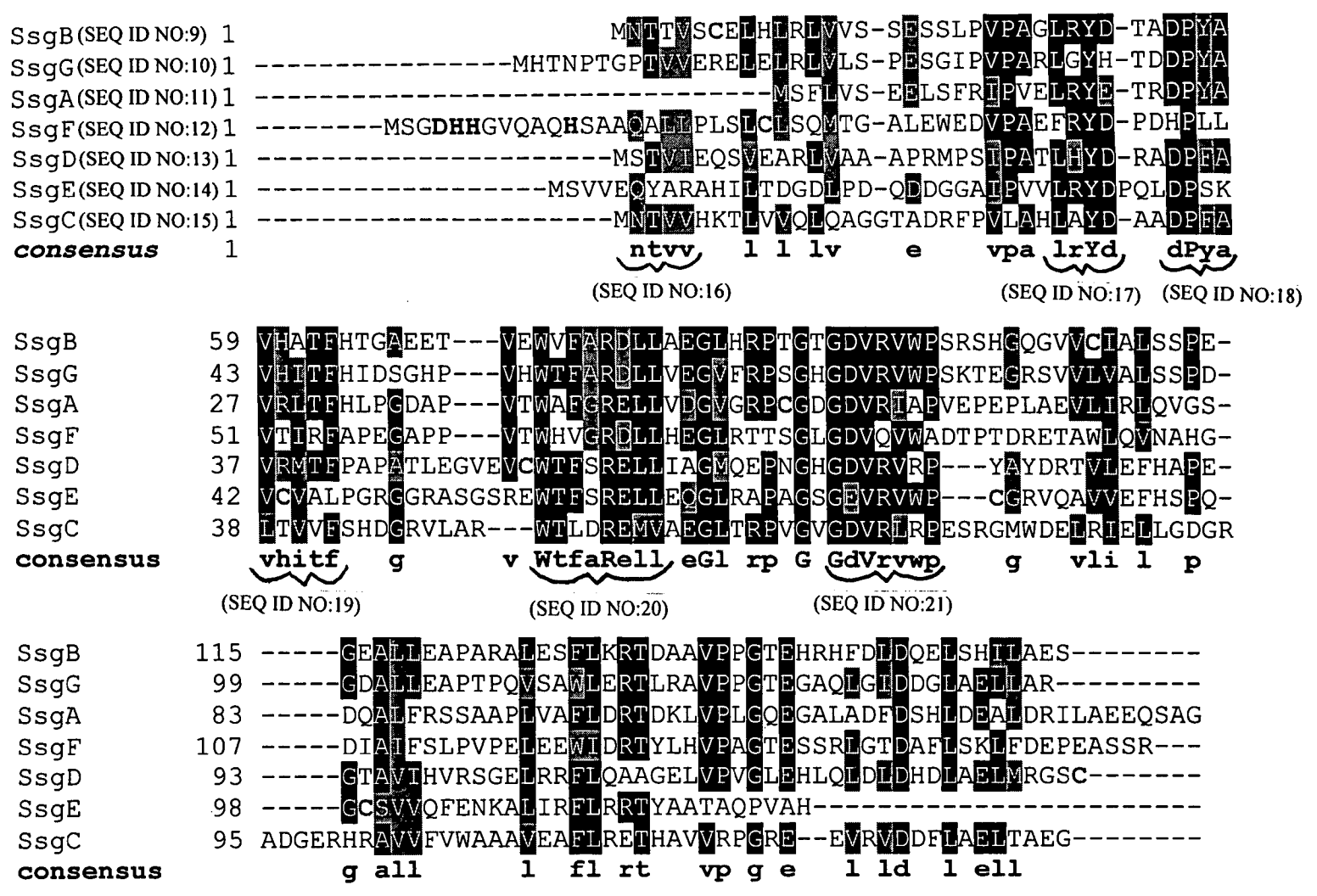

FIG. 7. Comparison of the SsgA-like proteins of *Streptomyces coelicolor* M145. Amino acids that are conserved or similar among at least four homologues are shaded in black or grey, respectively. Purple residues in the consensus sequence are conserved (capitals) or similar (lower case) in all orthologues. Cysteines, which potentially form sulphur-bridges, are shown in green. SsgF (SEQ ID NO:12) has an N-terminal extension relative to the other orthologues, which is a possible transmembrane sequence. Asp (D) and His (H) residues in the SsgF (SEQ ID NO:12) N-terminal extension are shown in blue.

FIGS. 8A through 8F. Restriction maps of the ssgA-like genes ssgB-G, with flanking ORFs and inserts of relevant constructs. The maps shown are (8A) ssgB, (8B) ssgC, (8C) ssgD, (8D) ssgE, (8E) ssgF, (8F) ssgG.

Figure 9A:
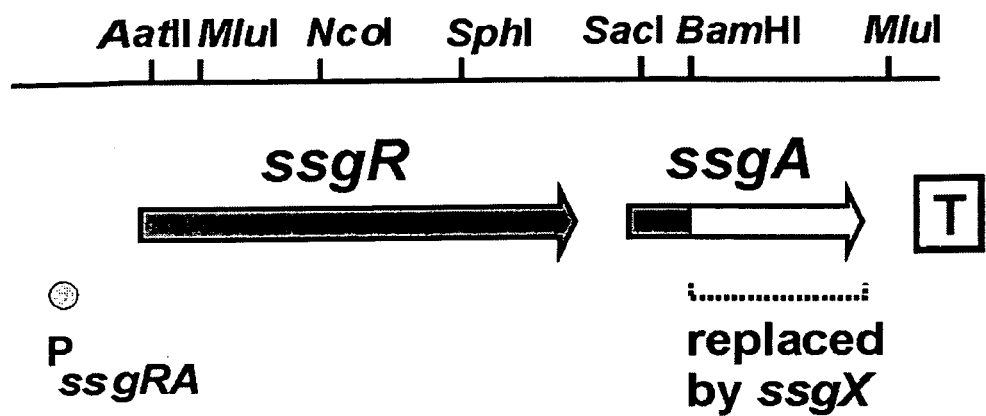
Figure 9B:
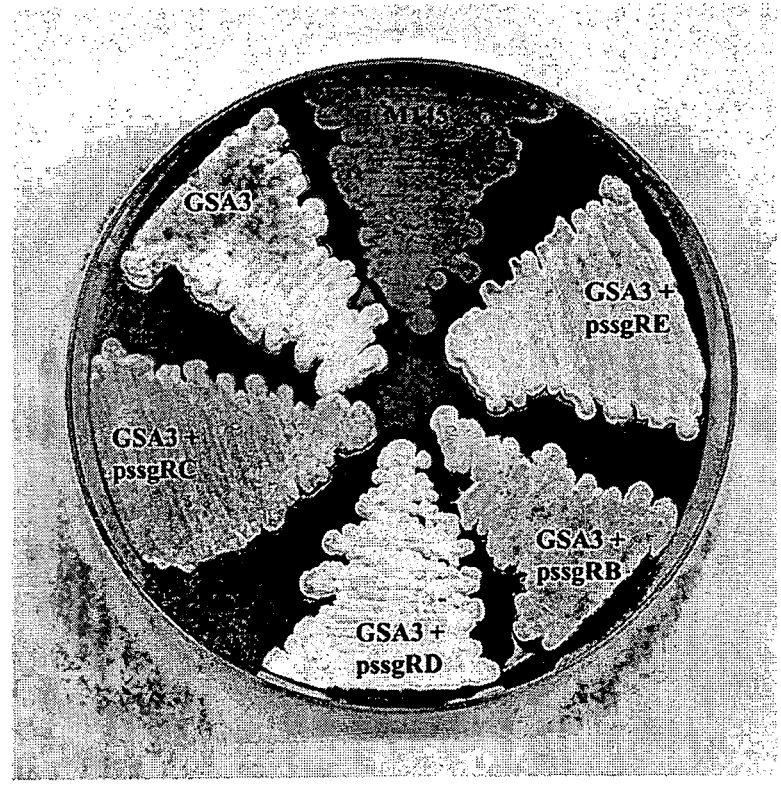

FIGS. 9A through 9B. Complementation of the ssgA mutant by hybrid ssgA-like genes.

FIG. 9A. Schematic representation of hybrid clones. The ssgA gene was replaced by any of the ssgX orthologues, leaving only the first 24 codons of ssgA. The conserved Pro residue (aa position 24 in the SsgA (SEQ ID NO:11) protein) was used to create a BamHI site, allowing creation of the fusions. In this way, the ssgA-like genes are regulated in the same way as ssgA itself.

FIG. 9B. Effect of hybrid clones on sporulation of the ssgA mutant GSA3. Only ssgC restored a significant degree of sporulation to the ssgA mutant, as shown by the grey-pigmented spores. Production of viable spores was verified by phase-contrast microscopy and by heat resistance tests FIG. 10. Analysis of the relative activity and the timing of the ssgX promoters by promoter probing. Transformants of M512 with derivatives of pIJ2587 harboring upstream sequences of the ssgA-like genes, were grown on R2YE. M512 is a mutant of M145 which lacks the activator genes redD and actII-ORF4 for the biosynthesis of the antibiotics RED and ACT, respectively. pIJ2587 is a low-copy number vector that contains the promoterless redD gene. Promoter activity of a DNA fragment placed in front of redD is shown by the appearance of the red-pigmented undecylprodigiosin (RED).

Figure 11:
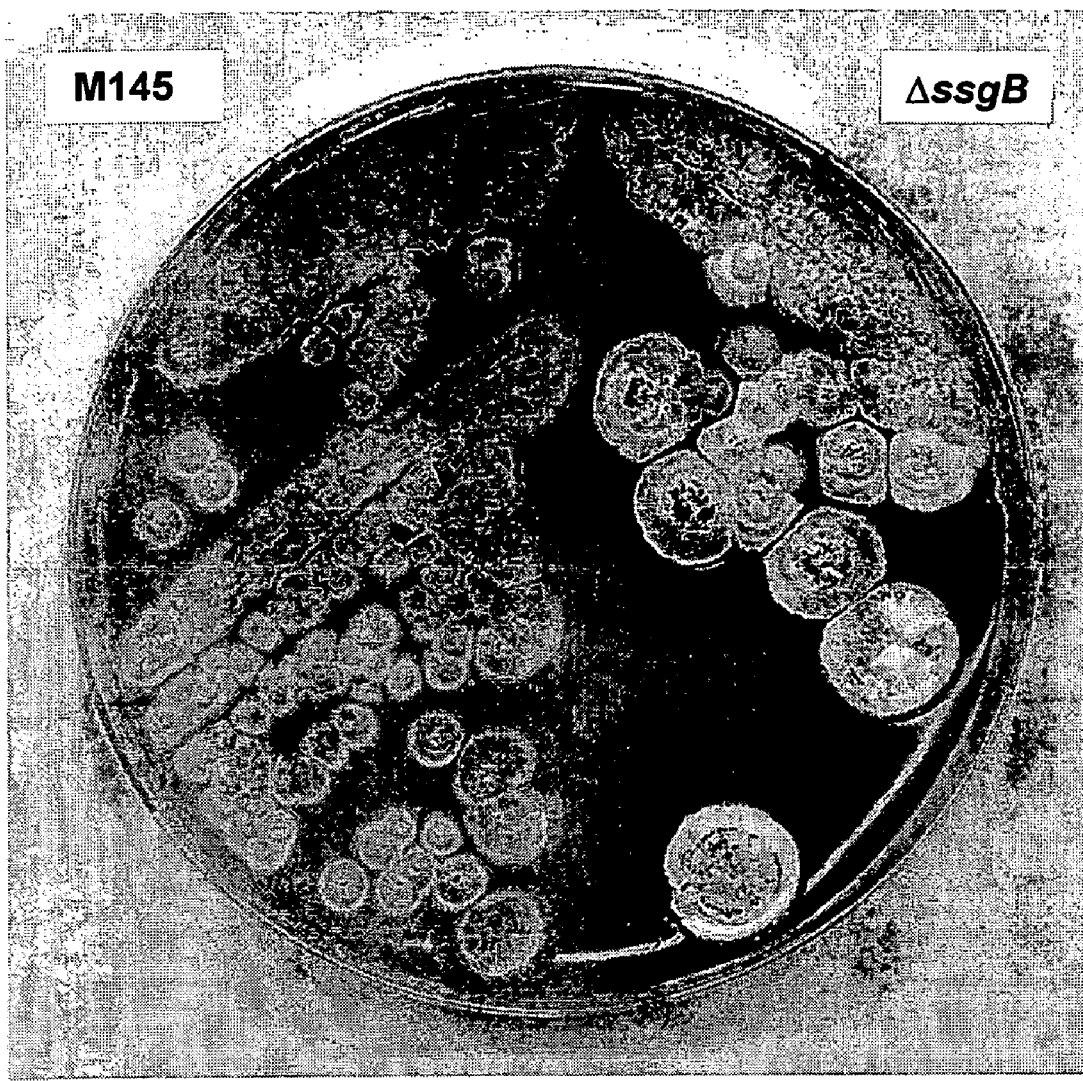

FIG. 11. Phenotype of the ssgB mutant of *S. coelicolor*. Left: *S. coelicolor* M145 (wild-type). Right: ssgB mutant. Strains were plated on SFM medium. The ssgB mutant fails to sporulate, even after prolonged incubation on SFM or MM. Note that the colonies of the ssgB mutant are unusually large, and overproduce actinorhodin.

Figure 12:
Figure 12:
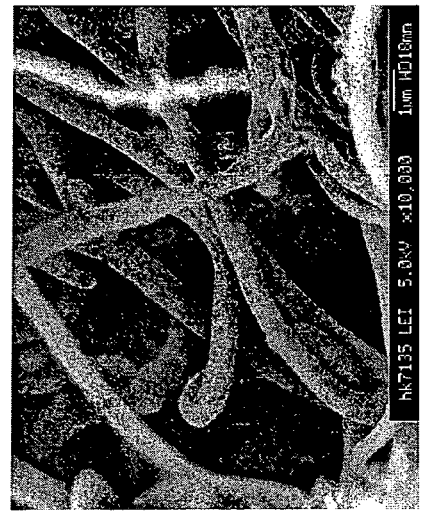
Figure 12:

FIG. 12. Characterization of the ssgB mutant by cryo scanning electron microscopy. Top: Sporulating aerial hyphae of *S. coelicolor* M145. Bottom: Smooth and non-sporulating aerial hyphae of the ssgB mutant. Left photograph shows rare and aberrant spore-like bodies, right photograph shows extremely smooth aerial hyphae, typical of the ssgB mutant.

Figure 13A:
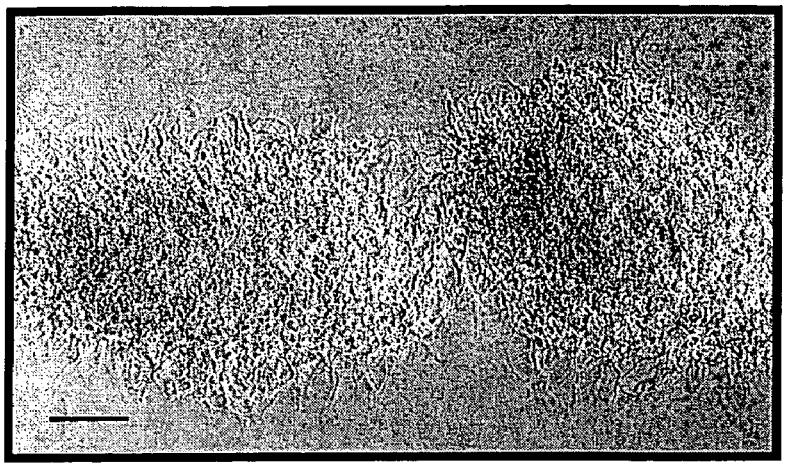
Figure 13B:
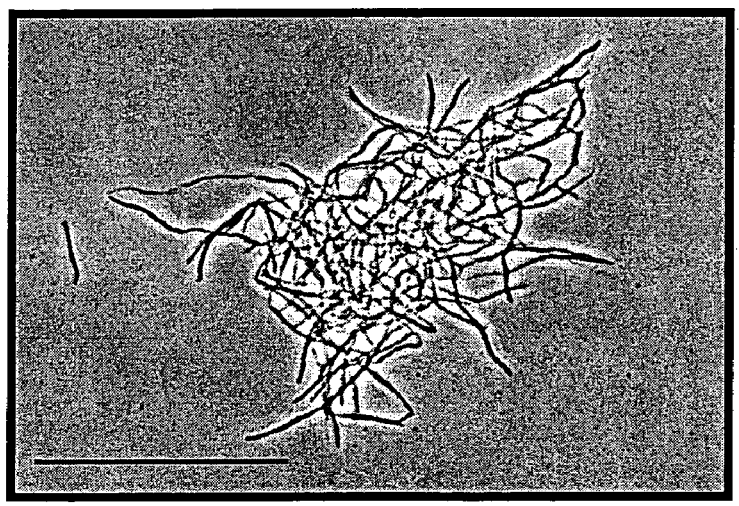

FIG. 13. Effect of multiple copies of ssgB on the morphology of *Streptomyces coelicolor*. Left: *S. coelicolor* M145 wild-type. Right: M145 harboring pWHM3/ssgB. Bar represents 10 µm. Introduction of additional copies of ssgB results in significantly smaller and more open pellets, with long non-branching hyphae protruding from the "clump."

Figure 14:
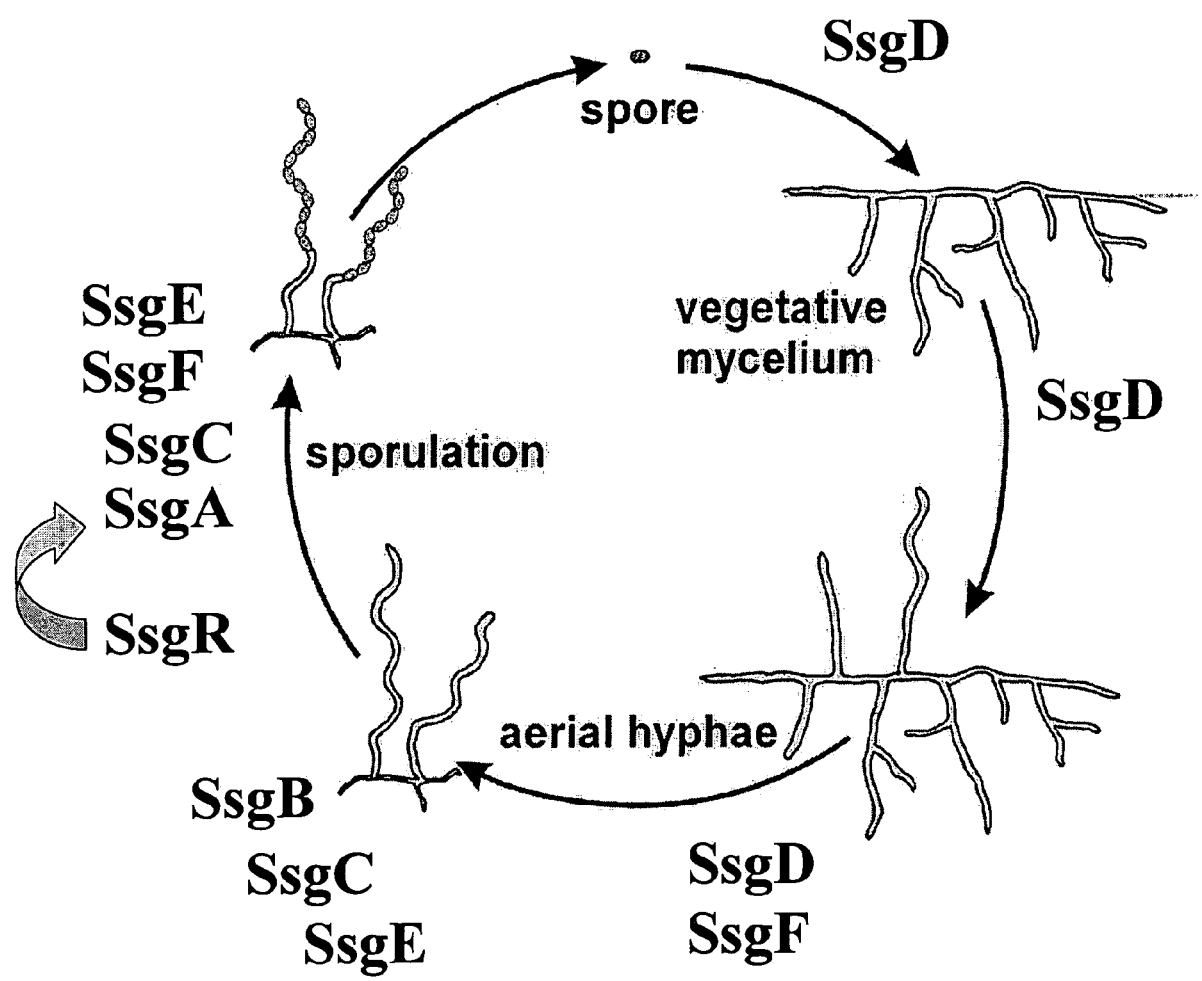

FIG. 14. Timing of expression of the ssgA-like genes, and of ssgR, in the *S. coelicolor* life cycle. A schematic representation of the *Streptomyces* life-cycle is shown, including the approximate time of expression of ssgA-like genes, and of ssgR, as determined by promoter probing and/or nuclease S1 mapping experiments. The arrow between SsgR and SsgA (SEQ ID NO:11) indicates activation of SsgA (SEQ ID NO:11) expression by SsgR.

Figure 15A:
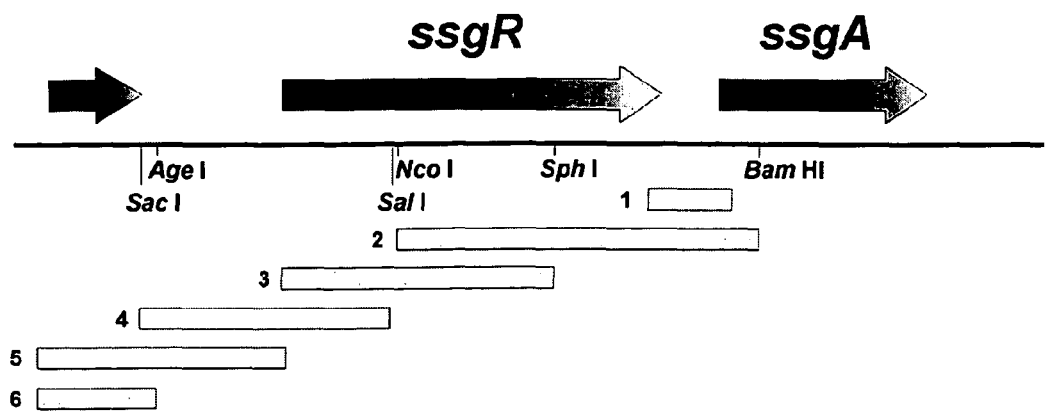
Figure 15B:
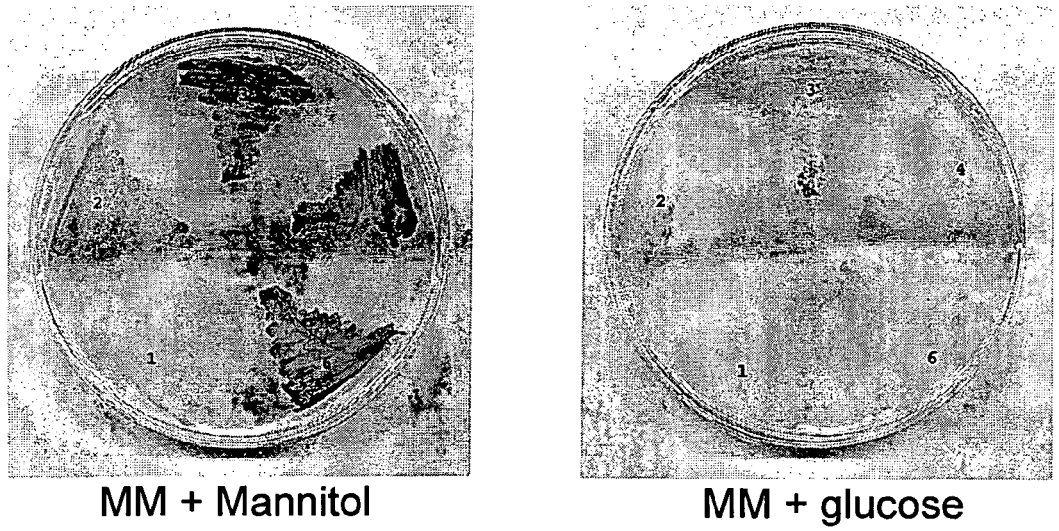

FIGS. 15A through 15B. Promoter probing analysis of the ssgRA operon.

FIG. 15A. Organization of the ssgRA operon and DNA fragments used for promoter probe analysis. EcoRI/BamHI-digested DNA fragments were placed in front of the promoterless redD gene in pIJ2587, with the ssgA-proximal part of the fragments positioned closest to redD, thereby providing the correct transcriptional directionality (see also the text and Table 2).

FIG. 15B. Glucose repression of the ssgRA operon. Transformants harboring pIJ2587 with inserts indicated under (A), were plated on minimal medium with either mannitol (left) or glucose (right) as the sole carbon source. Suppression of red pigment production indicates strong glucose repression of all ssgRA promoters.

Figure 16:
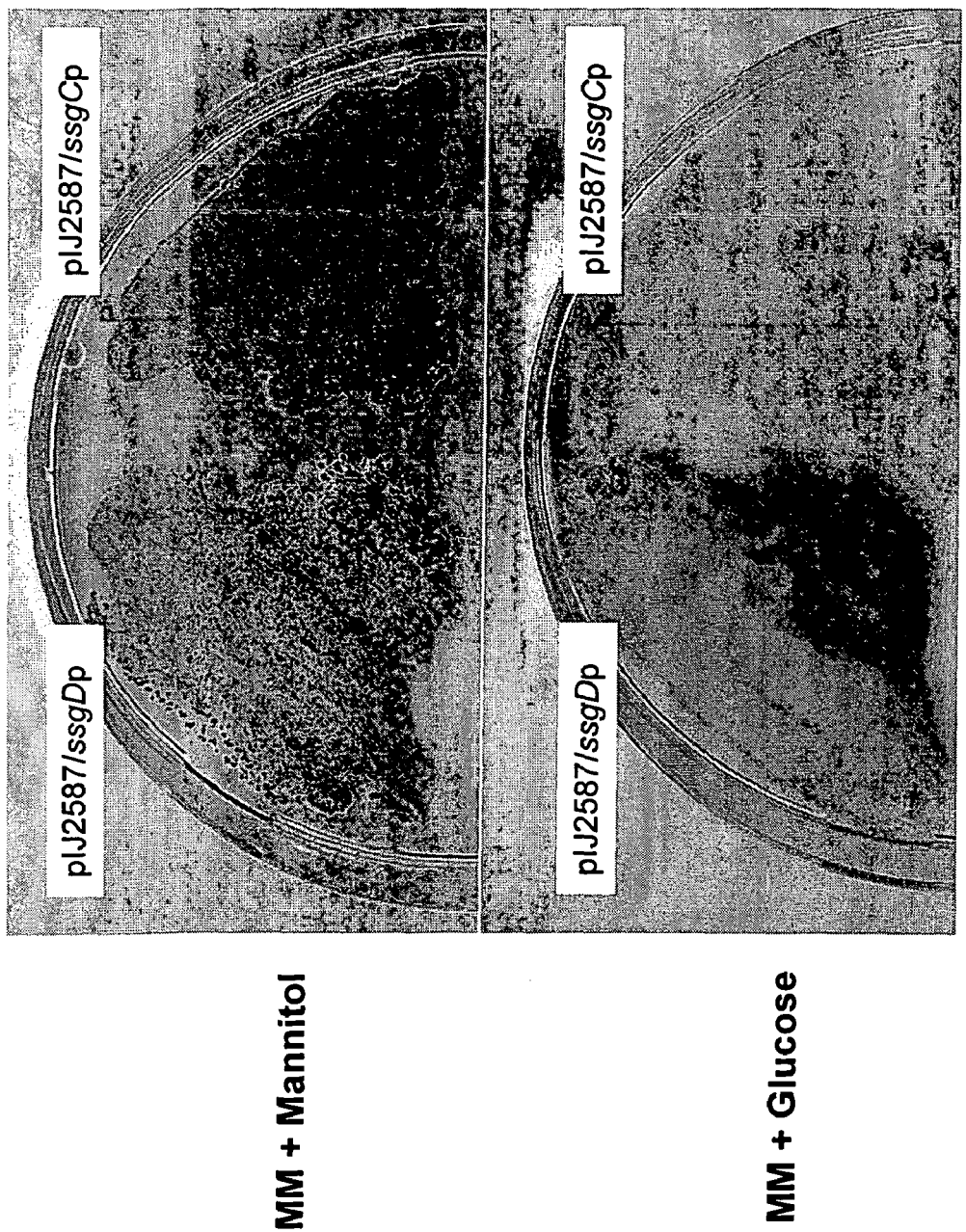

FIG. 16. Effect of glucose on ssgC promoter activity. M512 harboring pIJ2587/ssgCp or 2587/ssgDp was grown on MM with mannitol as the sole carbon source (Top), or with glucose (Bottom). M512 is a mutant of M145 which lacks the activator genes redD and actII-ORF4 for the biosynthesis of the antibiotics RED and ACT, respectively. pIJ2587 is a low-copy number vector that contains the promoterless redD gene. Promoter activity of a DNA fragment placed in front of redD is shown by the appearance of the red-pigmented undecylprodigiosin (RED).

Failure of ssgCp to activate red pigment production in the presence of glucose, indicates effective glucose repression of this promoter. Glucose had no apparent effect on the activity of the ssgD promoter.

Figure 17:
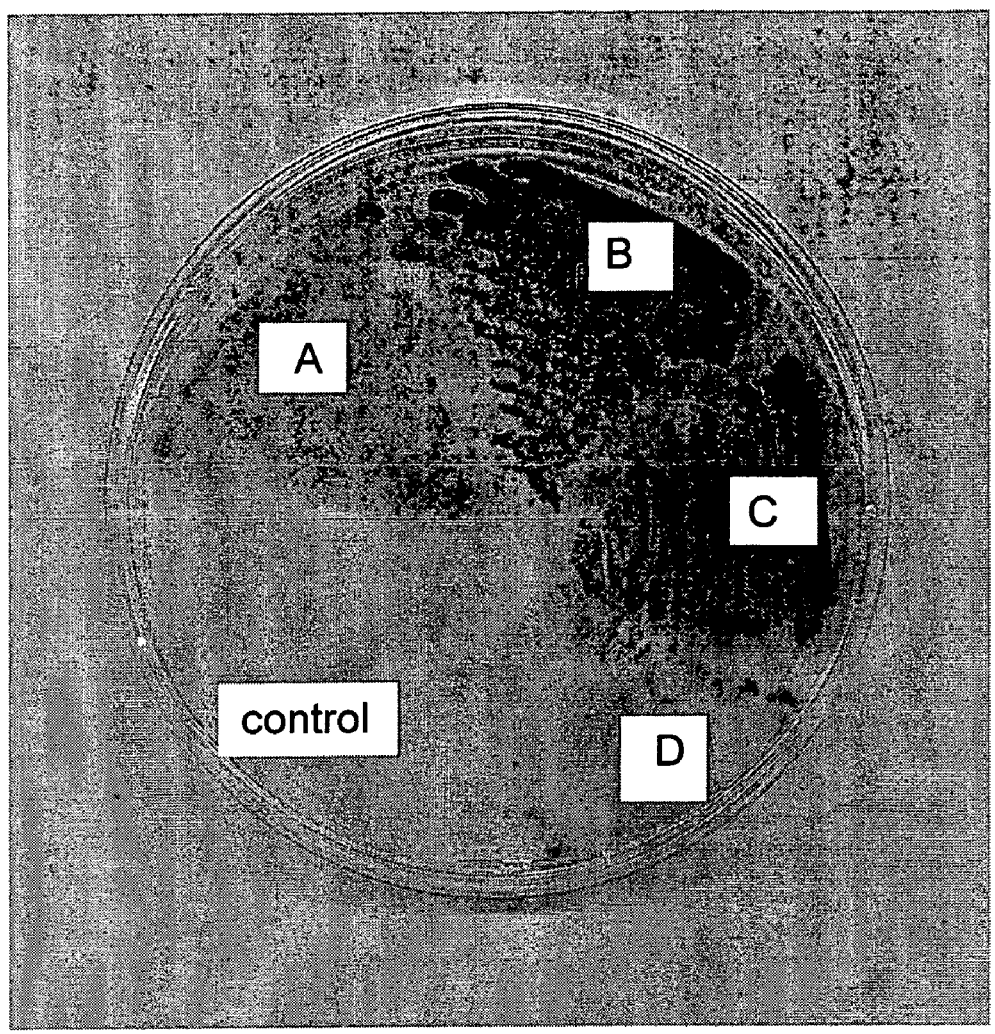

FIG. 17. Promoter probing of ssgABCE promoters in a glucose kinase mutant of M512. Glucose repression of the ssgRA and ssgC promoters are relieved in a glucose kinase mutant. This confirms that these promoters are indeed subjected to glkA-dependent catabolite control. Inserts were putative promoter sequences of A, ssgR (ssgRA operon promoter); B, ssgB; C, ssgC; D, ssgG upstream region. Control, M512 harboring control pIJ2587 (without insert).

Figure 18:
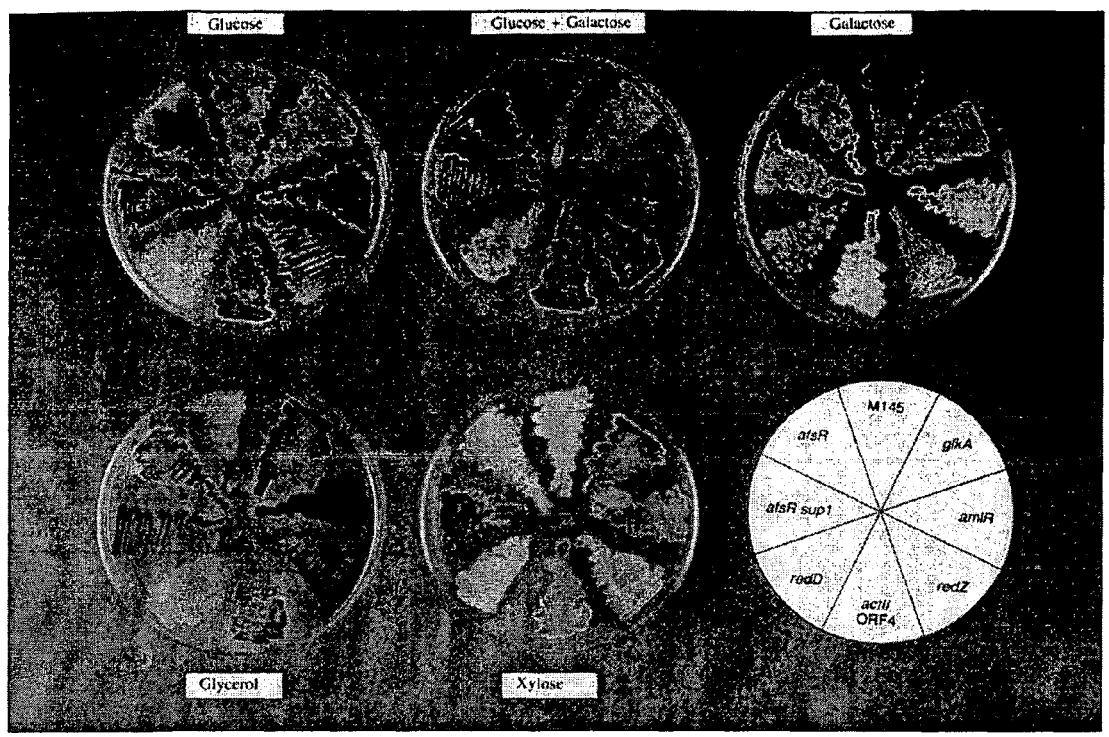
Figure 18:
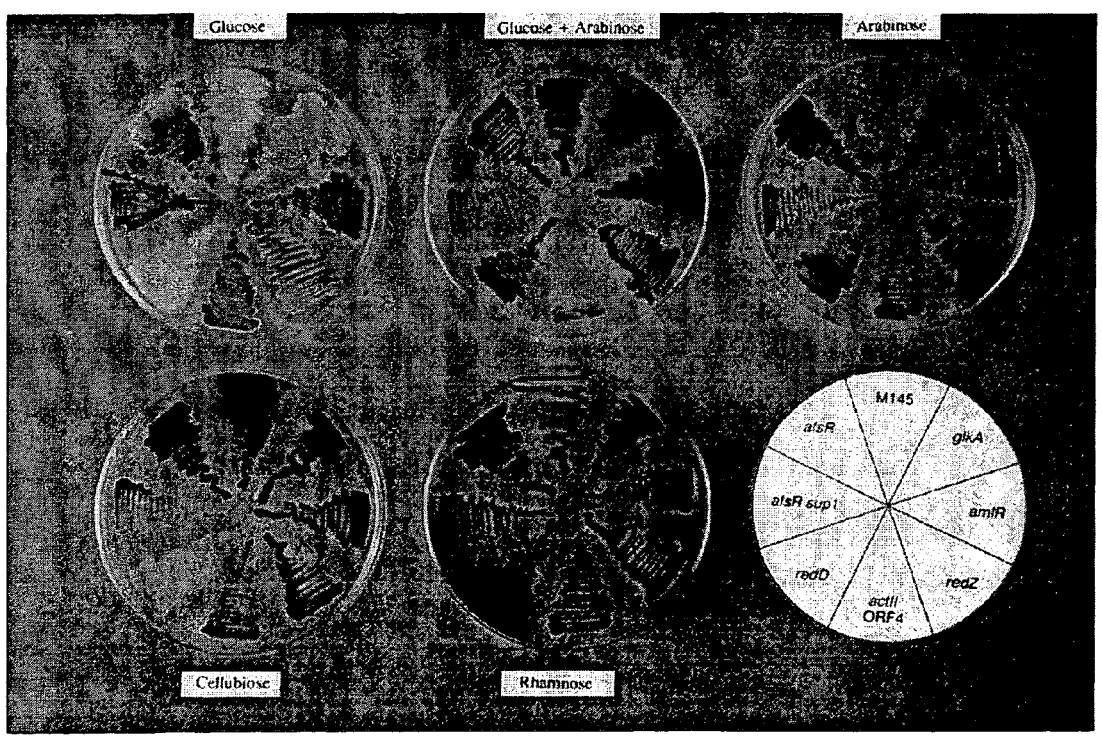
Figure 19:
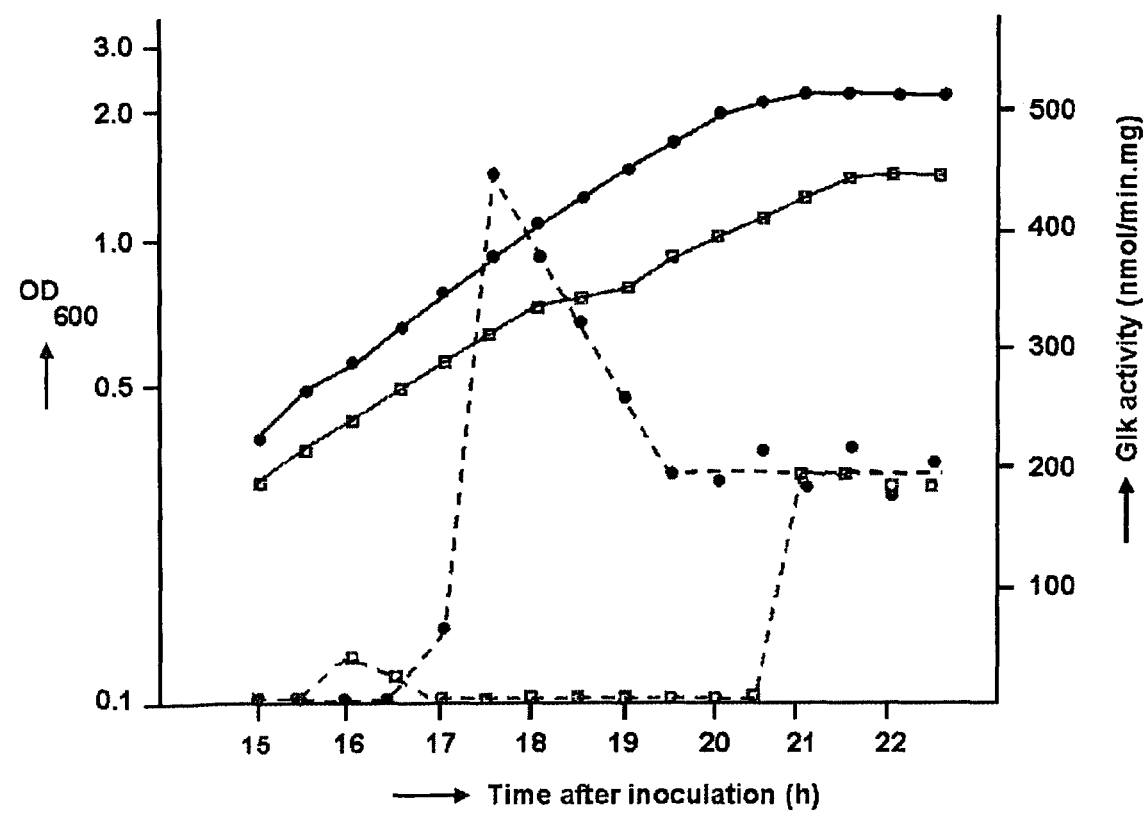

FIG. 18. Effect of carbon utilization on antibiotic production. For more information on particular mutants, and references, refer to Table 1.
1. M145, *S. coelicolor* M145 (parental strain).
2. glkA, glucose kinase mutant
3. amlR, MalR mutant M541 (overexpresses maltose utilization genes)
4. redD, mutant for the activator of the RED biosynthesis pathway
5. redZ, mutant for transcriptional activator of redD
6. actII-ORF4, mutant for the activator of the ACT biosynthesis pathway
7. afsR, mutant for a pleiotropic regulator of antibiotic biosynthesi
8. afsR sup, suppressor of afsR mutant that overproduces antibiotic FIG. 19. Activation of glucose kinase enzymatic activities by glucose. Growth curves are indicated by solid lines, glucose kinase activities by dashed lines. *Streptomyces coelicolor* was grown in NMMP supplemented with glucose (filled dots), or mannitol (open squares) as the carbon source.

Clearly visible is the induction of glucose kinase activity during exponential growth in glucose-, but not in mannitol-grown cultures. Glucose kinase activities were standardized against total protein content, and corrected for glucose kinase concentrations (see next figure).

Figure 20:
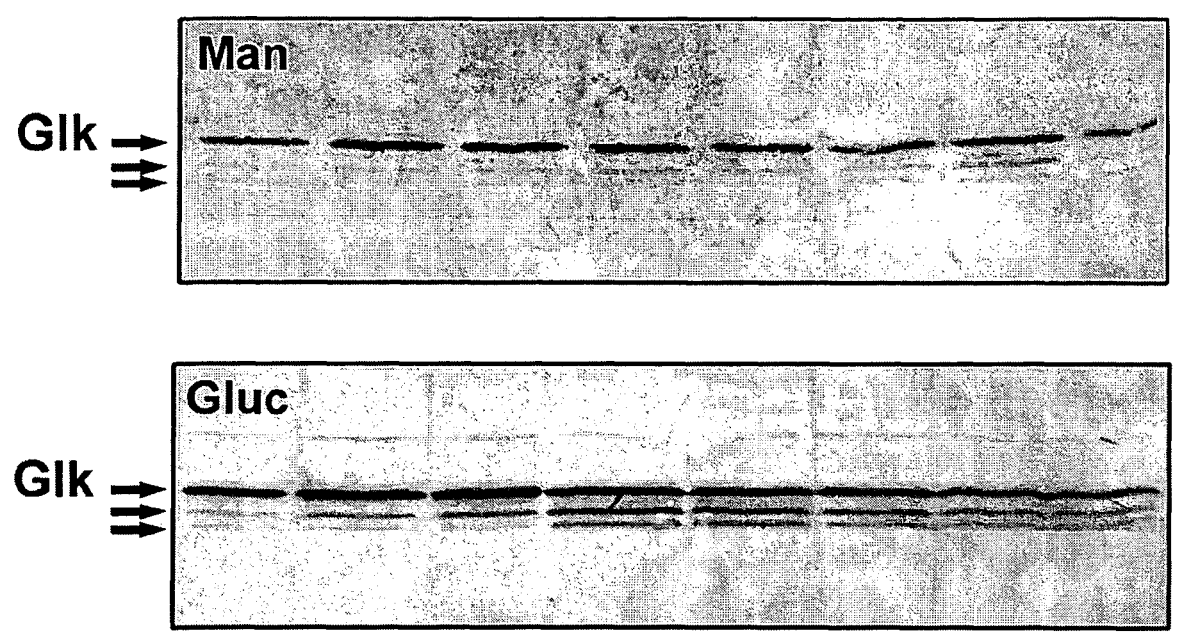

FIG. 20. Western analysis of *S. coelicolor* extracts from submerged cultures. *S. coelicolor* M145 was grown in NMMP supplemented with glucose or mannitol, respectively. The growth curves and glucose kinase activities are shown in the previous figure. All protein extracts were standardized against total protein content.

Clearly visible are two additional bands with a migration rate faster than the major Glk protein band. It is anticipated that Glk is activated in the presence of glucose by post-translational modification.

Figure 21:
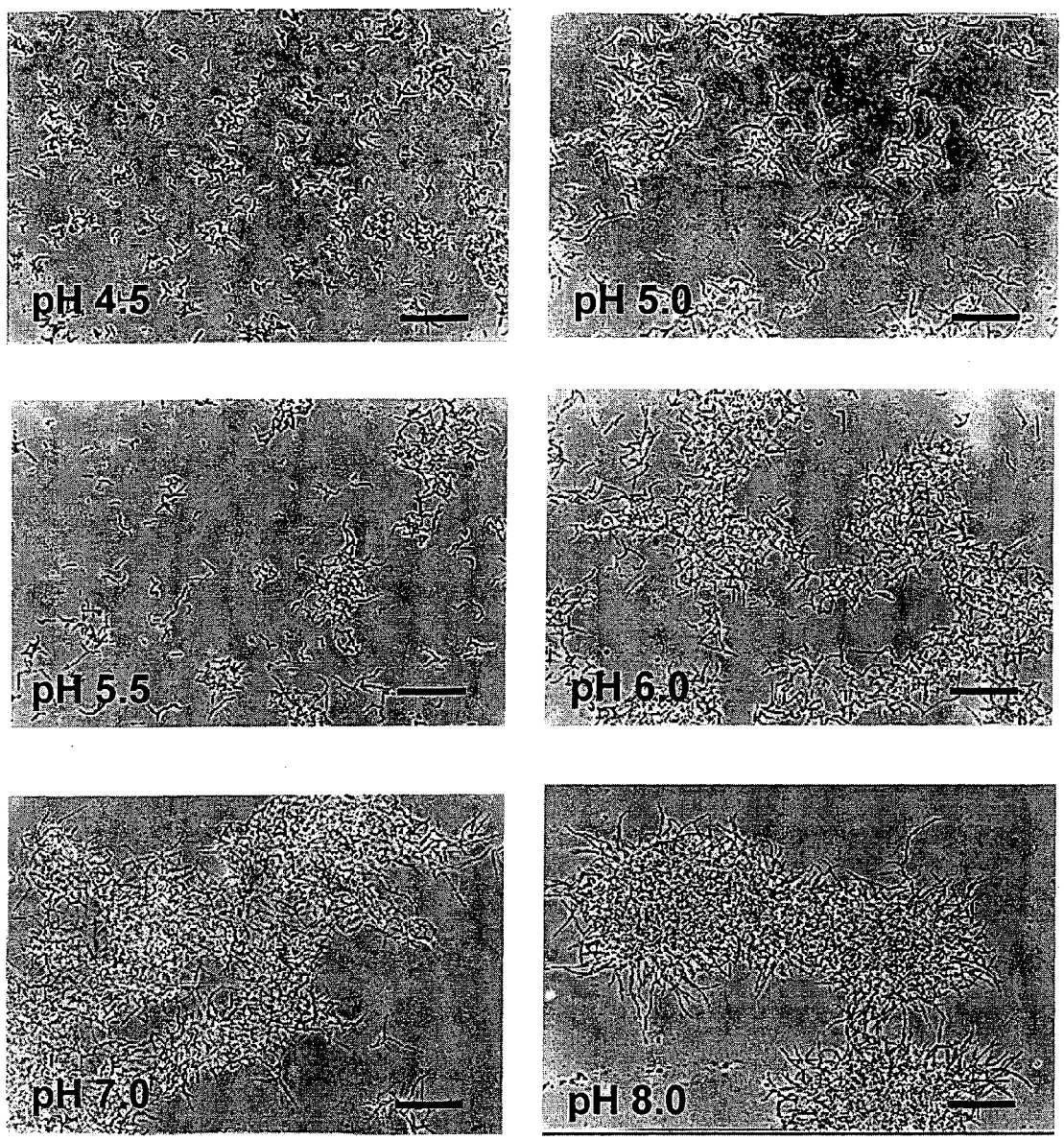

FIG. 21. Effects of pH on morphology of *S. coelicolor*. *S. coelicolor* M145 containing pGWS4-SD (overexpressing ssgA) was grown for 40 hours in TS medium, buffered at pH 4.5, 5.0, 5.5, 6.0, 7.0 or 8.0 with MOPS buffer. Typical examples of phase contrast micrographs from these cultures are shown. All samples shown at the same magnification. Bar=20 µm.

DETAILED DESCRIPTION OF THE INVENTION

Experimental Part

Materials and Methods
Bacterial Strains and Culturing Conditions
The bacterial strains used in this application are listed in Table 1.

TABLE 1

Bacterial strains described in this patent application.

| Bacterial strain | Genotype | Reference |
| --- | --- | --- |
| *S. coelicolor* M145 | wild-type, SCP1⁻, SCP2⁻ | Kieser et al., 2000 |
| *S. lividans* 1326 | Wild-type | Kieser et al., 2000 |
| *S. avermitilis* | wild-type | ATCC 31267 |
| *S. roseosporus* | wild-type | ATCC 31568 |
| *Sacch. erythraea* | wild-type | ATCC 11635 |
| GSA3 | M145 ΔssgA | Van Wezel et al., 2000c |
| GSB1 | M145 ΔssgB | This patent application |
| GSR1 | M145 ΔssgR | This patent application |
| J1915 | M145 ΔglkA | Kelemen et al., 1995 |

TABLE 1-continued

Bacterial strains described in this patent application.

| Bacterial strain | Genotype | Reference |
| --- | --- | --- |
| M510 | Ml45 ΔredD | Floriano and Bibb, 1996 |
| M511 | M145 ΔactII-ORF4 | Floriano and Bibb, 1996 |
| M512 | M145 ΔactII-ORF4 ΔredD | Floriano and Bibb, 1996 |
| M512 Dog[R] | M512 ΔglkA | This patent application |
| M550 | Ml45 ΔredZ | White and Bibb, 1997. |
| M513 | M145 ΔafsR | Floriano and Bibb, 1996 |
| M513sup | M513 over-producing antibiotics | This patent application |
| M541 | M145 ΔmalR | van Wezel et al., 1997 |
| E. coli JM109 | See reference | Messing et al., 1981 |

E. coli K-12 strains JM109 was used for propagating plasmids, and was grown and transformed by standard procedures (Sambrook et al., 1989); transformants were selected in L broth containing 1% (w/v) glucose, and ampicillin at a final concentration of 200 μg ml$^{-1}$. L broth with 1% glucose and 30 μg ml$^{-1}$ chloramphenicol was used to grow ET12567.

Streptomyces coelicolor A3(2) M145 and Streptomyces lividans 1326 were obtained from the John Innes Centre strain collection, and were used for transformation and propagation of Streptomyces plasmids. Protoplast preparation and transformation were performed as described by Kieser et al. (2000). SFM medium (mannitol, 20 gl$^{-1}$; soya flour, 20 gl$^{-1}$; agar, 20 gl$^{-1}$, dissolved in tap water) was used to make spore suspensions. Minimal Medium (MM) and R2YE agar plates (Kieser et al., 2000) were used for promoter-probing experiments; R2YE was also used for regenerating protoplasts and, after addition of the appropriate antibiotic, for selecting recombinants. For standard cultivation of Streptomyces, and for plasmid isolation, YEME (Kieser et al., 2000) or tryptone soy broth (Difco) containing 10% (w/v) sucrose (designated TSBS), were used. Growth curves were performed in NMMP (liquid minimal medium), with 1% mannitol as the carbon source.

Creating 2-deoxyglucose-Resistant Strains

For this purpose, strains were grown on MMD medium, a solid minimal medium with mannitol (1% w/v) and 100 mM 2-deoxyglucose, which is lethal for Glk$^{-+}$ strains. Therefore colonies that develop on this medium have to be Glk$^-$. For each mutant, three independent colonies that were able to grow on MMD were selected, and tested for glucose kinase activity. Strains that lack glucose kinase activity are glucose kinase deficient (ΔglkA). Strains were checked by PCR, which showed that the nature of the mutations varied from large deletions to point mutations. Those harboring very large deletions (beyond the glkA gene) were discarded.

Plasmids and Constructs

1. General Cloning Vectors pIJ2925 (Janssen and Bibb, 1993) is a pUC-derived plasmid used for routine subdloning. For cloning in Streptomyces we used pHJL401 (Larson and Herschberger, 1986), and pWHM3 (Vara et al.). pHJL401 is a shuttle vector containing the E. coli pUC19 and Streptomyces SCP2* (Lydiate et al., 1985) origins of replication, giving approximately 10 copies per chromosome in Streptomyces; pWHM3 is a shuttle vector containing the E. coli pUC19 and Streptomyces pIJ101 origins of replication (approximately 50 copies per chromosome). E. coli plasmid DNA was isolated from S. lividans prior to transformation to S. coelicolor.

2. Constructs for Promoter Probing pIJ2587 (van Wezel et al., 2000a) was used for promoter probing experiments. It is an E. coli-Streptomyces shuttle vector derived from pHJL401 with pUC19 and SCP2* origins of replication; it possesses a copy number of approximately 10 per chromosome in streptomycetes. Fragments harboring upstream sections of the respective ssgA-like genes, as well as of ssgR, were amplified by PCR, using 30-mer oligonucleotides. The oligonucleotides were designed such, that restriction sites were added so as to clone the upstream sequences as EcoRI-BamHI fragments, with the BamHI site proximal to the start of the genes. In this way, possible promoter sequences were positioned in the desired orientation and immediately upstream of the promoterless redD gene in pIJ2587. Red production by the transformants on R2YE plates was assessed visually. The exact inserts of the constructs are shown in Table 2.

TABLE 2

Inserts of promoter-probe constructs.

| Construct | Gene(s) transcribed | Cosmid | Genbank Accession (protein) | Insert (relative to translational start site of the given gene) |
| --- | --- | --- | --- | --- |
| pIJ2587-ssgA$_S$ | No activity | Q11 | CAB46964 | −197/+71 |
| pIJ2587-ssgA$_L$ | ssgA | Q11 | CAB46964 | −500/+71 |
| pIJ2587-ssgBp | ssgB | L2 | CAB70943 | −590/+90 |
| pIJ2587-ssgCp | ssgC | 5H1 | CAB42928 | −1050/−5 |
| pIJ2587-ssgDp | ssgD | 5F2A | CAB40672 | −290/+22 |
| pIJ2587-ssgEp | ssgE | E87 | CAB59654 | −225/+40 |
| pIJ2587-ssgFp | ssgF | 8A11 | CAC01575 | |
| pIJ2587-ssgGp | ssgG | E19A | CAB51005 | −470/+64 |
| Several constructs | ssgR + ssgA | Q11 | CAB46963 (SsgR) CAB46964 (SsgA) (SEQ ID NO: 11) | Several inserts |

Exact location of the DNA fragments harboring upstream sequences of the various ssgA-like genes, as well as ssgR, are shown. The inserts were cloned as EcoRI-BamHI fragments into pIJ2587, to allow transcription of the promoterless redD gene. Fragments were amplified by PCR, using the relevant oligonucleotides.

3. Constructs for the Expression of ssgA and ssgA-like Genes in Streptomyces

For the overexpression of ssgA in actinomycetes, pGWS4-SD was used, an integrative expression construct based on pSET152 (Bierman et al., 1992), containing ssgA behind the strong and constitutive ermE promoter. Construction of this construct was described in European patent application 99929959.7 (publication number 1090121).

For complementation experiments, DNA fragments harboring ssgA-like genes and upstream sequences were inserted into pHJL401. These constructs for the expression of ssgB, ssgC, ssgD, ssgE, ssgF, and ssgG, were designated pGWB1, pGWC1, pGWD1, pGWE1, pGWF1, and pGWG1, respectively. Presence of active promoters was confirmed by promoter probing (see below). Restriction maps of ssgB-G and flanking regions, and exact inserts of the expression constructs are shown in FIGS. 8A-8F.

4. Constructs for the Expression of Hybrid ssgAX Genes

As an alternative to expression constructs harboring complete copies of any of the ssgA-like genes ssgB-G, hybrid constructs were produced containing the ssgRA operon with the part of ssgA following the BamHI site replaced by comparable parts of any of the ssgA-like genes. The architecture of these constructs is shown in FIG. 9A. In this way, timing of expression of the hybrid ssgAX genes is similar to that of ssgA. The pHJL401-based constructs contain the BglII- BamHI part of ssgRA operon (i.e., the −440/+1000 region relative to the ssgR translational start codon; cf FIG. 4A), fused to an approximately 600 bp PCR-generated BamHI-HindIII DNA fragment, with the BamHI site created at a position corresponding to the fully conserved proline residue (aa residue 24 in the SsgA (SEQ ID NO:11) sequence) shown in the alignment (FIG. 7).

5. Construction of pGWB2 for Gene Replacement of ssgB

Figure 8A:
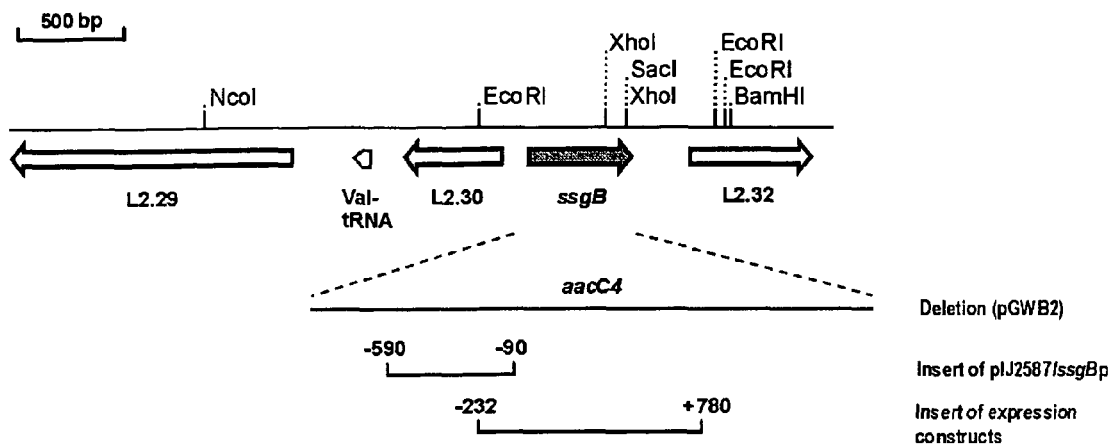
Figure 8B:
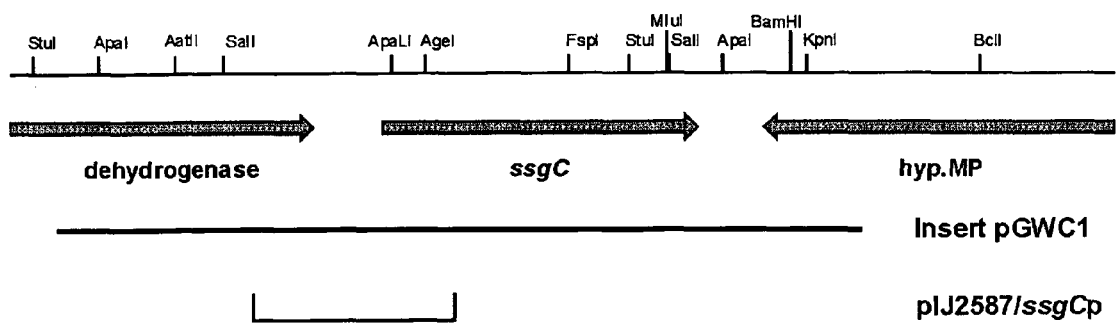
Figure 8C:
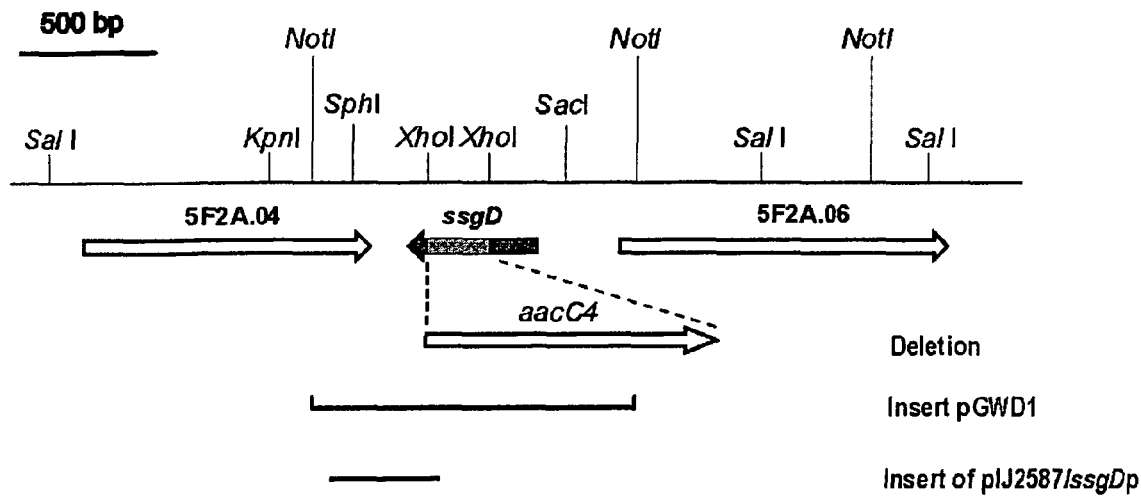
Figure 8D:
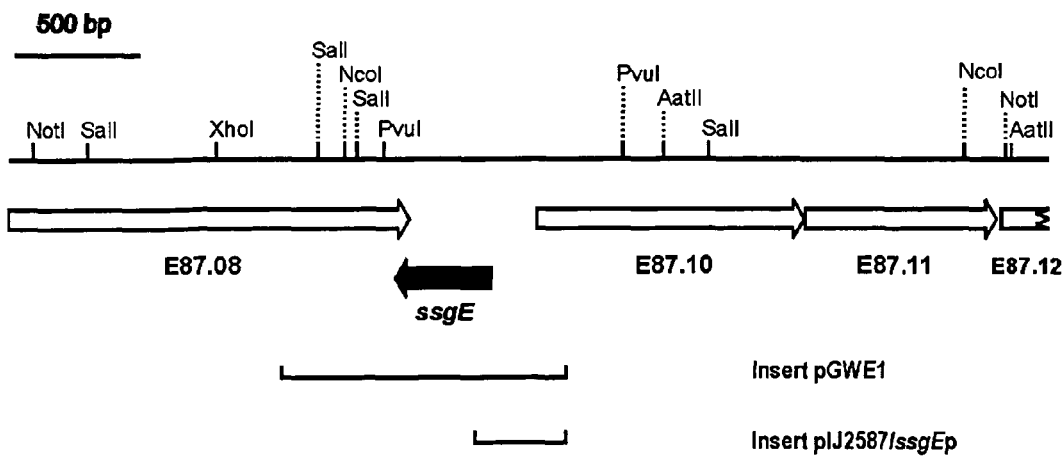
Figure 8E:
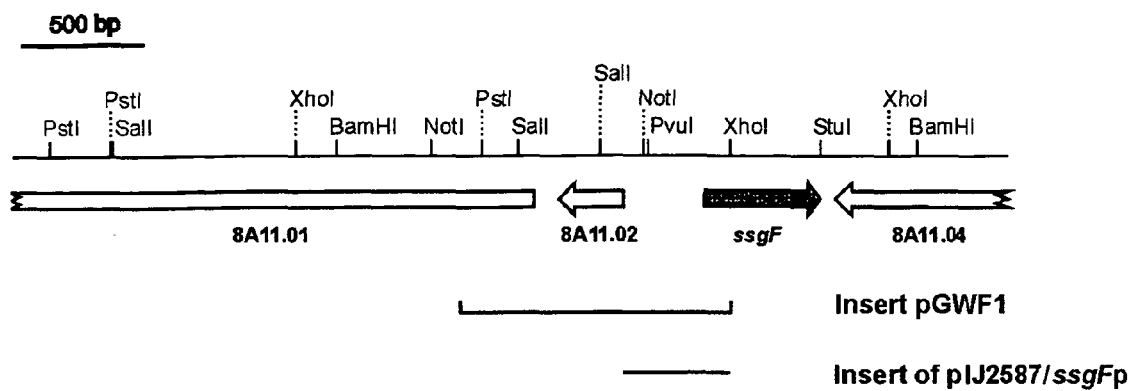
Figure 8F:
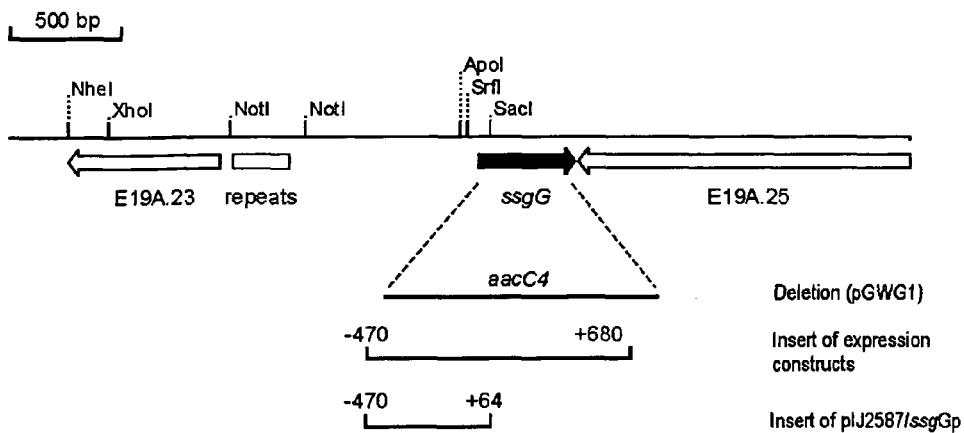

The regions −1000/+3 and +410/+1400 relative to the start of the ssgB gene were amplified by PCR, using 30-mer oligonucleotides. These were designed such as to introduce a BamHI site in the middle of the insert, allowing introduction of the apramycin resistance cassette. A thiostrepton resistance cassette on the vector part of pGWB2 allowed distinction between single and double recombination events. Transformants were selected for Apra$^R$ and subsequently screened for thiostrepton sensitivity, indicative of loss of the plasmid. The region deleted in the mutant and replaced by the apramycin resistance cassette is shown in FIG. 8A.

6. Construction of pGWR2 for In-Frame Deletion of ssgR

To create a construct for the deletion of ssgR, the 1400 bp BglII-BamHI fragment containing ssgR and part of ssgA (FIG. 4A) was inserted into BamHI-digested pIJ2925, and the NcoI-SphI segment of ssgR was removed, to create an in-frame deletion in the ssgR gene on the plasmid. Subsequently, the apramycin resistance cassette aacC(4) (Kieser et al., 2000) was inserted into the EcoRI site of the construct (outside the ssgRA insert), producing pGWR2. This construct allows production of an in-frame deletion mutant of ssgR. After transformation of the non-replicating construct to *S. coelicolor* M145, initial integrants (apramycin resistant) were selected, allowed to sporulate on SFM plates without antibiotics, and replicated non-selectively to allow a second recombination event to take place, and plated for single colonies. The latter were replicated to SFM containing apramycin, to screen for double recombinants, which should have lost the plasmid and hence have become sensitive to apramycin. About 30% of all apramycin sensitive colonies were sporulation mutants. Testing of four sporulating and four non-sporulating double recombinants by PCR revealed that all sporulation mutants carried the expected 300 bp in-frame deletion, while sporulating colonies had a wild-type ssgR gene. One of the mutant colonies was selected, and designated GSR1. Location of the deletion is shown in FIG. 4A.

For complementation experiments plasmid pGWR1 was designated. This is a low-copy number pHJL401-based vector that harbors a 1.3 kb PCR-generated insert including the entire ssgR gene, and approximately 300 bp of upstream sequences, including the ssgR promoter region.

Small Scale Fermentations

For analysis of the effect of enhanced expression of ssgA on the growth rate and on productivity of actinomycetes, growth curves were performed in small scale fermentations using a BioFlo 3000 5L bench top fermenter (New Brunswick Biosciences). 4.5 liters of Tryptone soy broth with 10% sucrose (TS medium) containing 50 mM CuCl$_2$ and the relevant antibiotics, were inoculated with a 100 ml preculture, grown for 30 hours at 30° C. in a spring-coiled flask. The fermentation inoculum was 0.2 g/l. Fermentations were performed at 30° C., and the pH was fixed at 6.5, by the addition of 2N phosphoric acid or 2N NaOH. Dissolved oxygen tension was set at 80% and maintained by changing the stirrer speed.

Tyrosinase Activity Assays

The specific enzymatic activity of tyrosinase secreted by transformants of *S. lividans* 1326 harboring pIJ703 (Katz et al., 1983) was determined as described previously, following the conversion of 1 mM DOPA spectrophotometrically at 475 nm (Lerch and Ettinger, 1972). Activity (expressed as $\Delta A_{475}$/sec.ml) was corrected for biomass content of the samples.

Antibiotic Activity Assays

To assess the total antimicrobial activity present in the culture fluid of *S. roseosporus* fermentations, 40 ml samples were taken at regular intervals, biomass was harvested by centrifugation (20 minutes at 10,000 rpm), and residual debris removed by filtration using a 0.22 μm bacterial filter (millipore). A lawn of *Streptomyces avermitilis* ATCC31267 was streaked on minimal medium agar plates containing 0.5 M CaCl$_2$, with mannitol as the sole carbon source (1% w/v). Sterile 0.6 cm antibiotic assay filter paper discs (Whatman grade AA) were placed onto the plates and 10 μl of filtered supernatant was spotted on these filters. Plates were allowed to grow for four days and photographed. Zones of clearing (dark halos) represent growth inhibition due to antibiotics present in the culture fluid of the *S. roseosporus* fermentations.

PCR Conditions

Polymerase chain reactions (PCRs) were performed in a minicycler (MJ Research, Watertown, Mass.), using Pfu polymerase (Stratagene, La Jolla, Calif.), and the buffer provided by the supplier, in the presence of 5% (v/v) DMSO and 200 μM dNTP. No additional Mg$^{++}$ was added to the reaction mixture. The following PCR program was used for 30 cycles: 45 seconds melting at 94° C., 1 minute annealing at 54° C., and 90 seconds extension at 72° C. The reaction was completed by an additional ten minutes incubation at 72° C.

Nuclease S1 Protection Assays

RNA was purified from MM agar plates with mannitol as the carbon source, as described by Kieser et al. (2000), except that DNase I treatment was used in addition to salt precipitation to eliminate DNA from the nucleic acid preparations. For each nuclease S1 protection assay, about 0.02 pmol (about 10$^4$ Cerenkov counts minute$^{-1}$) of labeled probe was hybridized to 30 μg of RNA in NaTCA buffer at 45° C. overnight after denaturation at 70° C. for 15 minutes. All subsequent steps were carried out as described previously (Kieser et al., 2000), using an excess of probe.

The probes used for mapping ssgR and ssgA transcripts were amplified from DNA of *S. coelicolor* cosmid Q11. The following probes were amplified; for mapping ssgR transcripts, a 393 nt probe covering the −320/+72 region relative to the ssgR translational start codon, and for ssgA a 233 nt probe covering the −192/+41 region relative to the translational start codon of ssgA.

Glucose Kinase Activity Assays

*S. coelicolor* strains were grown in 500 ml minimal medium (SMM) supplemented with 1% (w/v) glucose or mannitol, under vigorous shaking at 28° C. Cells were harvested at 30 minute intervals, washed twice and then resuspended in cold standard buffer (50 mM Tris pH 7.4; 5 mM MgCl$_2$, 40 mM NH$_4$Ac, 50 mM NaCl, 1 mM DTT). Crude extracts were prepared by sonication at 50 W (Labsonic U (Braun); five times for 30 seconds each time) and subsequent removal of cell debris by centrifugation. Glucose kinase activity in cell extracts was assayed using 50 μg of total protein, in a reaction mixture containing 50 mM Tris-Cl (pH 7.0), 20 mM glucose, 25 mM MgCl$_2$, 0.5 mM NADP, 1 mM ATP, and 0.7 U Glucose-6-P dehydrogenase (Skarlatos and Dahl, 1998).

Western Blot Analysis

*S. coelicolor* strains were grown as described for the glucose kinase activity assay. Proteins of cell extracts were separated by SDS-polyacrylamide gel electrophoresis on a 7.5% polyacrylamide gel and transferred to a Hybond-C super (Amersham) by electroblotting. Glk was detected with a rabbit polyclonal antiserum raised against Glk(His$_6$) of *S. coelicolor*. Glk antibodies (Mahr et al., 2000) were visualized using the ECL Western blot analysis system (Amersham).

Results

Improvement of Growth Rate and Enzyme Production of *Streptomyces lividans*

To analyze what the effect is of enhanced expression of SsgA (SEQ ID NO:11) on growth rate and on product formation by actinomycetes, we used *Streptomyces coelicolor* M145, genetically the most well-characterized actinomycete, whose genome sequence was published recently (Bentley et al., Nature 417: 141 (2002)), and the related but industrially more relevant strain *Streptomyces lividans* 1326 as initial test systems. *S. coelicolor* forms large clumps during fermentation, and grow slowly (doubling time approximately three hours in defined media). Mainly due to these growth problems, *S. coelicolor* has never been used in industrial fermentations. The ssgA gene was introduced in the wild-type strain M145, which dramatically altered its morphology (van Wezel et al., 2000c). Recent tests in 5L fermentations showed strong reduction of the adaptation (lag) phase, and doubling of specific growth rate on introduction of M145+ssgA. Such an improvement of growth rate strongly reduces fermentation time, making the production process much more cost effective, as more fermentations can be run in the same time span.

Figure 1:
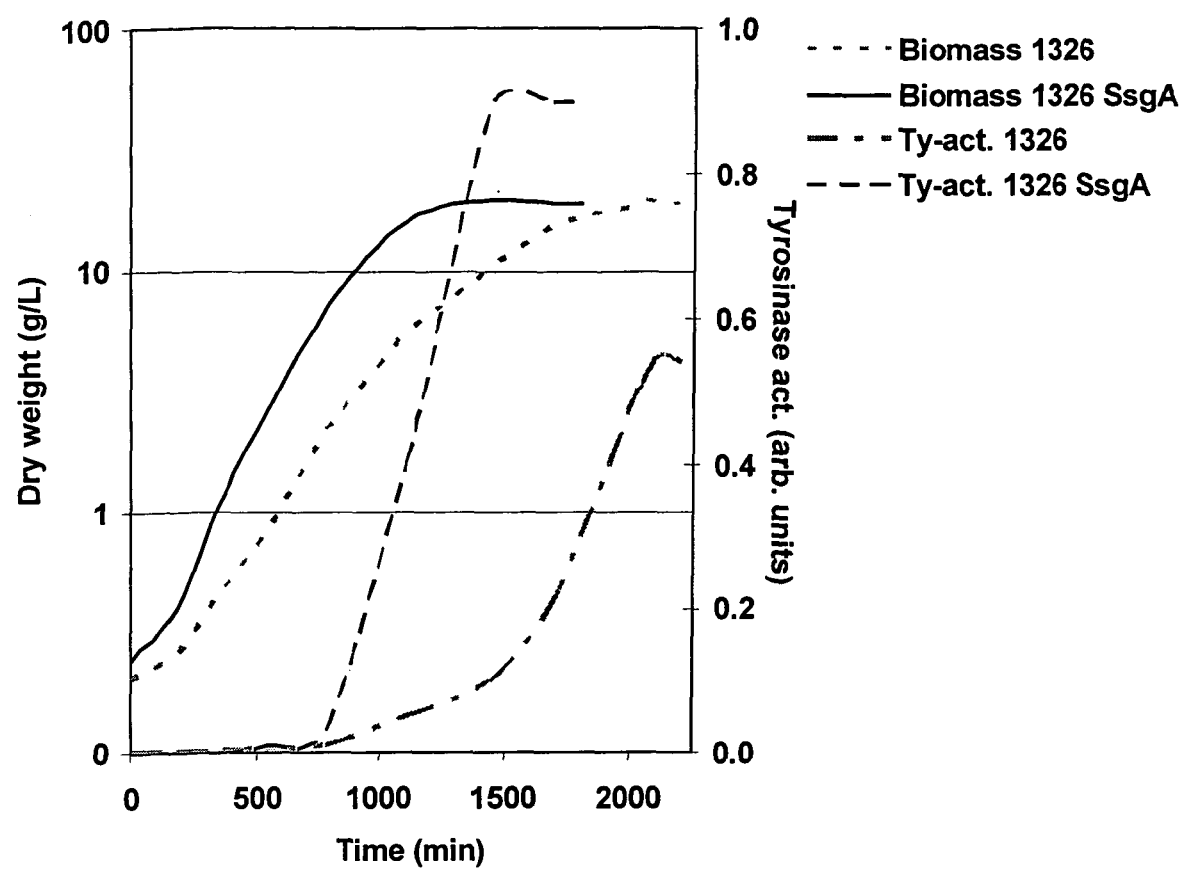
FIG. 1. Effect of ssgA expression on tyrosinase secretion by *S. lividans* 1326. Wild-type *S. lividans* 1326 harboring control plasmid (1326); *S. lividans* expressing SsgA (SEQ ID NO:11) (1326 SsgA, (SEQ ID NO:11)); Tyrosinase activity (Ty-act).

While the growth effects were very promising, we tested what effect this seemingly improved morphology had on the yield of secreted enzymes in small-scale fermentations. For this purpose, pIJ703, a plasmid expressing the tyrosinase gene (melC) (Katz et al., 1983) was introduced into *S. lividans* 1326, a strain often used for the commercial production of enzymes that require *Streptomyces* as the production host. Excitingly, expression of ssgA had a very positive effect on both growth rate and enzyme production (FIG. 1). Specific growth rate of the enzyme-producing *S. lividans* during fermentation had approximately doubled. Another important observation is the reduced so-called lag phase, or the time the culture requires entering exponential growth. Precultures of *S. lividans* harboring pGWS4-SD entered exponential growth significantly earlier than the control strain.

Clearly, the smaller mycelial clumps of the ssgA transformant were much better suited for the production of the secreted enzyme tyrosinase, as shown by the spectacular increase in tyrosinase activity of the ssgA transformant ("1326 ssgA" in FIG. 1). This strain reached a peak of 0.94 (arbitrary units) around 20 hours after start of the fermentation, while the control strain harboring the control plasmid pSET152 produced 0.55 arbitrary units after almost 35 hours.

Effects of Enhanced Expression of ssgA on Antibiotic Production

Figure 2A:
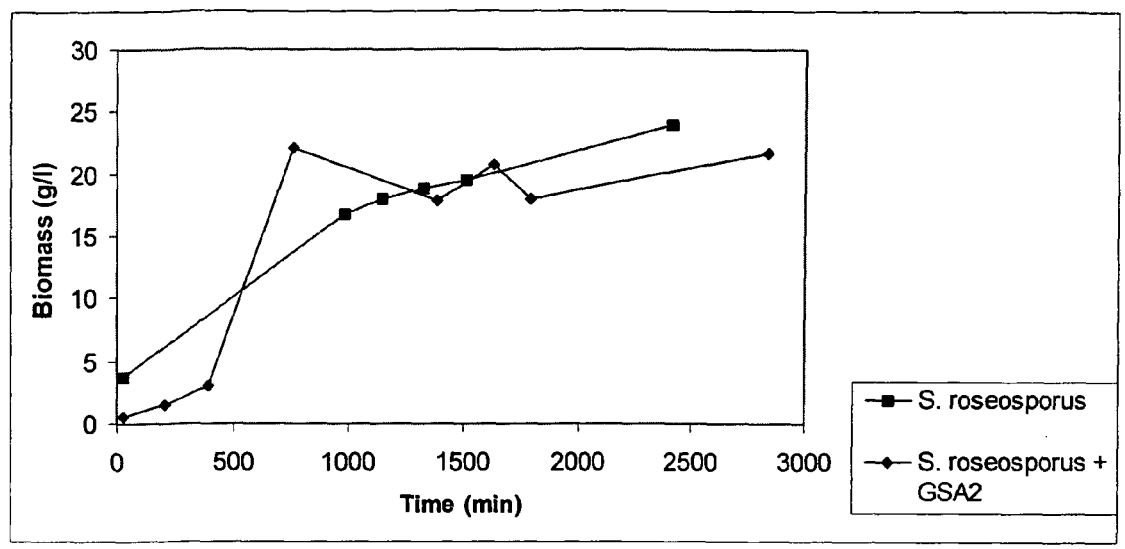
FIGS. 2A through 2C. Effect of ssgA overexpression on antibiotic production by *Streptomyces roseosporus* ATCC31568.

For the analysis of the effect of growth improvement on antibiotic production, we introduced pGWS4-SD into *Streptomyces roseosporus*, producer of the glycopeptide antibiotic daptomycin. Control transformants harbored pSET152. Similarly to the experiments described above for *S. coelicolor* and *S. lividans*, growth behavior was altered, with enhanced fragmentation and therefore reduced pellet formation. An example of growth curves is shown in FIG. 2A. 40 ml samples were taken at regular intervals from both fermentations, and analyzed for antimicrobial activity using a standard antibiotic assay (see Materials and Methods section). As indicator strain we used *Streptomyces avermitilis*. The size of the zone of clearing around the filter disc is a measure for the antibiotic concentration in the samples.

Figure 2B:
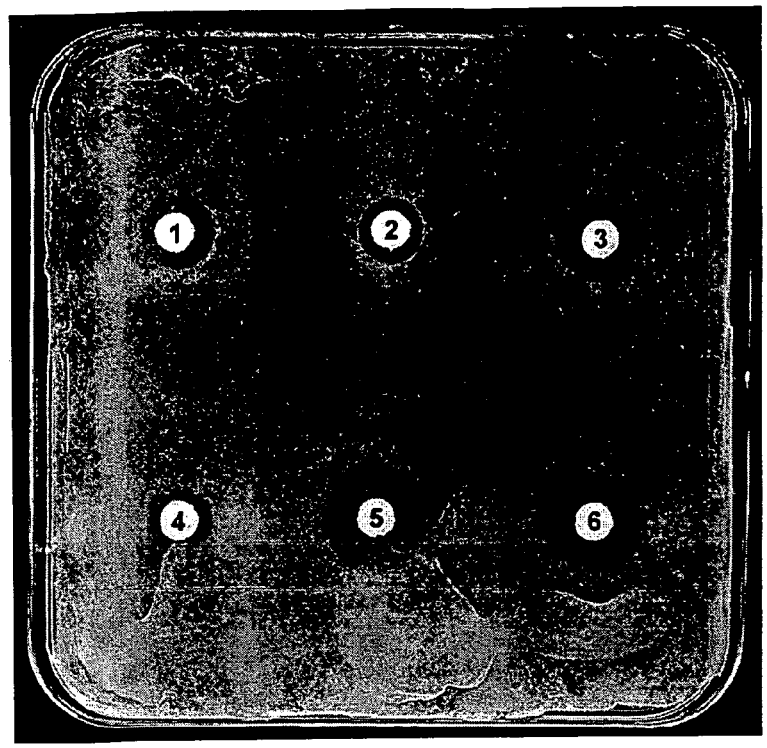
Figure 2C:
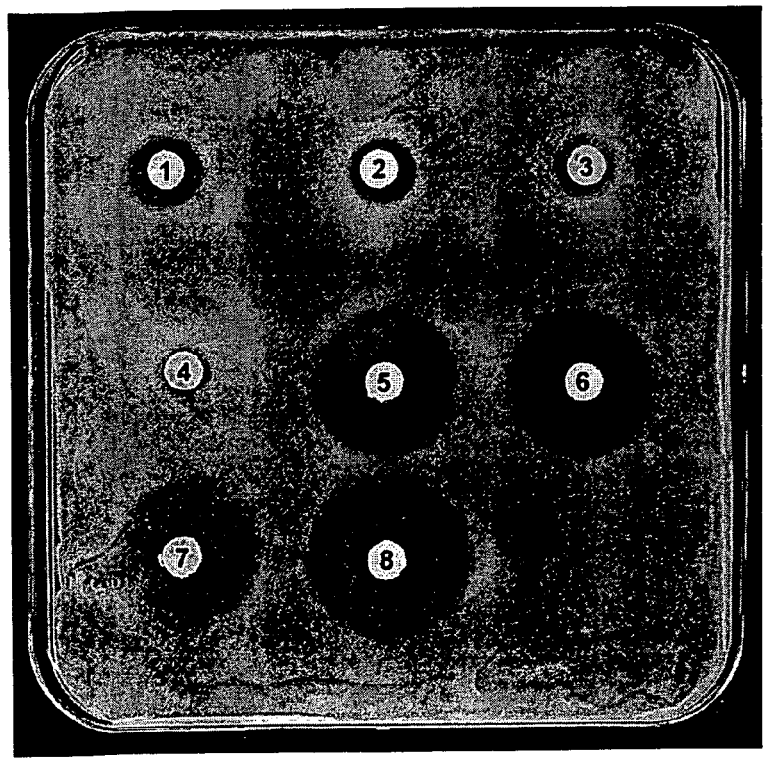

Also in the case of *S. roseosporus* the effect of enhanced ssgA expression on growth rate was positive, although not as strong as in the case of *S. coelicolor* and *S. lividans*, probably because the latter two strains produce larger pellets than *S. roseosporus*. However, the effect of the introduction of pGWS4-SD on antibiotic production by this strain was spectacular. While early samples taken from exponentially growing cells contained little antibiotic, as was apparent from the small zones of clearing in FIG. 2B (control strain, samples 1-3) and FIG. 2C (*S. roseosporus* expressing ssgA, samples 1-4), samples taken from stationary phase cultures (FIG. 2B, samples 5-6; FIG. 2C, samples 5-8) showed a strong increase of the zones growth inhibition around the filter discs. Excitingly, the much larger clearing zones around filter discs containing supernatants from pGWS4-SD transformants as compared to when supernatants from control pSET152 transformants were applied to the discs, clearly show that enhanced expression of ssgA has a very positive effect on the antibiotic production of *S. roseosporus*.

In summary, the experiments described above convincingly show that ssgA has a strongly positive effect on enzyme production and on antibiotic production of several actinomycetes.

ssgR is Important for Correct Sporulation of *S. coelicolor*

Figure 3:
FIG. 3. Morphological development of the ssgA and ssgR mutants of *S. coelicolor*, expressing ssgA or ssgR. These experiments show that ssgA expressed from an ssgR-independent promoter can restore sporulation to an ssgR mutant, but not when expressed from an ssgR-dependent promoter. The strains used in this experiment are.

An ssgR insertional knock-out mutant of *S. griseus* was shown to have a whi (non-sporulating) phenotype (Jiang and Kendrick, 2000). However, since this mutant was created by insertion of a resistance cassette, this effectively blocks transcription from the ssgR promoter into ssgA. To rule out this possibility, and especially to study the role of ssgR in regulating ssgA transcription in *S. coelicolor*, an in-frame-deletion mutant of *S. coelicolor* ssgR was created, as described in the materials and methods section. This effectively removed the approximately 300 bp NcoI-SphI section of ssgR, resulting in an in-frame deletion rendering ssgR effectively inactive (FIG. 4A). This mutant was designated GSR1. GSR1 had a phenotype very similar to that of the ssgA mutant GSA3, forming aerial hyphae, but few spores, and only after prolonged incubation on SFM plates (FIG. 3). Apparently, the ssgRA gene cluster has a very similar role in *S. coelicolor* and *S. griseus*.

Transcription of ssgR is Developmentally Regulated

To analyze the growth-phase-dependent transcription of ssgR, nuclease S1 mapping experiments were performed on RNA isolated from solid cultures of *S. coelicolor* M145. RNA was isolated at 12 to 24-hour intervals during five days, so as to provide representative samples to analyze development-dependent transcription. A 393 bp DNA fragment encompassing the −320/+72 region relative to the translational start site of ssgR, was amplified by PCR, with the relevant 20-mer oligonucleotides, and used as probe. Two transcripts were observed with a length of approximately 210 and 72 nt. The 5' ends of these transcripts correspond to nt positions −135 and +1, relative to the translational start site of ssgR, respectively. Thus, the latter transcript lacks a leader sequence. Transcription is developmentally regulated, and is strongly enhanced after approximately 64 hours, corresponding to the onset of sporulation.

ssgA Expression Depends on an Active SsgR

Since ssgR and ssgA are transcriptionally linked (van Wezel et al., 2000c), and both are essential for correct sporulation, a functional relationship between the two genes was investigated. ssgR encodes a member of the family of IclR-type regulators, including several repressors and activators.

To analyze the possible dependence of ssgA transcription on SsgR, nuclease S1 mapping experiments were performed on RNA isolated from solid cultures of *S. coelicolor* M145, and its congenic ssgR in-frame deletion mutant GSR1. A 233 bp DNA fragment encompassing the −192/+41 region relative to the ssgA translational start site was amplified by PCR, with oligonucleotides T7-AF ($^{32}$P-labeled at its 5' end) and T7-AR (FIG. 4B), and used as probe in the mapping experiments.

RNA was isolated at 12 to 24-hour intervals for five days, so as to provide representative samples to analyze development-dependent transcription. In wild-type S. coelicolor, two transcripts were observed of approximately 115 nt and 100 nt (bands A1 and A2 in FIG. 6, respectively). Promoter probe data indicated that ssgA is transcribed from the ssgR promoter as well as from its own promoter. However, it is unclear if both bands A1 and A2 represent de novo transcription. If so, the promoter sequences overlap. The abundance of both ssgA transcripts increased, reaching a maximum after approximately 80 hours, corresponding to sporulation. Interestingly, ssgR transcripts reached a maximum already after 64 hours (using the same RNA samples), corresponding to the onset of sporulation. This is in accordance with our complementation data, and suggests that SsgR activates transcription of ssgA. To test this hypothesis, transcription of ssgA in the ssgR mutant was analyzed.

Excitingly, no ssgA transcripts could be detected in the ssgR mutant (FIG. 6, right panel). Therefore, we conclude that SsgR is a likely transcriptional activator of ssgA.

Expression of SsgA (SEQ ID NO:11) Restores Sporulation to an ssgR Mutant

If the non-sporulating phenotype of the ssgR mutant is solely due to the absence of ssgA transcripts, it follows that expression of SsgA (SEQ ID NO:11) in such a mutant would counteract the mutation. Therefore, two constructs were introduced into GSR1, one with ssgA preceded by its own (SsgR-activated) regulatory sequences, and one with ssgA positioned behind the SsgR-independent and constitutive ermE promoter. In a control experiment, we also introduced ssgR expression constructs in the ssgA mutant. In this case, no effect was expected. In another control experiment, it was tested if the ssgR and ssgA mutants could be complemented by wild-type copies of ssgR and ssgA, respectively. The results are shown in FIG. 3.

Expectedly, the ssgA and ssgR mutants could be complemented by the introduction of wild-type ssgA (using plasmid pGWS4; van Wezel et al., 2000c) and ssgR (using plasmid pGWR1, see Materials and Methods section), respectively. This underlines that the non-sporulating phenotype of the ssgR and ssgA mutants is solely due to the absence in these mutants of ssgR or ssgA, respectively.

As shown in FIG. 3, the data clearly show that expression of ssgR has no effect on the development of the ssgA mutant. Interestingly, expression of ssgA using the SsgR-independent ermE promoter fully restored development, while introduction of multiple copies of ssgA behind its own promoter did not complement the ssgR mutant (FIG. 3, GSR3 and GSR4, respectively). Again, this strongly suggests that SsgR activates ssgA transcription. Apparently, positioning of an ssgR-independent promoter in front of ssgA relieves its dependence on an active copy of ssgR. This allows altering the regulation of ssgA expression, offering possibilities for growth improvement of Streptomyces.

DNA Sequences Required for, and Mode of, SsgR Binding to the ssgA Promoter Region Interestingly, a clone harboring 233 bp upstream of the translational start codon of ssgA showed no detectable promoter activity, even though S1 nuclease mapping experiments revealed two transcription starts in this region (see previous section). The clone was sequenced, and shown to contain the published DNA sequence. This is apparently confirmed by promoter-probe experiments using a clone with a larger upstream region (fragment 2 in FIG. 15A), which did stimulate Red production. The possibility that the DNA sequence added to fragment 1 to give fragment 2 (FIG. 15A) one or more promoters, was ruled out by nuclease S1 mapping experiments, which failed to reveal a transcriptional start site inside the ssgR gene (not shown).

It is most likely that the DNA sequence between nt positions −600/−50, relative to the ssgA translational start site, contains all the necessary elements for activation of ssgA transcription by SsgR. Members of the superfamily of Ic1R-like regulators bind as homodimers to two well-separated imperfect inverted repeats, so that in total four proteins must bind for activity (see, for example, Zhang et al., 2002). These inverted repeats are separated by at least 100 bp, and on binding, the spacer DNA is folded away. It is likely that the region around the stop codon of the ssgR gene constitutes the downstream one of these two elements; it is highly conserved among S. coelicolor and S. griseus (FIG. 4C), and harbors an A-rich stretch similar to that found for other Ic1R-type binding sites.

Activity of Ic1R-like regulators is lost on binding of a substrate. While this substrate is not yet known, we anticipate that this may be a high-energy metabolic intermediate such as acetyl-CoA, phosphoenolpyruvate (PEP) or citrate, which signal a nutrient-rich state. Alteration of the substrate-binding domain should allow the use of unique and non-metabolizable inducers, for improved control of growth and morphology of Streptomyces in liquid-grown cultures.

SsgR has a Similar Effect on Morphology and Fragmentation of Liquid-Grown Cultures of S. coelicolor as SsgA (SEQ ID NO:11)

Since we here show that SsgR transactivates ssgA, it is logical that overexpression of SsgR stimulates ssgA, and thus fragmentation of the mycelium. Indeed, introduction of low- and high-copy number vectors into S. coelicolor M145 results in similar fragmentation as observed for ssgA overexpression, with increased fragmentation and reduced branching, with a stronger effect when multi-copy constructs were used (not shown).

Summarizing the regulatory role of SsgR, it is a key regulator of ssgA expression, and provides a very useful tool to fine tune or modulate the expression pattern of ssgA, and hence control mycelial morphology of streptomycetes and other actinomycetes in submerged culture, and especially in industrial fermentations.

SsgA (SEQ ID NO:11) belongs to a family of developmentally active proteins

The recently completed genome sequences of S. avermitilis and S. coelicolor revealed six and seven genes with relevant homology to ssgA, respectively (Bentley et al., 2002; Ikeda et al., 2003). The genes encode relatively small (130-140 aa) proteins, which share between 30-50% amino acid identity (Keijser et al., 2003; van Wezel et al., 2000c). The herein described and used Ssg proteins have been renamed to bring their names into conformity with Keijser et al. (SsgE (SEQ ID NO:14) and SsgG (SEQ ID NO:10)). Proteins with relevant similarity to SsgA (SEQ ID NO:11) are designated SALPs (SsgA-like Proteins). Homologues of S. coelicolor ssgA (Sco3926), ssgB (Sco1541), ssgD (Sco7622), and ssgE (Sco3158), are found on the S. avermitilis genome (Sav3926, 6810, 1687, and 3605, respectively), with high conservation in these otherwise distantly related species: the ssgB gene products differ in only one amino acid residue. The highest conservation is found in two sections of the proteins, corresponding to amino acid residues 13-30 and 40-65 of SsgA (SEQ ID NO:11). In total 20 amino acid residues (about 15% of the protein) are fully conserved among all 19 SALP proteins identified so far. However, there are no sequences in these proteins that resemble known functional motifs.

Determining Signatures for SALP-Family Proteins

The amino acid sequences of the SALP-family proteins from *S. coelicolor* were retrieved from the Entrez protein databases at NCBI (world wide web3 (www3). Ncbi.nlm.nih.gov/Entrez/index.htlm). The multalin program (Corpet, 1988) was used to create a multiple alignment of these sequences. The output file was loaded into the software Boxshade (world wide web (www).ch.embnet.org/software/box form.html. The resulting alignment of the *S. coelicolor* SALPs is shown in FIG. 7, with identical and similar amino acids shaded black and grey, respectively.

Short amino acid stretches showing high homology among all orthologues were selected and used to search the SWISSPROT and TrEMBL databases with the ScanProsite program for matching protein sequences (Gattiker et al., 2002). The identity of the hits with these searches determined whether the signature sequence had to be adjusted. The sequence was made more specific when too many hits were obtained, while one or more degenerations were allowed in case not all known SsgA-like amino acid sequences were detected by the search pattern. The process was reiterated until enough specificity was achieved. Eventually, the following signatures for SsgA-like proteins were distilled:

```
signature A =                            (SEQ ID NO: 1)
[IV] [PL] [AV]x[FL]XY[DEH]X(2,3)[DH]P signature B =                            (SEQ ID NO: 2)
WX[FVL]XR[ED][LM][LV]XXG signature C =                            (SEQ ID NO: 3)
WX[FVL]XR[ED][LM] [LV]XXGX(5)GXG[DE]V
```

Where [IV] represents I or V in a particular position, X represents any amino acid, and X(n) means a number (n) of ambiguous amino acids. Signatures A (SEQ ID NO:1) and C (SEQ ID NO:3) exclusively recognized all SsgA-like sequences, while signature B (SEQ ID NO:2) (a shorter and therefore less limiting version of signature C (SEQ ID NO:3)) also detected a few other protein sequences, including putative morpho-proteins.

Complementation of the ssgA Mutant by ssgA-Like Genes

To establish if any of the ssgA-like genes constitutes a functional homologue of ssgA, pHJL401-derived low-copy number vectors (10 copies per chromosome) harboring the respective genes ssgB-G (see Materials and Methods section) were introduced in the ssgA mutant. None of these constructs restored full development (particularly sporulation) to the ssgA mutant, illustrating that increasing the copy number and expression level of these genes does not fully compensate for the absence of SsgA (SEQ ID NO:11). Since in this particular experiment the ssgA-like genes are expressed from their own promoters, we also used hybrid constructs in which the ssgA-like genes were regulated in the same way as the ssgRA operon. Tn this way, effects due to differences in timing of gene expression or in the highly heterologous N-terminal sections of the proteins, were ruled out. The constructs are described in the Materials and Methods section, and represented schematically in FIG. 9A. Surprisingly, despite the low degree of homology (less than 40% aa identity for the predicted gene products), introduction of multiple copies of the ssgRC hybrid gene restored sporulation to the ssgA mutant, producing plenty viable spores. Therefore, SsgC (SEQ ID NO:15) is most likely a functional homologue of SsgA (SEQ ID NO:11). No visible complementation of the ssgA mutant was observed when any of the other genes ssgB, ssgD, ssgE, ssgF, or ssgG (the latter not shown) were introduced, suggesting these morphogenes are not functionally related to ssgA.

ssgB Strongly Affects Morphology and Development of *S. coelicolor*

To further study the role of ssgB in the development of *S. coelicolor* M145, the corresponding gene was disrupted. The gene organization around ssgB is shown in FIG. 8A. ssgB was replaced by the apramycin resistance cassette aacC4, using suicide vector pGWB2 (see Materials and Methods section). The knock-out strategy resulted in replacement of the complete coding sequence of ssgB by the apramycin cassette in a created BamHI site. Integrity of the resulting ssgB mutants (designated GSB1) was confirmed by Southern hybridization (not shown).

The ssgB disruption mutants were arrested in the aerial growth phase, failing to produce spores (FIG. 11). Phase contrast microscopy revealed long, undifferentiated aerial hyphae and confirmed the absence of spores (not shown). Thus, ssgB is a so-called whi (sporulation) gene. Introduction of ssgB into GSB1 on the low-copy number vector pHJL401 restored sporulation (confirmed by phase-contrast microscopy). Surprisingly, GSB1 colonies were significantly larger than those of the parental M145. In *E. coli*, such large colonies are induced by the MLC (Making Large Colonies) phenotype, most likely due to pleiotropic and favorable effects on glucose uptake and/or glycolytic activity. We propose that ssgB directly or indirectly acts as a repressor of an MLC system in *Streptomyces*. The larger colonies reflect enhanced growth rates. Much to our surprise, GSB1 transformants produced increased levels of actinorhodin. Thus, deletion of ssgB results in pleiotropic effects on morphology and antibiotic production.

The morphology of surface-grown colonies of *S. coelicolor* GSB1 and its parental strain M145 were analyzed by cryo scanning electron microscopy. While M145 produced long and regular spore chains, GSB1 formed very smooth and non-coiling aerial hyphae, failing to sporulate (FIG. 12). The mutants appear to be blocked in an early stage of aerial growth, although the morphology of whi mutants does not necessarily correspond to a frozen developmental stage. Few irregularly shaped, branched spore chains could be identified. In these pseudo-sporulating hyphae, septum distance varied greatly, as transpired from study of the mutant by transmission electron microscopy (not shown).

To test the effect of enhanced expression of ssgB on the morphology of *S. coelicolor*, this strain was transformed with a multi-copy plasmid containing the ssgB gene and 500 bp of upstream sequence, containing the putative ssgB promoter. These transformants produced significantly smaller pellets (FIG. 13). Furthermore, fragmentation was enhanced by ssgB, although not as severe as that observed for ssgA. Considering the effect of SsgB (SEQ ID NO:9) on the morphology of liquid-grown mycelium, and the significantly enlarged colonies formed by the ssgB deletion mutant, it is clear that ssgB plays a role in determining mycelial morphology.

Effect of in Creased Expression of Other ssgA-like Genes on the Morphology of *S. coelicolor*

To analyze possible effects of ssgC, ssgD, ssgE, ssgF, and ssgG on mycelial morphology in liquid culture, pHJL401- and pWHM3-derived constructs harboring these genes and their promoters (see M&M section) were introduced into *S. coelicolor*, and the resulting transformants were subsequently cultivated in YEME or in TSBS medium. The mycelial morphology was checked by phase-contrast microscopy.

While no noticeable effect was observed for increased expression of ssgE and ssgG, exciting morphological effects were observed in transformants over-expressing ssgC, ssgD or ssgF.

Introduction of pWHM3/ssgC in *S. coelicolor* resulted in a phenotype reminiscent of the same strain harboring ssgA, only with a far less pronounced effect; it resulted in more open mycelial structures, and a slight degree of fragmentation. Unexpectedly, introduction of pWMH3/ssgD results in extremely small colonies which can hardly grow, and pHJL401/ssgD transformants form strongly condensed mycelial clumps. Close analysis of these clumps suggested a strong degree of branching, probably as the result of overexpression of ssgD. Interestingly, overexpression of the vegetatively expressed ssgD has an almost opposite effect as overexpression of the developmentally regulated genes ssgA, ssgB, and ssgC, which have different effects on growth and morphology, but all result in open and/or fragmented mycelial structures, with reduced branching.

Finally, overexpression of ssgF using pWHM3/ssgF completely blocked sporulation of *S. coelicolor*. Furthermore, antibiotic production was strongly enhanced, an effect observed in both solid- and liquid-grown cultures. No significant changes in mycelial morphology of liquid-grown cultures were observed.

The exciting observation that overexpression of SALP-family proteins has diverse and very different effects on the morphology and on antibiotic production of *Streptomyces* in submerged culture as well as on plates, suggests that together, these four genes can be exploited to finely control the morphology and antibiotic production of *streptomycetes* and other actinomycetes. This discovery is expected to have great impact on the control of industrial fermentations. The observations for the function and expression of SALPs are summarized in Table 3.

TABLE 3

Effects of SALP-family proteins on the morphology and antibiotic production of streptomycetes.

| SALP gene | Timing of expression | Effect of overexpression |
| --- | --- | --- |
| ssgA | aerial, sporulation | fragmentation, reduced branching, enhanced growth rate, often enhanced antibiotic production |
| ssgB | aerial | reduced pellet formation, synchronous growth |
| ssgC | aerial, sporulation | reduced branching, smaller pellet size |
| ssgD | vegetative, aerial | growth inhibition |
| ssgE | aerial, sporulation | none detected |
| ssgF | aerial, sporulation | enhanced antibiotic production; inhibition of development |

Placement of the ssgA-like Genes and ssgR in the *S. coelicolor* Life-Cycle

The experiments described above show that transcription of ssgR is initiated at a time point corresponding temporally to the onset of sporulation in solid cultures, and thus approximately to the phase that marks the transition from exponential to stationary phase in submerged cultures. This is immediately followed by the onset of ssgA transcription, as the result of its activation by SsgR.

Figure 10:
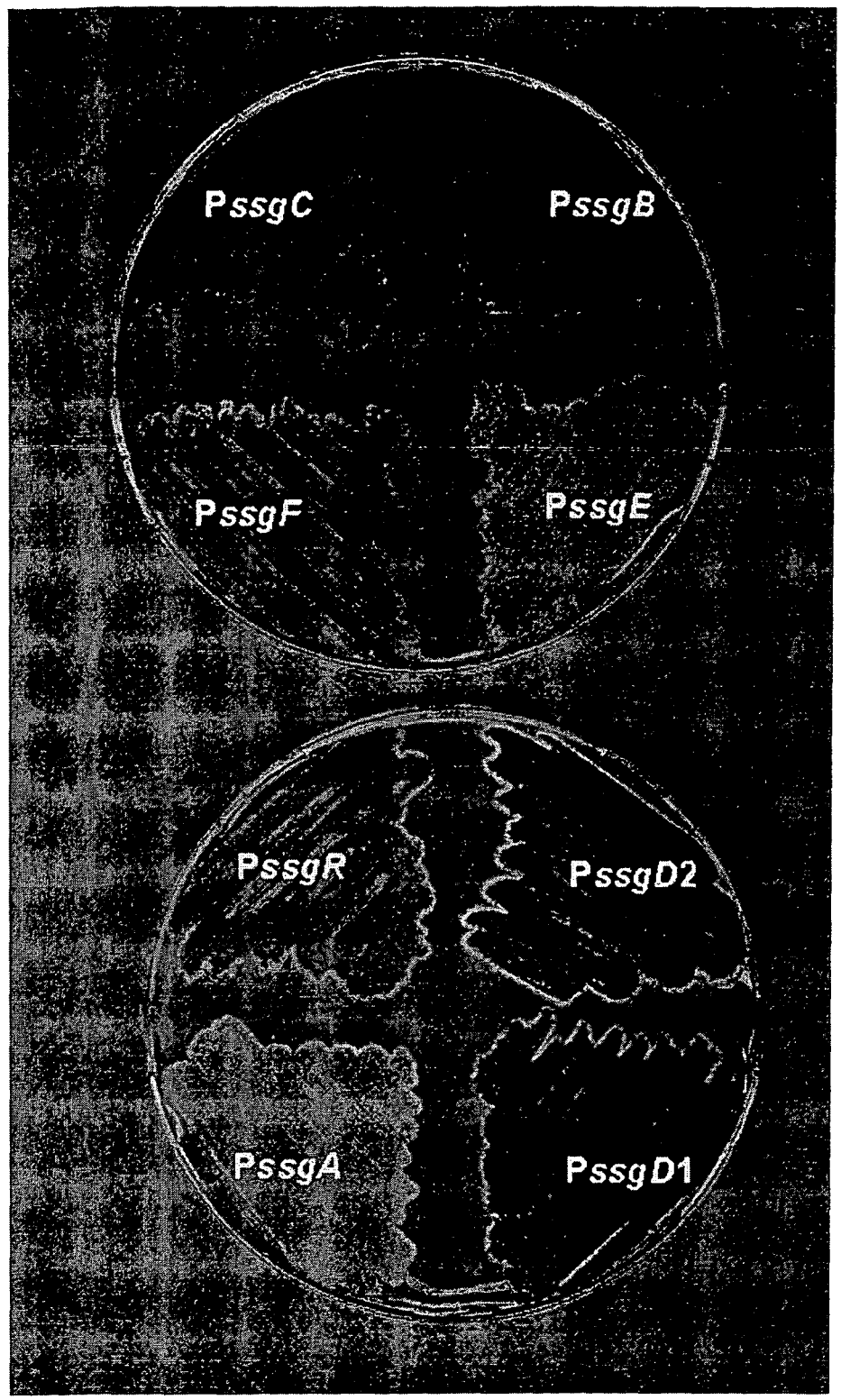

To analyze the timing of transcription of the ssgA-like genes ssgB-G, their respective promoter regions were cloned into pIJ2587, thereby using the production of the red-pigmented antibiotic undecylprodigiosin as a visible marker. The exact nature of the DNA inserts of pIJ2587 are shown in Table 2, and experimental details are given in the Materials and Methods section. The results are shown in FIG. 10. Additional experiments were performed where each of the promoters was tested throughout the life cycle, by streaking transformants every morning and evening for a period of seven days. In this way, the onset of promoter activity could be accurately determined (data not illustrated).

Timing of the expression of most ssgA-like genes was developmentally controlled, and additional experiments showed that ssgA, ssgB, ssgC, ssgE, and ssgF were expressed during aerial growth and sporulation (Table 3). Surprisingly, the ssgD promoter region already stimulated Red production very early during growth, even before colonies were visible, showing that it is expressed during early vegetative growth, and possibly as early as spore germination. This experiment again shows that ssgD is very different from the other SALPs, in terms of the timing of its expression as well as its effect on *Streptomyces* morphology. The insert harboring the upstream region of the ssgG gene hardly stimulated Red production, and if a promoter is located on this DNA sequence, it was too weak to establish its timing. As described above, the DNA fragment harboring the ssgA promoter fails to stimulate Red production due to the lack of the complete SsgR target sequence. The data presented here are summarized in Table 3 and FIG. 14.

Expression of Several of the ssgA-like Genes is Repressed by Glucose

To analyze the transcriptional regulation of the members of the family of ssgA-like morphogenes, the ability of the ssgRA operon promoters, and of the promoters of the individual genes ssgB-ssgG, to transcribe redD in the presence of mannitol or glucose as carbon sources was tested. The plasmids were introduced into *S. coelicolor* M512, and the resulting transformants assayed for Red production. As described above, on the complex medium R2YE, all transformants produced significant amounts of Red, except the control strain M512/pIJ2587, which remained colorless. The ssgD promoter strongly stimulated Red production during early vegetative growth, as soon as colonies were visible. In contrast, transcription from the promoters of all ssgA-like genes, except that of the vegetative ssgD promoter, showed differentiation-dependent expression, with a maximum when aerial mycelium was produced. This shows that these morphogenes are developmentally regulated. To analyze the relationship between feed and morphogenes, the influence of CCR on promoter activity of the various promoters was tested.

Surprisingly, promoters of all ssgA-like genes, except that of the vegetatively expressed ssgD, were repressed specifically by glucose. For this, transformants of M512 harboring the relevant promoter-probe constructs (see Table 2) were grown on MM plates containing either 1% glucose or 1% mannitol as carbon source. As typical examples we show the effect of glucose on the ssgRA promoter regions (various fragments shown in FIG. 15A; plate shown in FIG. 15B), and on the ssgC and ssgD promoters (pIJ2587-ssgCp or pIJ2587-ssgDp, FIG. 16). While the vegetative ssgDp invariably stimulated Red production, independent of the carbon source, glucose had a strong repressive effect on the activity of the developmental ssgR, ssgA, and ssgC promoters, as shown in FIGS. 15 and 16, respectively. This strongly suggests that the genes are under CCR. Introduction of the same promoter-probe vectors into a glucose kinase mutant derivative of M512, designated M512 ΔglkA, revealed that glucose had no repressive effect on the promoters in this strain (FIG. 17). This proves that glucose repression of these promoters occurs in a CCR-dependent manner.

Effect of Carbon Utilization on Antibiotic Production

In biotechnological fermentations, it is of course profitable to use cheap carbon sources, such as molasses and other less well-defined sugar extracts. However, we noticed a severe dependence of antibiotic production on the carbon source used. To assess the nature of these effects, we streaked *S. coelicolor* M145 (wild-type) and seven congenic mutant derivatives of this strain on NMMP plates with various carbon sources. We analyzed mutants of the Act biosynthesis pathway (M511, to study Red production), of the Red biosynthesis pathway (M510, M550; to study Act production), of the pleiotropic regulatory gene afsR (disturbed in regulation of the Red and Act pathways) and an afsR suppressor, of the maltose repressor gene malR, and of the glkA mutant J1915. The latter is a control to establish if the effects can be related to glucose repression, which is absent in this mutant. The results are shown in FIG. 18.

While galactose, xylose, and sucrose failed to stimulate antibiotic production in many of the strains used except the ACT- and RED-overproducing afsRsup, arabinose and rhamnose strongly stimulated pigment production in all strains used. For example, the redD mutant (M510) produces no visible antibiotics on most of the carbon sources used, but large amounts of ACT on arabinose and on rhamnose. Interestingly, the sugars have different effects on different strains: while pigment production is stimulated in some strains, it is repressed in others.

Unexpectedly, CCR has no direct effect on antibiotic production: while strains grown on glucose generally show reduced levels of antibiotic production, glucose has the same effect on the wild-type (M145) as on its congenic glkA mutant (J1915), which lacks glucose repression. Also, we observed no difference in antibiotic production by strains grown on arabinose alone or on a combination of glucose and arabinose. Surprisingly, arabinose and rhamnose strongly stimulated antibiotic production in all strains, while production is very low on sugars such as sucrose and xylose. Therefore, it is clear that the effect of carbon utilization should be carefully checked for each individual mutant and antibiotic. Arabinose and rhamnose are metabolized via the pentose phosphate pathway. Affecting this route has a stimulatory effect on carbon fluxes feeding secondary metabolism.

This is a very important observation, as glucose is a major constituent of large-scale fermentations, and repression of ssgRA, ssgB, and ssgC would have a dramatic influence on mycelial morphology, resulting in enhanced branching and reduced fragmentation, and therefore—undesirably—in large mycelial clumps. These negative effects are counteracted by using non-repressing carbon sources, although these are typically pure and therefore more expensive, or by the enhanced expression of ssgA, ssgB, ssgC, and/or ssgR (van Wezel et al., 2000 bcd).

Analysis of the Effect of Carbon Utilization on glkA Expression

Glucose kinase is expressed constitutively in submerged cultures, independent of the carbon source used (Mahr et al., 2000). This is logical, since glucose kinase is known to be involved in CCR exerted by glucose, but also by carbohydrates that do not require the presence of a catalytically active glucose kinase. Furthermore, glucose kinase activity was similar in stationary phase cultures of *S. coelicolor* A3(2) M145 wild-type cells grown in liquid minimal medium under repressing and non-repressing conditions, using glucose, fructose, glycerol, or mannitol as the sole carbon source, respectively.

To assess the growth-phase dependence of glucose kinase activity, *S. coelicolor* M145 was grown in the phosphate-rich minimal medium NMMP, with casaminoacids (CAS) and glucose or mannitol as the carbon source. Western analysis showed that glucose kinase was produced constitutively in both cultures (FIG. 20). Surprisingly, two minor bands appeared, migrating slightly faster than the main Glk band. These bands were particularly strong during mid- and late exponential growth in the presence of glucose (17 to 24 hours), but not in the mannitol-grown cultures. To assess the relationship between the appearance of these bands and Glk activity, protein extracts prepared from the same growth curves were analyzed using a glucose kinase activity assay. In obvious conflict with the significant amount of Glk present in the protein extracts, hardly any activity was observed in the mannitol-grown cultures during exponential growth, but increased when stationary phase was reached. Even more surprisingly, we observed a sharp rise in Glk activity (up to approximately 500 nmol/min.mg) during mid-exponential phase in the glucose-grown cultures (FIG. 19), coinciding with the appearance of the two faster migrating protein bands after approximately 17 hours. On transition to stationary phase, activity dropped to a significantly lower level, comparable to that of mannitol-grown cultures.

*S. coelicolor* has a second gene encoding a protein with glucose kinase activity, designated GlkII (Genbank accession number SCO6260), which is inactive in normal cells, and whose expression can be induced at high frequency in glkA mutants grown for a prolonged period in the presence of glucose (Angell et al., 1994). However, the protein is significantly larger than Glk (355 instead of 318 residues), and can therefore not correspond to the faster migrating bands. Several more proteins with similarity to Glk occur in *S. coelicolor*, but their homology to Glk (far less than 40% amino acid identity) is most likely too low for cross-reactivity of the antibodies. Glucose kinase is probably activated by post-translational modification (van Wezel, unpublished results).

Effect of pH on Morphology

Extensive studies of morphological characteristics of actinomycetes under different culture conditions showed that in non-buffered submerged cultures, fragmentation strongly increased towards stationary phase. This surprising observation prompted analysis of pH effects on morphology of actinomycetes. For this purpose, the actinomycetes *Saccharopolyspora erythraea, Streptomyces coelicolor, Streptomyces clavuligerus*, and *Streptomyces lividans* were grown in 100 ml TS cultures buffered with 100 mM MOPS at pH 4.5, 5.0, 5.5, 6.0, 7.0 or 8.0. Interestingly, all actinomycetes analyzed showed reduced pellet formation and reduced branching as soon as pH dropped to between 5.5 and 6.0. The effect was even more pronounced when transformants harboring ssgA-expression plasmid pGWS4-SD were analyzed. A typical example of such an experiment is shown in FIG. 21, showing *S. coelicolor* with pGWS4-SD after 30 hours of growth in buffered TS medium.

While strong fragmentation typical of ssgA overexpression was observed at a pH 5.5 or lower, larger mycelial structures were formed in cultures buffered at pH of 6.0 and higher, with a gradual increase of mycelium size on increasing pH. Apparently, an important physiological change is effected by alteration of pH, which can be exploited to increase or reduce fragmentation of liquid-grown *Actinomyces* mycelium, depending on what is desirable at a certain stage of the production process.

This is a very important new observation, which allows the control of mycelial morphology as well as the fine tuning of SsgA- (SEQ ID NO:11-) induced fragmentation by fluctuation of the pH. Ideally, precultures should contain fragmented mycelium, with average mycelium size 10-50 μm. In that way, the preculture contains a maximal number of growth nuclei, which show optimal transfer of nutrients and oxygen due to the small mycelium size, which strongly reduces the start-up (lag) phase (see also FIG. 1). In our 5L fermentation experiments (such as shown in FIGS. 1 and 2) this lag phase varied between four hours (fragmented preculture) and 12 hours (large pellets in preculture). However, in the production phase, typically after completion of the exponential growth phase, larger mycelial structures are required, with an optimal average pellet size between 80-200 μm. Shorter mycelial structures generally fail to produce antibiotics (Martin and Bushell, 1996). Obviously, the pH used in the final fermentation process is dictated by production considerations, e.g. to optimize the stability of an enzyme or a secondary metabolite or antibiotic.

Considering the excited observation outlined above, we state that pH effects may now be used to optimize the production process. The observed pH effect may be used alone or in combination with one of the herein disclosed agents for altering the morphology of microstructures of filamentous microorganisms.

REFERENCES

Angell, S., Lewis, C. G., Buttner, M. J., and Bibb, M. J. 1994. Glucose repression in *Streptomyces coelicolor* A3(2): a likely regulatory role for glucose kinase. *Mol. Gen. Genet.* 244: 135-143.

Angell, S., Schwarz, E., and Bibb, M. J. 1992. The glucose kinase gene of *Streptomyces coelicolor* A3(2): its nucleotide sequence, transcriptional analysis and role in glucose repression. *Mol. Microbiol.* 6: 2833-2844.

Bentley, S. D., Chater, K. F., Cerdeno-Tarraga, A. M., Challis, G. L., Thomson, N. R., James, K. D., Harris, D. E., Quail, M. A., Kieser, H., Harper, D., Bateman, A., Brown, S., Chandra, G., Chen, C. W., Collins, M., Cronin, A., Fraser, A., Goble, A., Hidalgo, J., Hornsby, T., Howarth, S., Huang, C. H., Kieser, T., Larke, L., Murphy, L., Oliver, K., O'Neil, S., Rabbinowitsch, E., Rajandream, M. A., Rutherford, K., Rutter, S., Seeger, K., Saunders, D., Sharp, S., Squares, R., Squares, S., Taylor, K., Warren, T., Wietzorrek, A., Woodward, J., Barrell, B. G., Parkhill, J., Hopwood, D. A. 2002. Complete genome sequence of the model *actinomycete Streptomyces coelicolor* A3(2). *Nature* 417: 141-147.

Bibb, M. J. 1996. The regulation of antibiotic production in *Streptomycetes*. *Microbiology* 142: 1335-1344.

Bierman, M., Logan, R., O'Brien, K., Seno, E. T., Rao, R. N., and Schoner, B. E. 1992. Plasmid cloning vectors for the conjugal transfer of DNA from *Escherichia coli* to *Streptomyces* spp. *Gene* 116: 43-49.

Butler, M. J., Deutscher, J., Postma, P. W., Wilson, T. J., Galinier, A., and Bibb, M. J. 1999. Analysis of a ptsH homologue from *Streptomyces coelicolor* A3(2). *FEMS Microbiol. Lett.* 177: 279-288.

Chater, K. F. 1993. Genetics of differentiation in *Streptomyces*. *Annu. Rev. Microbiol.* 47: 685-713.

Chater, K. F. 1998. Taking a genetic scalpel to the *Streptomyces* colony. *Microbiology* 144: 1465-1478.

Corpet F. Multiple sequence alignment with hierarchical clustering. 1988. *Nucleic Acids Res.* 16: 10881-10890.

Floriano, B., and Bibb, M. J. 1996. afsR is a pleiotropic but conditionally required regulatory gene for antibiotic production in *Streptomyces coelicolor* A3(2). *Mol. Microbiol.* 21: 385-396.

Gattiker A., Gasteiger E., and Bairoch A. 2002. ScanProsite: a reference implementation of a PROSITE scanning tool. *Applied Bioinformatics* 1: 107-108.

Hindle, Z., and Smith, C. P. 1994. Substrate induction and catabolite repression of the *Streptomyces coelicolor* glycerol operon are mediated through the GylR protein. *Mol. Microbiol.* 12: 737-745.

Ikeda, H., Ishikawa, J. Hanamoto, A., Shinose, M., Kikuchi, H., Shiba, T., Sakaki, Y., Hattori, M., Omura, S. 2003. Complete genome sequence and comparative analysis of the industrial microorganism *Streptomyces avermitilis*. *Nature Biotechnol.* 14: 14.

Janssen, G. R. and Bibb, M. J. 1993. Derivatives of pUC18 that have BglII sites flanking a modified multiple cloning site and that retain the ability to identify recombinant clones by visual screening of *Escherichia coli* colonies. *Gene* 124: 133-134.

Jiang, H., and Kendrick, K. E. 2000. Characterization of ssfR and ssgA, two genes involved in sporulation of *Streptomyces griseus*. *J. Bacteriol.* 182: 5521-5529.

Katz, E., Thompson, C. J., and Hopwood, D. A. 1983. Cloning and expression of the tyrosinase gene from *Streptomyces antibioticus* in *Streptomyces lividans*. *J. Gen. Microbiol.* 129: 2703-2714.

Kawamoto, S., Watanabe, H., Hesketh, A., Ensign, J. C., and Ochi, K. 1997. Expression of the ssgA gene product, associated with sporulation and cell division in *Streptomyces griseus*. *Microbiology* 143: 1077-1086.

Keijser, B. J., Noens, E. E., Kraal, B., Koerten, H. K., van Wezel, G. P. 2003. The *Streptomyces coelicolor* ssgB gene is required for early stages of sporulation. *FEMS Microbiol Lett.* 225: 59-67.

Kelemen, G. H., Plaskitt, K. A., Lewis, C. G., Findlay, K. C., and Buttner, M. J. 1995. Deletion of DNA lying closes to the glkA locus induces ectopic sporulation in *Streptomyces coelicolor* A3(2). *Mol. Microbiol.* 17: 221-230.

Kieser, T., Bibb, M. J., Buttner, M. J., Chater, K. F., and Hopwood, D. A. 2000. Practical *Streptomyces* genetics. Norwich, U.K.: John linnes Foundation.

Kwakman, J. H. J. M., and Postma, P. W. 1994. Glucose kinase has a regulatory role in carbon catabolite control in *Streptomyces coelicolor*. *J. Bacteriol.* 176: 2694-2698.

Larson, J. L., and Herschberger, C. L. 1986. The minimal replicon of a *streptomycete* plasmid produces an ultrahigh level of plasmid DNA. *Plasmid* 15: 199-209.

Lerch, K. and Ettinger, L. 1972. Purification and characterization of a tyrosinase from *Streptomyces glaucescens*. *Eur. J. Biochem.* 31: 427-37.

Mahr, K., van Wezel, G. P., Svensson, C., Krengel, U., Bibb, M. J., and Titgemeyer, F. 2000. Glucose kinase of *Streptomyces coelicolor* A3(2): large-scale purification and biochemical analysis. Antonie van Leeuwenhoek 78: 253-261.

Martin, S. M., and Bushell, M. B. 1996. Effect of hyphal micromorphology on bioreactor performance of antibiotic-producing *Saccharopolyspora erythraea* cultures. *Microbiology* 142: 1783-1788.

Messing, J., Crea, R., and Seeburg, P. H. 1981. A system for shotgun DNA sequencing. *Nucleic Acids Res.* 9: 309-321.

Parche, S., Schmid, R., and Titgemeyer, F. 1999. The phosphotransferase system (PTS) of *Streptomyces coelicolor*:

identification and biochemical analysis of a histidine phosphocarrier protein HPr encoded by the gene ptsH. *Eur. J. Biochem.* 265: 308-317.

Sambrook J., Fritsch E. F., and Maniatis T. 1989. Molecular cloning: a laboratory manual. In: 2nd ed. Cold Spring Harbor Laboratory Press, Cold Spring Harbor, N.Y.

Skarlatos, P. and Dahl, M. K. 1998. The glucose kinase of *Bacillus subtilis. J. Bacteriol.* 180: 3222-3226.

van Wezel, G. P., White, J., Young, P., Postma, P. W., and Bibb, M. J. 1997. Substrate induction and glucose repression of maltose utilization by *Streptomyces coelicolor* A3(2) is controlled by malR, a member of the lacI-galR family of regulatory genes. *Mol. Microbiol.* 23: 537-549.

van Wezel, G. P., White, J., Hoogvliet, G., and Bibb, M. J. 2000a. Application of redD, the transcriptional activator gene of the undecylprodigiosin biosynthetic pathway, as a reporter for transcriptional activity in *Streptomyces coelicolor* A3(2) and *Streptomyces lividans. Journal of Mol. Microbiol. Biotechnol.* 2: 551-556.

van Wezel, G. P., van der Meulen, J., Taal, B., Koerten, H. K., and Kraal, B. 2000b. Effects of increased and deregulated expression of cell division genes on the morphology and on antibiotic production of *streptomycetes*. Antonie van Leeuwenhoek 78: 269-276.

van Wezel, G. P., van der Meulen, J. Kawamoto, S., Luiten, R. G. M., Koerten, H. K., and Kraal, B. 2000c. ssgA is essential for sporulation of *Streptomyces coelicolor* A3(2) and affects hyphal development by stimulating septum formation. *J. Bacteriol.* 182: 5653-5662.

van Wezel, G. P., Luiten, R. M., and Kraal, B. 2000d. Reducing branching and enhancing fragmentation in antibiotic-producing actinomycetes. World and European patent application, EP0974657.

Vara, J., Lewandowska-Skarbek, M., Wang, Y-G, Donadio, S. and Hutchinson, C. R. 1989. Cloning of genes governing the deoxysugar portion of the erythromycin biosynthesis pathway in *saccharopolyspora erythraea* (*Streptomyces erythreus*). *J. Bacteriol.* 171: 5872-5881.

White, J., and Bibb, M. J. 1997. bldA dependence of undecylprodigiosin production in *Streptomyces coelicolor* A3(2) involves a pathway-specific regulatory cascade. *J. Bacteriol.* 179: 627-633.

Zhang, R. G., Kim, Y., Skarina, T., Beasley, S., Laskowski, R., Arrowsmith, C., Edwards, A., Joachimiak, A., and Sacvchenko, A. 2002. Crystal structure of *Thermotoga maritima* 0065, a member of the IclR transcription factor family. *J. Biol. Chem.* 277: 19183-19190.

---

What is claimed is:

1. A method for improving production of a product of interest in a liquid culture of actinomycetes, the method comprising:
introducing into the actinomycetes an agent for altering morphology of microstructures of the actinomycetes, wherein said agent comprises a gene selected from the group consisting of: SsgB (SEQ ID NO:9), SsgC (SEQ ID NO:15), SsgD (SEQ ID NO:13), SsgF (SEQ ID NO: 12), a functional fragment of SsgB comprising at least amino acids 23-34 and at least amino acids 51-71 of SEQ ID NO:9, a functional fragment of SsgC comprising at least amino acids 24-35 and at least amino acids 52-72 of SEQ ID NO: 15, a functional fragment of SsgD comprising at least amino acids 23-34 and at least amino acids 54-74 of SEQ ID NO: 13, a functional fragment of SsgF comprising at least amino acids 37-48 and at least amino acids 65-85 of SEQ ID NO: 12, or any combination thereof.

2. A method for improving production of a product of interest in a liquid culture of actinomycetes, the method comprising:
introducing into the actinomycetes an agent for altering morphology of microstructures of the actinomycetes, wherein said agent comprises a gene encoding SsgB (SEQ ID NO:9), SsgC (SEQ ID NO:15), a functional fragment of SsgB comprising at least amino acids 23-34 and at least amino acids 51-71 of SEQ ID NO:9, a functional fragment of SsgC comprising at least amino acids 24-35 and at least amino acids 52-72 of SEQ ID NO: 15, or any combination thereof.

3. The method according to claim 2, wherein said liquid culture is a large-scale liquid culture.

4. A method for improving production of a product of interest in a liquid culture of actinomycetes, the method comprising:
introducing into the actinomycetes a gene encoding a SsgA-like protein, wherein the SsgA-like protein comprises a first peptide selected from the group consisting of amino acids 23-34 of SEQ ID NO:9, amino acids 24-35 of SEQ ID NO:15, amino acids 23-34 of SEQ ID NO:13, and amino acids 37-48 of SEQ ID NO:12, and wherein the SsgA-like protein comprises a second peptide selected from the group consisting of amino acids 51-71 of SEQ ID NO:9, amino acids 52-72 of SEQ ID NO:15, amino acids 54-74 of SEQ ID NO:13, and amino acids 65-85 of SEQ ID NO:12.

* * * * *